(12) United States Patent
Mansoor et al.

(10) Patent No.: US 10,975,084 B2
(45) Date of Patent: Apr. 13, 2021

(54) KDM5 INHIBITORS

(71) Applicants: Merck Sharp & Dohme Corp., Rahway, NJ (US); Umar Faruk Mansoor, Hopkinton, MA (US); Christian Fischer, Natick, MA (US); Phieng Siliphaivanh, Newton, MA (US); Luis Torres, Norwood, MA (US); Hakan Gunaydin, Somerville, MA (US); David L. Sloman, Brookline, MA (US)

(72) Inventors: Umar Faruk Mansoor, Hopkinton, MA (US); Christian Fischer, Natick, MA (US); Phieng Siliphaivanh, Newton, MA (US); Luis Torres, Norwood, MA (US); Hakan Gunaydin, Somerville, MA (US); David L. Sloman, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/341,313

(22) PCT Filed: Oct. 6, 2017

(86) PCT No.: PCT/US2017/055464
§ 371 (c)(1),
(2) Date: Apr. 11, 2019

(87) PCT Pub. No.: WO2018/071283
PCT Pub. Date: Apr. 19, 2018

(65) Prior Publication Data
US 2020/0048258 A1 Feb. 13, 2020

Related U.S. Application Data

(60) Provisional application No. 62/407,224, filed on Oct. 12, 2016.

(51) Int. Cl.
*C07D 487/04* (2006.01)
(52) U.S. Cl.
CPC .................. *C07D 487/04* (2013.01)
(58) Field of Classification Search
CPC .................................................... C07D 487/04
See application file for complete search history.

(56) References Cited

U.S. PATENT DOCUMENTS

2007/0112006 A1 5/2007 Schiemann et al.
2013/0317021 A1 11/2013 Wolkerstorfer et al.

FOREIGN PATENT DOCUMENTS

| JP | 57175193 A | 10/1982 |
|---|---|---|
| WO | 2004041825 A1 | 5/2004 |
| WO | 2008037607 A1 | 4/2008 |
| WO | WO2011114148 | 9/2011 |
| WO | WO2011134867 A1 | 11/2011 |
| WO | 2014055634 A1 | 4/2014 |
| WO | 2014139326 A1 | 9/2014 |
| WO | WO2014144850 | 9/2014 |
| WO | 2015035062 A1 | 3/2015 |
| WO | 2015135094 A1 | 9/2015 |

OTHER PUBLICATIONS

Kleinpeter et al (1995): STN International HCAPLUS database, (Columbus, Ohio), Accession No. 1995: 814808.*
Levin et al (1964): STN International HCAPLUS database, (Columbus, Ohio), Accession No. 1964: 3161.*
Allen, C.F.H. et al., The Structure of Certain Polyazaindenes. II. The Product from Ethyl Acetoacetate and 3-Amino-1,2,4-triazole, Journal of Organic Chemistry, 1959, 787-793, 24(6).
Database Registry [Online] Chemical Abstracts Service, Columbus, Ohio, US; Nov. 1, 2011 (Nov. 1, 2011), XP002797332, accession No. 1339185-72-6 Database accession No. 1339185-72-6 *Compound with RN 1339185-72-6 *.
Database Registry [Online] Chemical Abstracts Service, Columbus, Ohio, US; Nov. 10, 2011 (Nov. 10, 2011), XP002797334, accession No. 1343721-15-2 Database accession No. 1343721-15-2 *Compound with RN 1343721-15-2 *.
Database Registry [Online] Chemical Abstracts Service, Columbus, Ohio, US; Jul. 17, 2006 (Jul. 17, 2006), XP002797339, accession No. 893722-40-2 Database accession No. 893722-40-2 *Compound with RN 893722-40-2 *.
Database Registry [Online] Chemical Abstracts Service, Columbus, Ohio, US; Nov. 2, 2011 (Nov. 2, 2011), XP002797333, accession No. 1339404-05-5 Database accession No. 1339404-05-5 *Compound with RN 1339404-05-5 *.
Database Registry [Online] Chemical Abstracts Service, Columbus, Ohio, US; Sep. 20, 2006 (Sep. 20, 2006), XP002797340, accession No. 907972-64-9 Database accession No. 907972-64-9 *Compound with RN 907972-64-9 *.
Database Registry [Online] Chemical Abstracts Service, Columbus, Ohio, US; Oct. 26, 2005 (Oct. 26, 2005), XP002797342, accession No. 866137-36-2 Database accession No. 866137-36-2 *Compound with RN 866137-36-2 *.

(Continued)

*Primary Examiner* — Golam M Shameem
(74) *Attorney, Agent, or Firm* — Jeffrey P. Bergman; Catherine D. Fitch

(57) ABSTRACT

The present invention provides a compound of Formula (I) (represented as tautomers Ia and Ib) or the pharmaceutically acceptable salts thereof, which are KDM5 inhibitors.

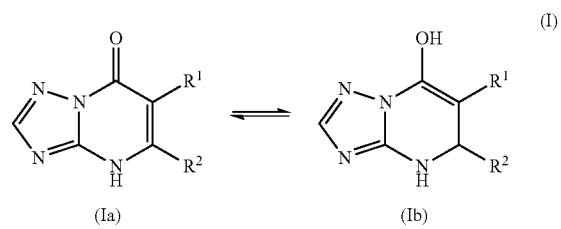

6 Claims, No Drawings

(56) References Cited

OTHER PUBLICATIONS

Database Registry [Online] Chemical Abstracts Service, Columbus, Ohio, US; May 29, 2006 (May 29, 2006), XP002797341, accession No. 885880-25-1 Database accession No. 885880-25-1 *Compound with RN 885880-25-1 *.
Database Registry [Online] Chemical Abstracts Service, Columbus, Ohio, US; Oct. 29, 2003 (Oct. 29, 2003), XP002797343, accession No. 610261-31-09 Database accession No. 610261-31-09 *Compound with RN 510261-31-09 *.
Database Registry [Online] Chemical Abstracts Service, Columbus, Ohio, US; May 31, 2006 (May 31, 2006), XP002797336, accession No. 886145-94-4 Database accession No. 886145-94-4 *Compound with RN 886145-94-4 *.
Database Registry [Online] Chemical Abstracts Service, Columbus, Ohio, US; Mar. 8, 2007 (Mar. 8, 2007), XP002797335, accession No. 925642-77-9 Database accession No. 925642-77-9 *Compound with RN 925642-77-9 *.
Hill, M.A. et al., The Structure of Certain Polyazaindenes. IX. Sensitivity of the Ultraviolet Absorption Spectra to pH Variation, and Amine Salts of Tetrazaindenes, Journal of Organic Chemistry, 1961, 3834-3837, 26(10).
Hlavka, Joseph J. et al., Reactions of 2,3-Diamino-4(3H)-pyrimidinones. II [1], J. Heterocyclic Chem., 1985, 1317-1322, 22(5).
Kofman, T.P. et al., 6-Nitro- and 6-Bromo Derivatives of 4, 7-Dihydro-1,2,4-triazolo[1,5-a]pyrimidin-7-one, Russian Journal of Organic Chemistry, 1997, 1784-1793, 33(12).
Levin, Ya. A. et al., Condensed Heterocycles III.Condensation of 3-Amino-1,2,4-Triazole With Some B-Ketocarboxylic Esters, Journal of General Chemistry USSR, 1963, 2603-2607, 33(8).
Makisumi, Yasuo, Studies on Azaindolizine Compounds. XVI. The Allyl Rearrangement of 7-Allyloxy-5, 6-dimethyls-triazolo [1, 5-a] pyrimidime, Chemical and Pharmaceutical Bulletin, 1963, 859-866, 11(7).
Sato, Yasunobu et al., Studies on cardiovascular agents. 6. Synthesis and coronary vasodilating and antihypertensive activities of 1,2,4-triazolo[1,5-a]pyrimidines fused to heterocyclic systems, Journal of Medicinal Chemistry, 1980, 927-937, 8.
Witschel, Matthias C. et al., Inhibitors of the Herbicidal Target IspD: Allosteric Site Binding, Angewandte Chemie, International Edition, 2011, 7931-7935, 50(34).
Alan R. Katritzky, Tautomerism in drug discovery, J. Comput Aided Mol Des, 2010, 475-484, 24.
E. N. Ulomskiy, Fluorinated [1,2,4]Triazolo[1,5-a]Pyrimidinesand [1,2,4]Triazolo[5,1-c] [1,2,4] Triazines, Chemistry of Heterocyclic Compounds, 2011, 1164-1169, 47-9.

* cited by examiner

KDM5 INHIBITORS

CROSS-REFERENCE TO RELATED APPLICATIONS

This application is the national stage application under 35 U.S.C. 371 of International Patent Application No. PCT/US17/055464, filed Oct. 6, 2017, which claims priority to U.S. Provisional Patent Application No. 62/407,224, filed Oct. 12, 2016. Each of the aforementioned applications is incorporated by reference in its entirety.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation, By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding or chromatin-modifying enzymes. Significantly, an increasing number of these enzymes have been associated with a variety of disorders such as neurodegenerative disorders, metabolic diseases, inflammation, and cancer. Thus, therapeutic agents directed against this emerging class of gene regulatory enzymes promise new approaches to the treatment of human diseases.

Additionally, the relatively rapid acquisition of resistance to cancer drugs remains a key obstacle to successful cancer therapy. Substantial efforts to elucidate the molecular basis for such drug resistance have revealed a variety of mechanisms, including drug efflux, acquisition of drug binding-deficient mutants of the target, engagement of alternative survival pathways and epigenetic alterations. Rare, stochastic, resistance-conferring genetic alterations have been found within a tumor cell population selected during drug treatment. See Sharma et al, Cell 141(1):69-80 (2010). The KDM5/JARID1 family of histone demethylases was found to play a role in cancer resistance. The KDM5/JARID1 family of demethylases in humans contains four members, KDM5A, KDM5B, KDM5C and KDM5D. KDM5 family members contain five conserved domains: JrnjN, ARID, JrnjC, PHD and a $C_5HC_2$ zinc finger. Amino acid sequences of KDM5A, KDM5B, KDM5C and KDM5D are known and are publicly available, e.g., see UniProtKB/Swiss-Prot (see e.g., KDM5A {e.g., P29375-1 and P29375-2), KDM5B {e.g., Q9UGL1-1 and Q9UGL1-2), KDM5C {e.g., P41229-1, P41229-2, P41229-3 and P41229-4) and KDM5D (e.g., Q9BY66-1, Q9BY66-2 and Q9BY66-3). There is currently a need for compounds that inhibit of KDM5 demethylases for treating hyperproliferative diseases, preventing drug resistance, and/or for improving the efficacy of other cancer treatments (e.g. targeted therapies, chemotherapies, and radiotherapies.

SUMMARY OF THE INVENTION

This invention provides compounds of the Formula I (represented as tautomers Ia and Ib):

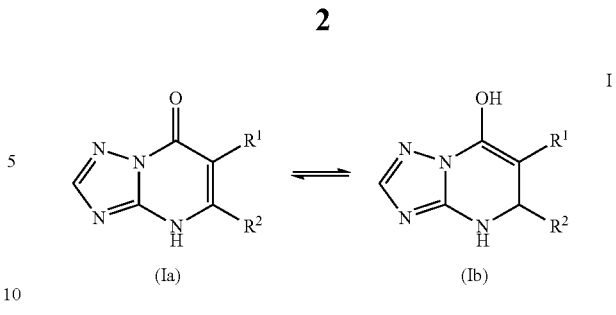

or the pharmaceutically acceptable salts, esters, and prodrugs thereof, which are KDM5 inhibitors. Reference hereinafter to "Formula I" includes reference to both Formulas Ia and Ib.

DETAILED DESCRIPTION OF THE INVENTION

One embodiment of the invention is compounds of formula I

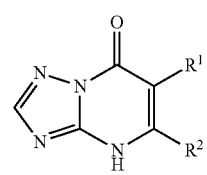

or a pharmaceutically acceptable salt thereof, wherein
$R^1$ is
  halogen,
  $C_1$-$C_6$ alkyl, unsubstituted or substituted with $CF_3$,
  $C_1$-$C_3$ alkylene-C(O)—O—$C_1$-$C_6$ alkyl,
  a 3-, 4-, 5- or 6 membered saturated carbocycle, or
  a 6-membered unsaturated carbocycle;
$R^2$ is
  halogen,
  $CF_3$,
  $C_1$-$C_6$ alkyl,
  $C_2$-$C_4$ alkenylene-O—$C_1$-$C_3$ alkyl,
  C(O)—O—$C_1$-$C_6$ alkyl,
  C(=$CH_2$)$C_1$-$C_4$ alkyl,
  $C_2$-$C_4$ alkenylene $C_6H_5$,
  $C_1$-$C_4$ alkylene $C_6H_5$,
  a 3-, 4-, 5- or 6 membered saturated carbocycle,
  a 6-membered unsaturated carbocycle, unsubstituted or mono-substituted or independently di-substituted with $R^3$,
  a 6-membered saturated heterocycle, unsubstituted, having 1 heteroatom which is O,
  a 5-membered unsaturated heterocycle having 1 or 2 heteroatoms independently selected from N, O and S, unsubstituted or independently mono- or di-substituted with $R^5$, or
  a 6-membered unsaturated heterocycle, having 1 or 2 heteroatoms independently selected from N and O, unsubstituted or independently mono-, di-, tri- or tetra-substituted with $R^4$, or
  an 8-, 9-, or 10-membered unsaturated bicyclic heterocycle having 1, 2 or 3 heteroatoms independently selected from N or O, unsubstituted or substituted with $R^6$;

R³ is
C₁-C₃ alkyl unsubstituted or mono- or independently di-substituted with a 6-membered saturated heterocycle having 1 or 2 heteroatoms independently selected from N and O, —C(O)OC₁-C₃ alkyl, —OH, —CF₃, and CN,
C₁-C₃ alkoxy,
halogen,
CN,
OH,
O—C₆H₅,
OC₁-C₃ alkyl,
C(O)OC₁-C₃ alkyl,
CF₃,
C(O)N(CH₃)₂,
NH₂,
NHSO₂C₁-C₃ alkyl,
NH(C₁-C₃ alkyl),
N(C₁-C₃ alkyl)(C₁-C₃ alkyl)
NHSO₂-cC₃H₅,
a 5- or 6-membered saturated heterocycle having 1 or 2 heteroatoms independently selected from N, O and S, wherein S is a dioxide, unsubstituted or substituted with C₁-C₃ alkyl, or
a 5- or 6-membered unsaturated heterocycle, unsubstituted or substituted with C₁-C₃ alkyl, having 1, 2 or 3 N atoms;

R⁴ is
halogen,
C₁-C₃ alkyl, unsubstituted or substituted with —OH,
CN,
CF₃,
cC₃H₅,
CF₂CH₂OH,
a 6-membered saturated heterocycle having 1 or 2 heteroatoms independently selected from N and O, or
a 5-membered unsaturated heterocycle having 2 N atoms;

R⁵ is
CF₃,
C₁-C₅ alkyl, unsubstituted or substituted with a 6-membered saturated heterocycle having 1 or 2 heteroatoms independently selected from N and O, a 6-membered unsaturated carbocycle, a 6-membered unsaturated heterocycle having 1 N atom, —OC₁-C₄ alkyl, —OH, —C(O)OH, a 5-membered unsaturated heterocycle having 1 S atom, cC₃H₅, —SO₂C₁-C₄ alkyl, —NHC₁-C₄ alkyl, or a 3-5-membered saturated carbocycle unsubstituted or substituted with F,
a 3-, 4-, 5- or 6-membered saturated carbocycle,
a 6-membered unsaturated carbocycle unsubstituted or substituted with halogen,
a 6-membered saturated heterocycle having 1 or 2 heteroatoms independently selected from N and O, or
a 5-membered unsaturated unsubstituted heterocycle having 1 or 2 N heteroatoms; and R⁶ is C₁-C₆ alkyl, cyclopropyl or =O.

In an embodiment of the invention,
R¹ is
Br, Cl, F, CH₃, CH₂CH₃, CH(CH₃)₂, C(CH₃)₃, CH₂C(O)OCH₃, CH₂CF₃,

[cyclobutyl structure], or [phenyl structure].

In an embodiment of the invention,
R² is
Cl, CH₃, CH₂CH₃, CH(CH₃)₂, CH₂CH₂CH₃, C(=CH₂)CH₂CH₂CH₃, CH=CHCH₂OCH₃, CF₃, C(O)OCH₂CH₃, CH=CHC₆H₅,

[various substituent structures shown]

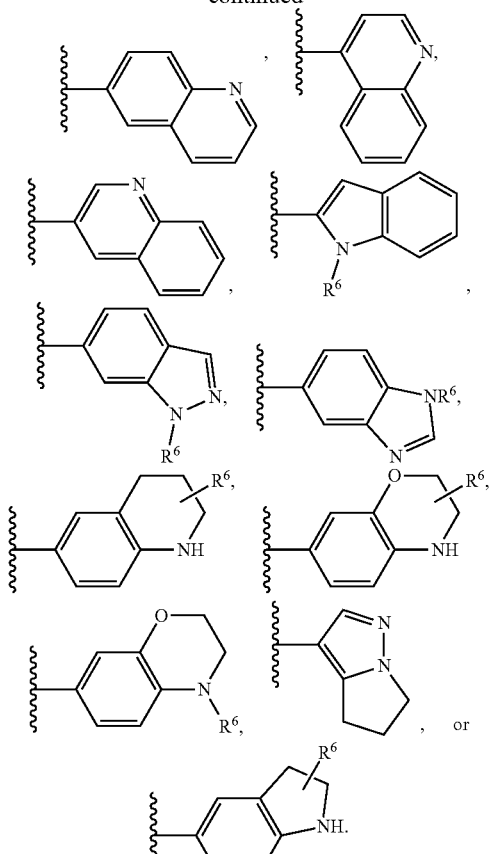
In an embodiment of the invention,
R² is
Cl, CH₃, CH₂CH₃, CH(CH₃)₂, CH₂CH₂CH₃, C(=CH₂)CH₂CH₂CH₃, CH=CHCH₂OCH₃, CF₃, C(O)OCH₂CH₃, CH=CHC₆H₅,
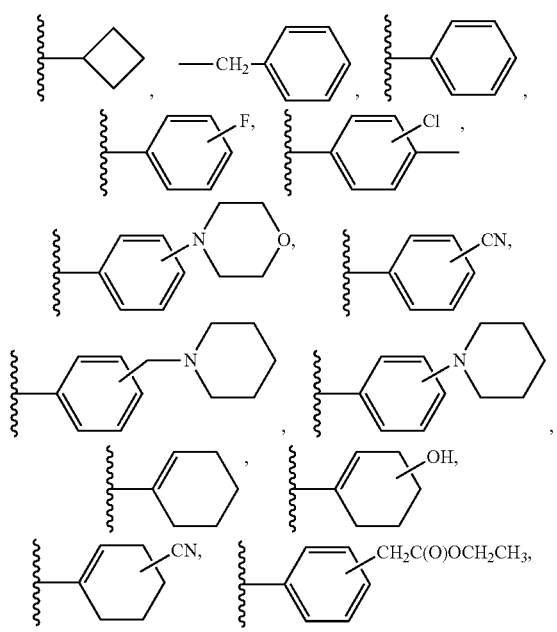
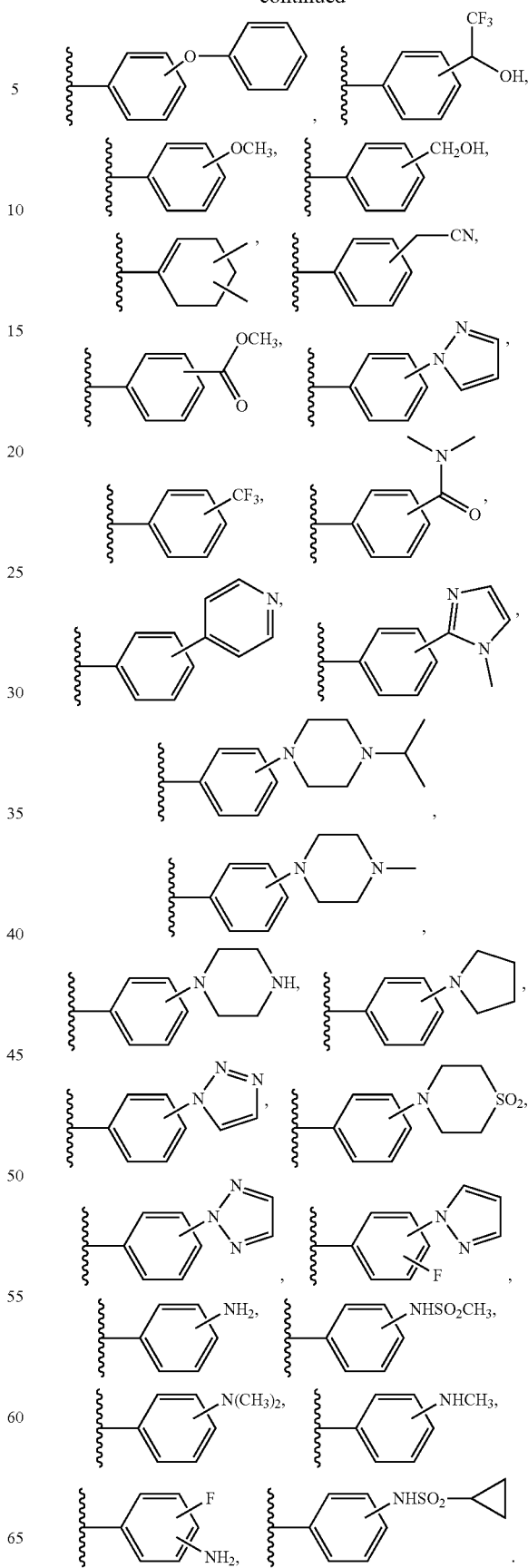

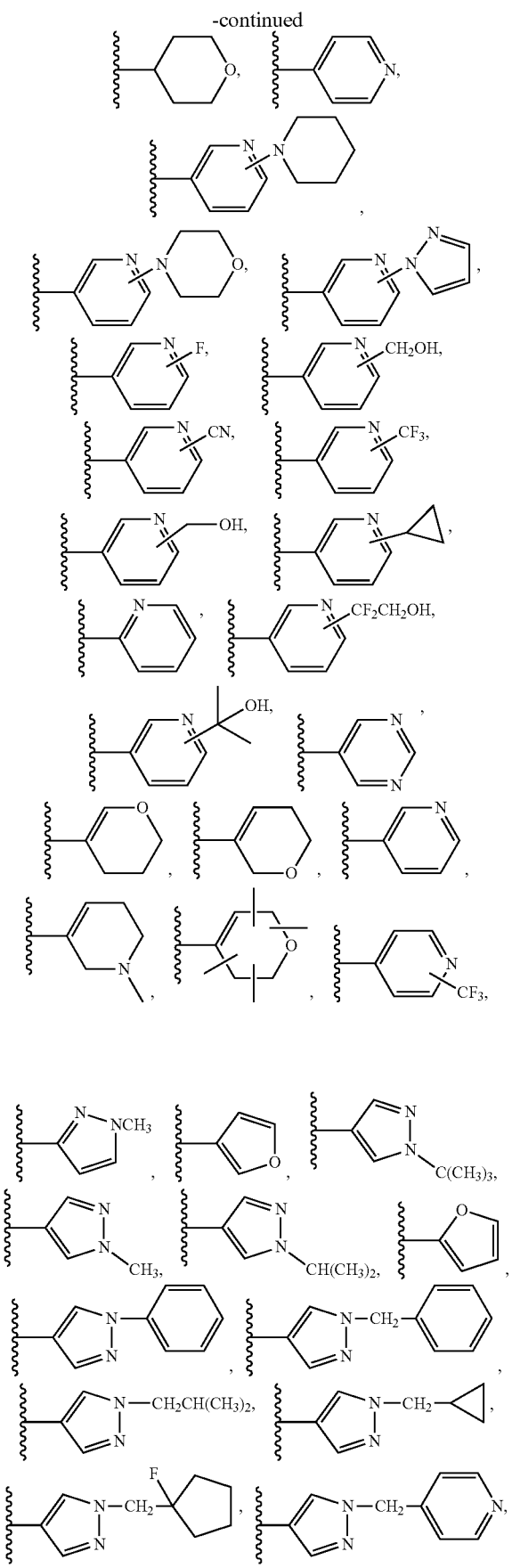
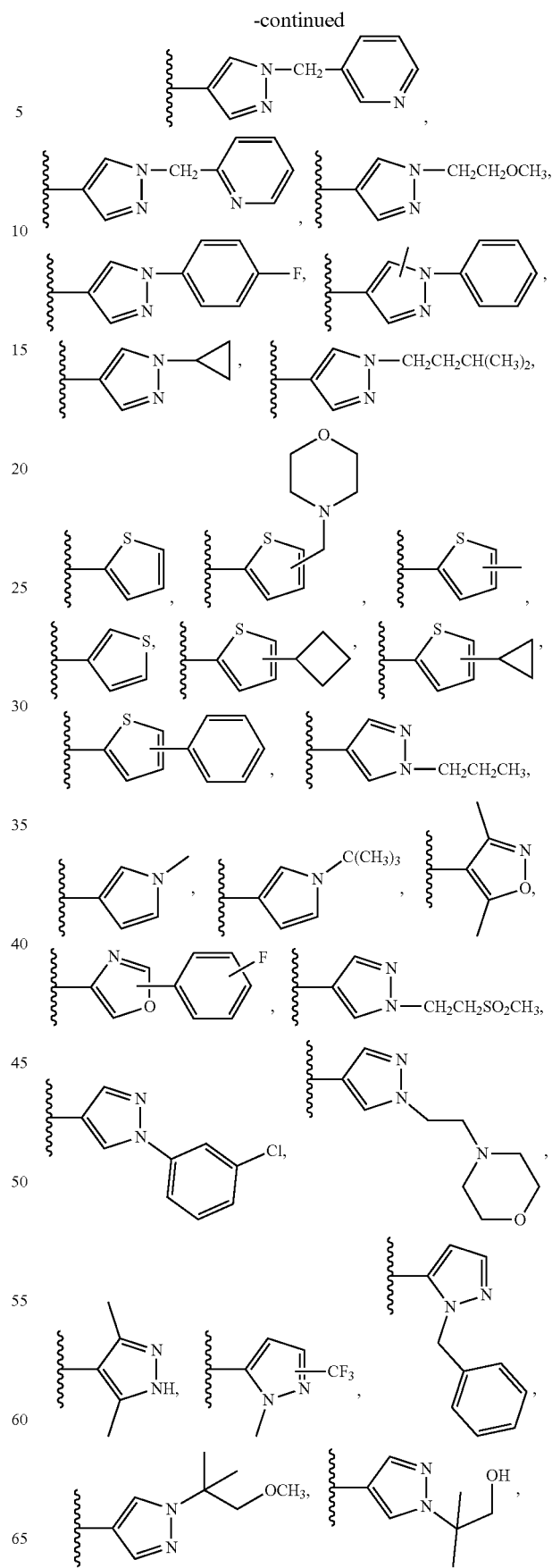

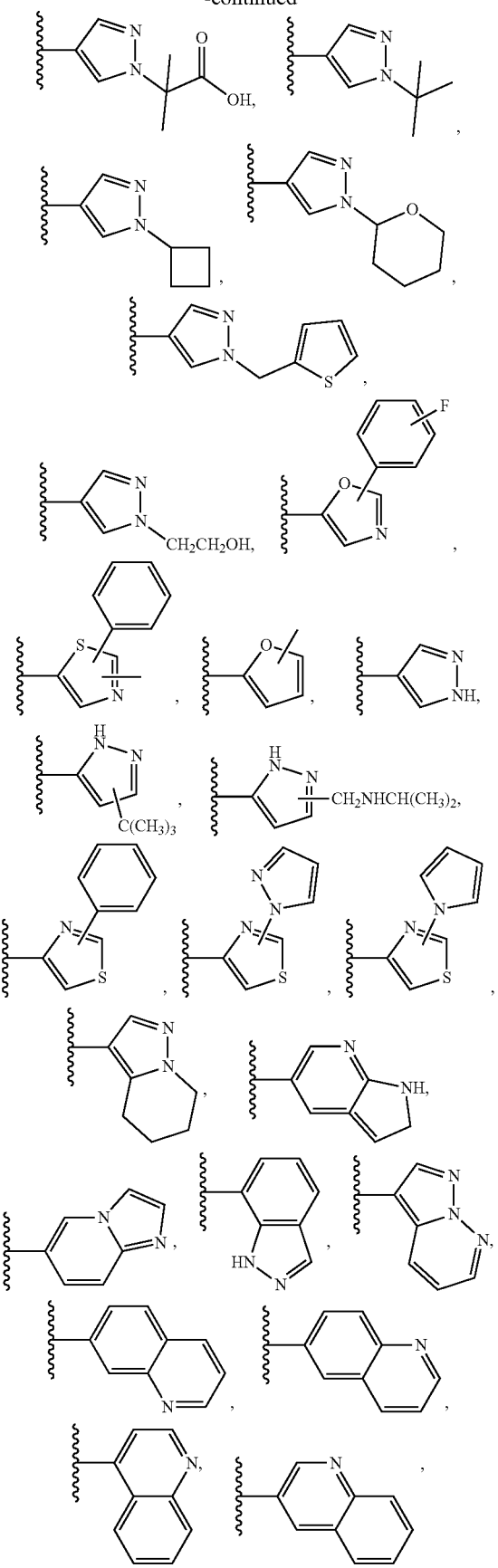
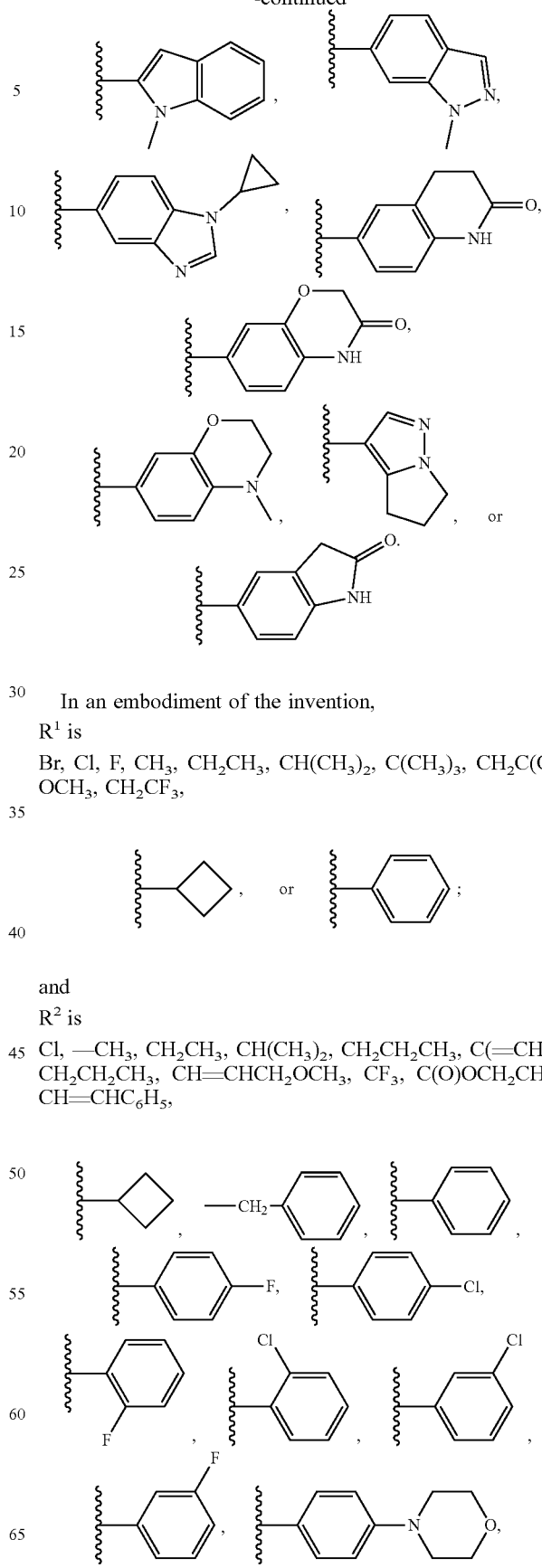
In an embodiment of the invention,
R[1] is
Br, Cl, F, $CH_3$, $CH_2CH_3$, $CH(CH_3)_2$, $C(CH_3)_3$, $CH_2C(O)OCH_3$, $CH_2CF_3$,
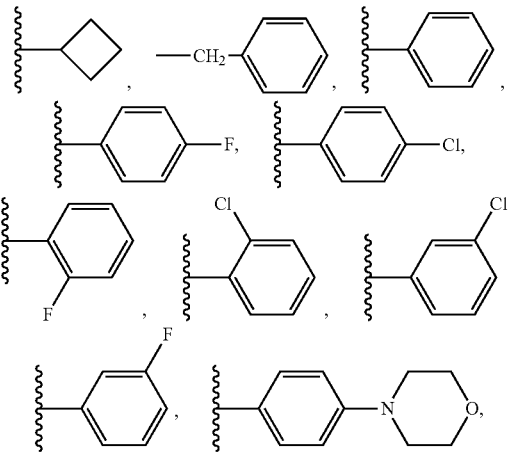
and
R[2] is
Cl, —$CH_3$, $CH_2CH_3$, $CH(CH_3)_2$, $CH_2CH_2CH_3$, $C(=CH_2)CH_2CH_2CH_3$, $CH_2CH_2CH_3$, $CH=CHCH_2OCH_3$, $CF_3$, $C(O)OCH_2CH_3$, $CH=CHC_6H_5$,

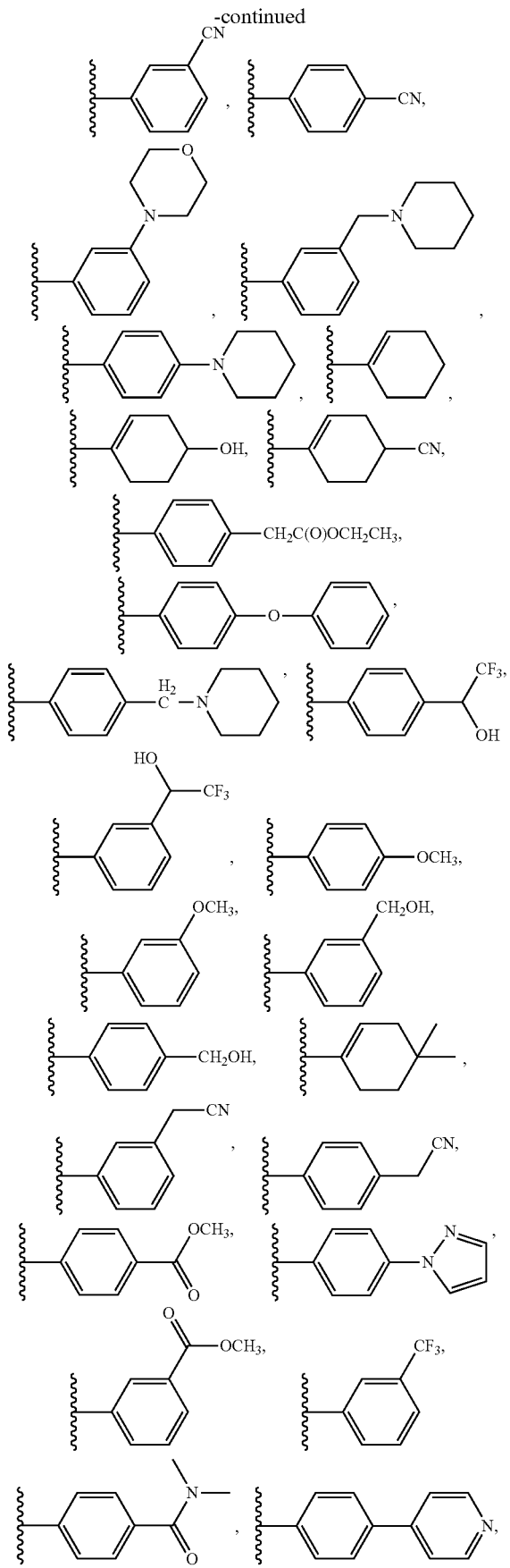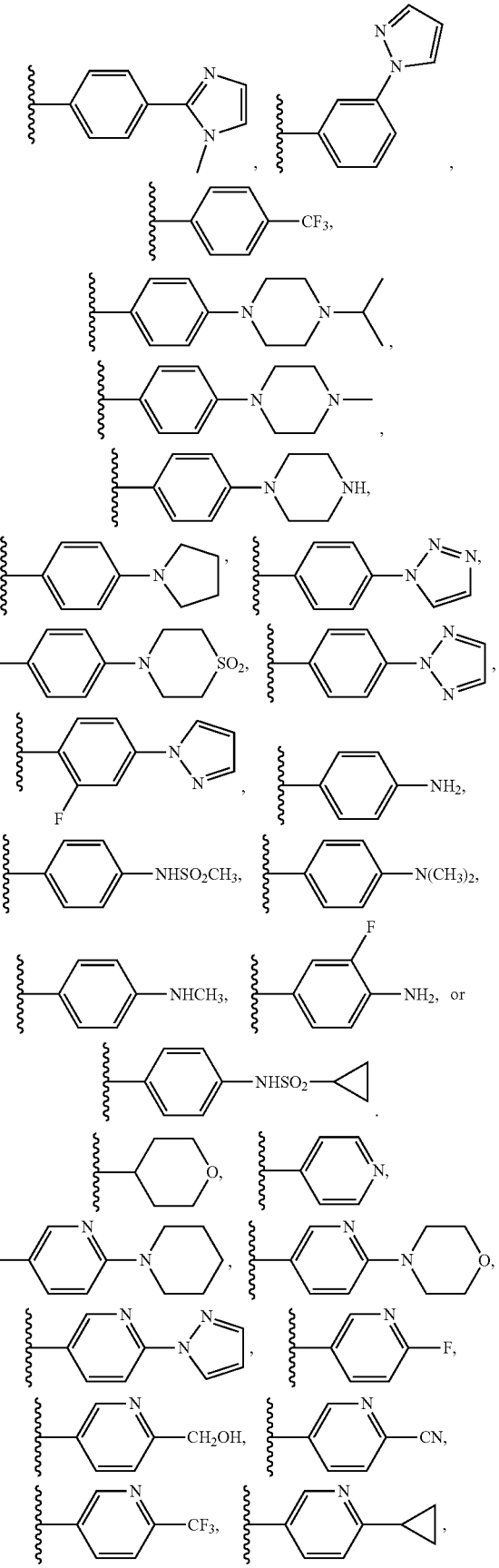

-continued
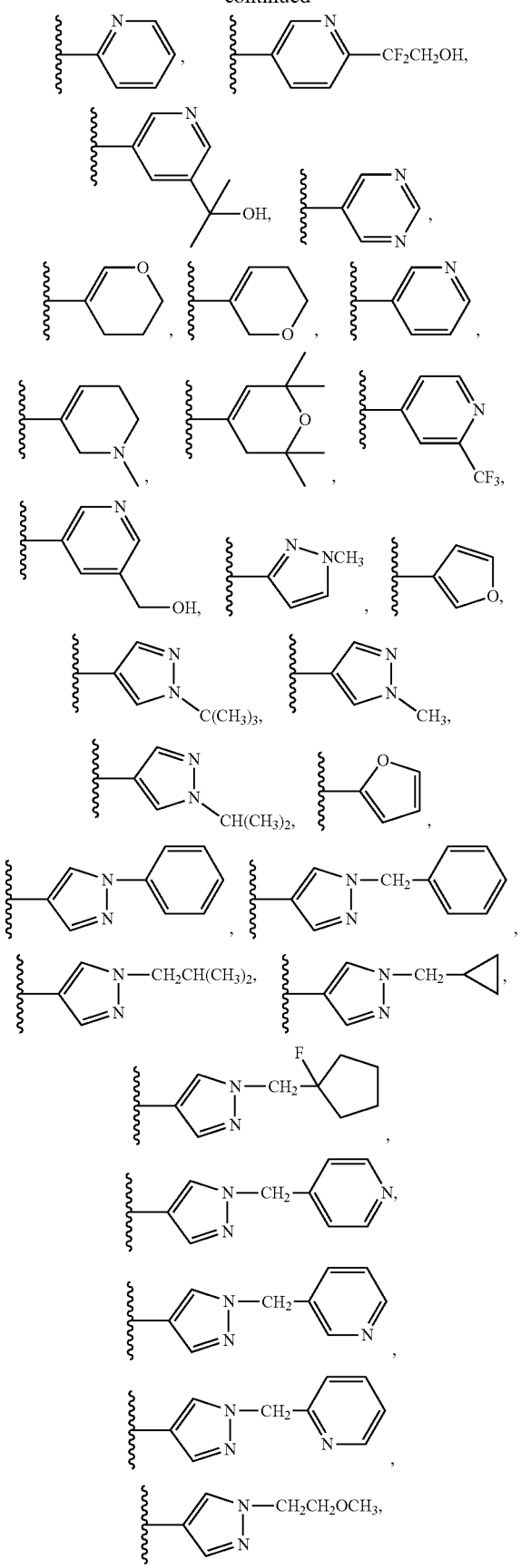
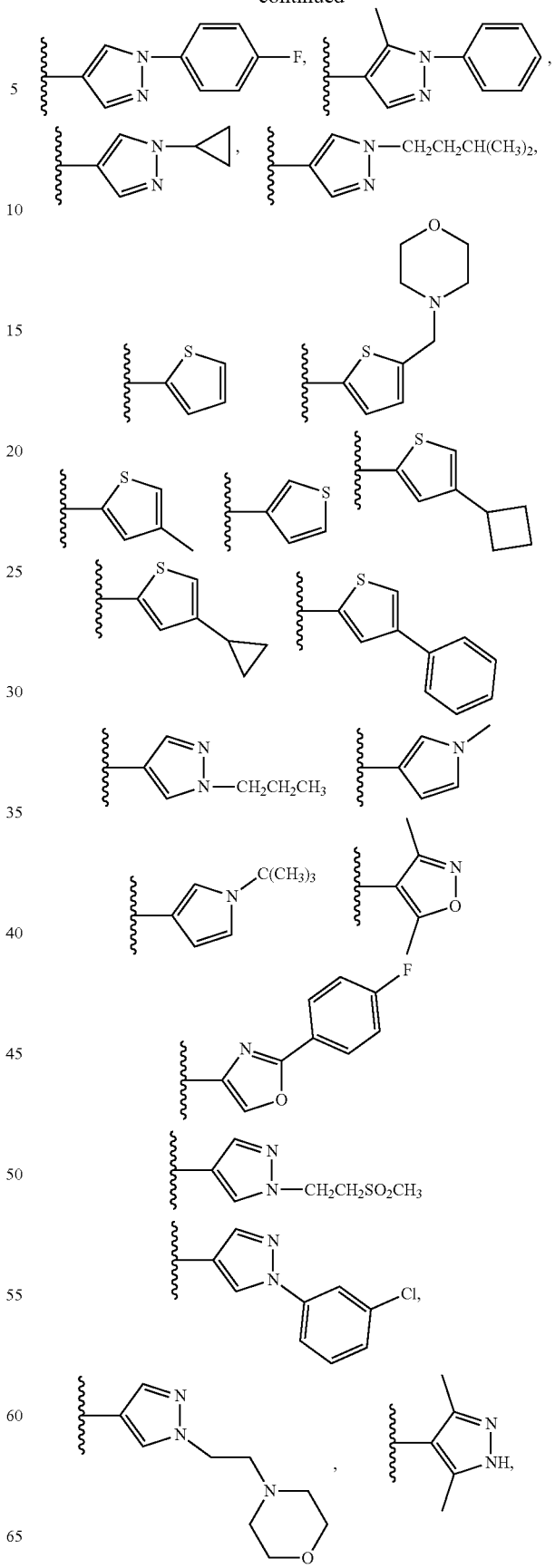

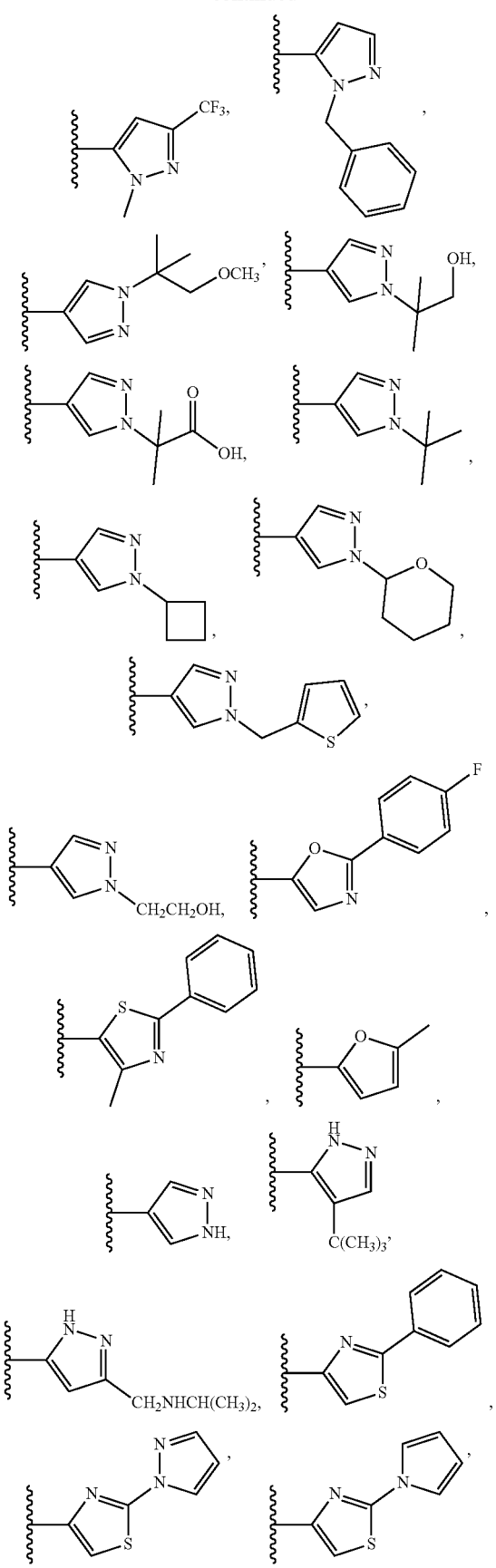
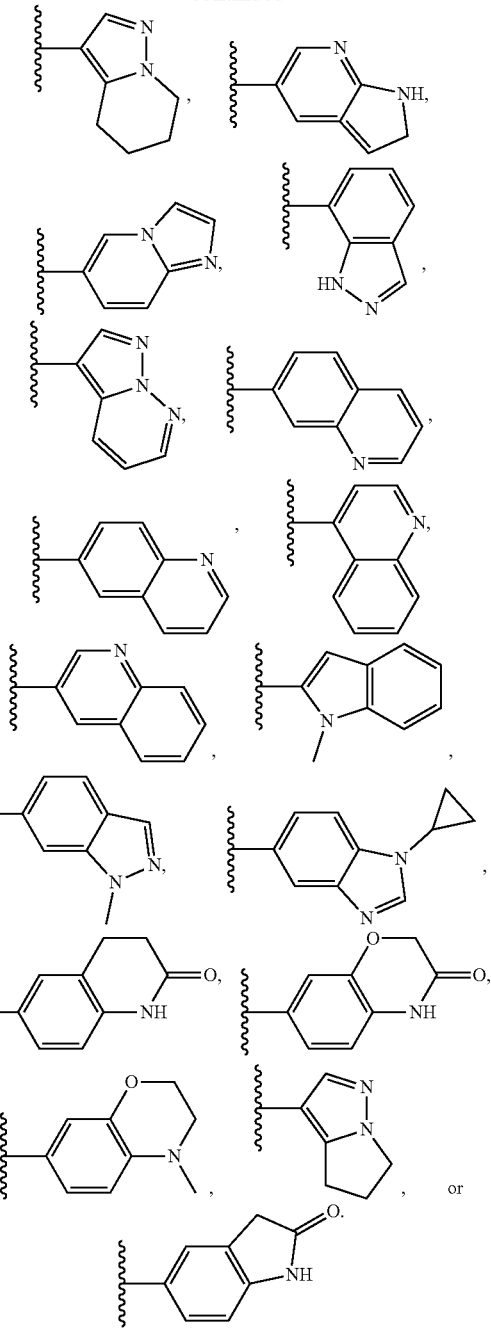

In an embodiment of the invention, the compound is
6-bromo-5-(1-(tert-butyl)-1H-pyrazol-4-yl)-[1,2,4]triazolo[1,5-a]pyrimidin-7(4H)-one,
6-ethyl-5-methyl-[1,2,4]triazolo[1,5-a]pyrimidin-7(4H)-one,
6-ethyl-7-methyl-[1,2,4]triazolo[4,3-a]pyrimidin-5(8H)-one,
5-(trifluoromethyl)[1,2,4]triazolo[1,5-a]pyrimidin-7(4H)-one,
5-methyl-[1,2,4]triazolo[1,5-a]pyrimidin-7(4H)-one,
5-phenyl-[1,2,4]triazolo[1,5-a]pyrimidin-7(4H)-one,
5-propyl[1,2,4]triazolo[1,5-a]pyrimidin-7(4H)-one,
methyl (5-methyl-7-oxo-4,7-dihydro[1,2,4]triazolo[1,5-a]pyrimidin-6-yl)acetate, 5-(4-fluorophenyl)[1,2,4]triazolo[1,5-a]pyrimidin-7(4H)-one,
5-ethyl-[1,2,4]triazolo[1,5-a]pyrimidin-7(4H)-one,
ethyl 6-chloro-7-oxo-4,7-dihydro[1,2,4]triazolo[1,5-a]pyrimidine-5-carboxylate,
ethyl 6-methyl-7-oxo-4,7-dihydro[1,2,4]triazolo[1,5-a]pyrimidine-5-carboxylate,
5-methyl-6-(1-methylethyl)[1,2,4]triazolo[1,5-a]pyrimidin-7(4H)-one,
5-(1-methyl-1H-pyrazol-3-yl)[1,2,4]triazolo[1,5-a]pyrimidin-7(4H)-one,
5-methyl-6-(trifluoromethyl)[1,2,4]triazolo[1,5-a]pyrimidin-7(4H)-one,
6-cyclobutyl-5-methyl-[1,2,4]triazolo[1,5-a]pyrimidin-7(4H)-one,
6-ethyl-5-(trifluoromethyl)[1,2,4]triazolo[1,5-a]pyrimidin-7(4H)-one,
6-fluoro-5-(trifluoromethyl)[1,2,4]triazolo[1,5-a]pyrimidin-7(4H)-one,
5-ethyl-6-methyl-[1,2,4]triazolo[1,5-a]pyrimidin-7(4H)-one,
5-[1-(1-methylethyl)-1H-pyrazol-4-yl][1,2,4]triazolo[1,5-a]pyrimidin-7(4H)-one,
5-(tetrahydro-2H-pyran-4-yl)[1,2,4]triazolo[1,5-a]pyrimidin-7(4H)-one,
5-furan-3-yl[1,2,4]triazolo[1,5-a]pyrimidin-7(4H)-one,
5-pyridin-4-yl[1,2,4]triazolo[1,5-a]pyrimidin-7(4H)-one,
5-pyridin-2-yl[1,2,4]triazolo[1,5-a]pyrimidin-7(4H)-one,
5-furan-2-yl[1,2,4]triazolo[1,5-a]pyrimidin-7(4H)-one,
6-fluoro-5-methyl-[1,2,4]triazolo[1,5-a]pyrimidin-7(4H)-one,
5-(4-chlorophenyl)[1,2,4]triazolo[1,5-a]pyrimidin-7(4H)-one,
5-(2-chlorophenyl)[1,2,4]triazolo[1,5-a]pyrimidin-7(4H)-one,
5-(2-fluorophenyl)[1,2,4]triazolo[1,5-a]pyrimidin-7(4H)-one,
5-(3-chlorophenyl)[1,2,4]triazolo[1,5-a]pyrimidin-7(4H)-one,
5-(3-fluorophenyl)[1,2,4]triazolo[1,5-a]pyrimidin-7(4H)-one,
5-(1-methyl-1H-pyrazol-4-yl)[1,2,4]triazolo[1,5-a]pyrimidin-7(4H)-one,
6-phenyl-5-propyl[1,2,4]triazolo[1,5-a]pyrimidin-7(4H)-one,
5-(1-methylethyl)[1,2,4]triazolo[1,5-a]pyrimidin-7(4H)-one,
6-ethyl-5-phenyl-[1,2,4]triazolo[1,5-a]pyrimidin-7(4H)-one,
6-(1-methylethyl)-5-phenyl-[1,2,4]triazolo[1,5-a]pyrimidin-7(4H)-one,
6-cyclobutyl-5-(4-fluorophenyl)[1,2,4]triazolo[1,5-a]pyrimidin-7(4H)-one,
6-cyclobutyl-5-[1-(1-methylethyl)-1H-pyrazol-4-yl][1,2,4]triazolo[1,5-a]pyrimidin-7(4H)-one,
6-(1-methylethyl)-5-(1-methyl-1H-pyrazol-4-yl)[1,2,4]triazolo[1,5-a]pyrimidin-7(4H)-one,
5-(1-tert-butyl-1H-pyrazol-4-yl)-6-(2,2,2-trifluoroethyl)[1,2,4]triazolo[1,5-a]pyrimidin-7(4H)-one,
5-chloro-6-isopropyl-[1,2,4]triazolo[1,5-a]pyrimidin-7(4H)-one,
6-(tert-butyl)-5-chloro-[1,2,4]triazolo[1,5-a]pyrimidin-7(4H)-one,
5-(1-(tert-butyl)-1H-pyrazol-4-yl)-6-isopropyl-[1,2,4]triazolo[1,5-a]pyrimidin-7(4H)-one,
5-(1-isopentyl-1H-pyrazol-4-yl)-6-isopropyl-[1,2,4]triazolo[1,5-a]pyrimidin-7(4H)-one,
6-isopropyl-5-(thiophen-2-yl)-[1,2,4]triazolo[1,5-a]pyrimidin-7(4H)-one,
5-(1-tert-butyl-1H-pyrazol-4-yl)-6-(1-methylethyl)[1,2,4]triazolo[1,5-a]pyrimidin-7(4H)-one,
5-[1-(3-methylbutyl)-1H-pyrazol-4-yl]-6-(1-methylethyl)[1,2,4]triazolo[1,5-a]pyrimidin-7(4H)-one,
6-(1-methylethyl)-5-thiophen-2-yl[1,2,4]triazolo[1,5-a]pyrimidin-7(4H)-one,
6-tert-butyl-5-(1-tert-butyl-1H-pyrazol-4-yl)[1,2,4]triazolo[1,5-a]pyrimidin-7(4H)-one,
6-tert-butyl-5-(4-fluorophenyl)[1,2,4]triazolo[1,5-a]pyrimidin-7(4H)-one,
6-tert-butyl-5-(1-methyl-1H-pyrazol-4-yl)[1,2,4]triazolo[1,5-a]pyrimidin-7(4H)-one,
6-tert-butyl-5-(1-phenyl-1H-pyrazol-4-yl)[1,2,4]triazolo[1,5-a]pyrimidin-7(4H)-one,
6-(1-methylethyl)-5-(1-phenyl-1H-pyrazol-4-yl)[1,2,4]triazolo[1,5-a]pyrimidin-7(4H)-one,
5-(1-benzyl-1H-pyrazol-4-yl)-6-(1-methylethyl)[1,2,4]triazolo[1,5-a]pyrimidin-7(4H)-one,
6-(1-methylethyl)-5-(4-morpholin-4-ylphenyl)[1,2,4]triazolo[1,5-a]pyrimidin-7(4H)-one,
5-(4-fluorophenyl)-6-(1-methylethyl)[1,2,4]triazolo[1,5-a]pyrimidin-7(4H)-one,
6-(1-methylethyl)-5-[1-(2-methylpropyl)-1H-pyrazol-4-yl][1,2,4]triazolo[1,5-a]pyrimidin-7(4H)-one,
5-{1-[(1-fluorocyclopentyl)methyl]-1H-pyrazol-4-yl}-6-(1-methylethyl)[1,2,4]triazolo[1,5-a]pyrimidin-7(4H)-one,
5-[1-(cyclopropylmethyl)-1H-pyrazol-4-yl]-6-(1-methylethyl)[1,2,4]triazolo[1,5-a]pyrimidin-7(4H)-one,
6-(1-methylethyl)-5-[1-(pyridin-4-ylmethyl)-1H-pyrazol-4-yl][1,2,4]triazolo[1,5-a]pyrimidin-7(4H)-one,
5-[1-(2-methoxyethyl)-1H-pyrazol-4-yl]-6-(1-methylethyl)[1,2,4]triazolo[1,5-a]pyrimidin-7(4H)-one,
5-[1-(4-fluorophenyl)-1H-pyrazol-4-yl]-6-(1-methylethyl)[1,2,4]triazolo[1,5-a]pyrimidin-7(4H)-one,
5-(1-cyclopropyl-1H-pyrazol-4-yl)-6-(1-methylethyl)[1,2,4]triazolo[1,5-a]pyrimidin-7(4H)-one,
5-(1-ethyl-1H-pyrazol-4-yl)-6-(1-methylethyl)[1,2,4]triazolo[1,5-a]pyrimidin-7(4H)-one,
6-(1-methylethyl)-5-[1-(1-methylethyl)-1H-pyrazol-4-yl][1,2,4]triazolo[1,5-a]pyrimidin-7(4H)-one,
6-(1-methylethyl)-5-(1-propyl-1H-pyrazol-4-yl)[1,2,4]triazolo[1,5-a]pyrimidin-7(4H)-one,
6-(1-methylethyl)-5-(1-methylidenebutyl)[1,2,4]triazolo[1,5-a]pyrimidin-7(4H)-one,
5-[(1E)-3-methoxyprop-1-en-1-yl]-6-(1-methylethyl)[1,2,4]triazolo[1,5-a]pyrimidin-7(4H)-one,
6-(1-methylethyl)-5-pyridin-4-yl[1,2,4]triazolo[1,5-a]pyrimidin-7(4H)-one,
6-(1-methylethyl)-5-pyridin-3-yl[1,2,4]triazolo[1,5-a]pyrimidin-7(4H)-one,
6-(1-methylethyl)-5-pyrimidin-5-yl[1,2,4]triazolo[1,5-a]pyrimidin-7(4H)-one,
6-(1-methylethyl)-5-(1-methyl-1H-pyrrol-3-yl)[1,2,4]triazolo[1,5-a]pyrimidin-7(4H)-one,
6-(1-methylethyl)-5-(5-methyl-1H-pyrazol-4-yl)[1,2,4]triazolo[1,5-a]pyrimidin-7(4H)-one,
5-cyclohex-1-en-1-yl-6-(1-methylethyl)[1,2,4]triazolo[1,5-a]pyrimidin-7(4H)-one,
5-(3,4-dihydro-2H-pyran-5-yl)-6-(1-methylethyl)[1,2,4]triazolo[1,5-a]pyrimidin-7(4H)-one,
5-(5,6-dihydro-2H-pyran-3-yl)-6-(1-methylethyl)[1,2,4]triazolo[1,5-a]pyrimidin-7(4H)-one,
5-(2-fluorophenyl)-6-(1-methylethyl)[1,2,4]triazolo[1,5-a]pyrimidin-7(4H)-one, 5-(3-fluorophenyl)-6-(1-methylethyl)[1,2,4]triazolo[1,5-a]pyrimidin-7(4H)-one,
5-(3,5-dimethylisoxazol-4-yl)-6-(1-methylethyl)[1,2,4]triazolo[1,5-a]pyrimidin-7(4H)-one,
6-(1-methylethyl)-5-(1-methyl-1,2,5,6-tetrahydropyridin-3-yl)[1,2,4]triazolo[1,5-a]pyrimidin-7(4H)-one,
5-(4-hydroxycyclohex-1-en-1-yl)-6-(1-methylethyl)[1,2,4]triazolo[1,5-a]pyrimidin-7(4H)-one,
3-[6-(1-methylethyl)-7-oxo-4,7-dihydro[1,2,4]triazolo[1,5-a]pyrimidin-5-yl]benzonitrile,
4-[6-(1-methylethyl)-7-oxo-4,7-dihydro[1,2,4]triazolo[1,5-a]pyrimidin-5-yl]benzonitrile,
6-(1-methylethyl)-5-[1-(pyridin-2-ylmethyl)-1H-pyrazol-4-yl][1,2,4]triazolo[1,5-a]pyrimidin-7(4H)-one,
6-(1-methylethyl)-5-[1-(pyridin-3-ylmethyl)-1H-pyrazol-4-yl][1,2,4]triazolo[1,5-a]pyrimidin-7(4H)-one,
6-(1-methylethyl)-5-(4-piperidin-1-ylphenyl)[1,2,4]triazolo[1,5-a]pyrimidin-7(4H)-one,
6-(1-methylethyl)-5-(3-piperidin-1-ylphenyl)[1,2,4]triazolo[1,5-a]pyrimidin-7(4H)-one,
5-[2-(4-fluorophenyl)-1,3-oxazol-4-yl]-6-(1-methylethyl)[1,2,4]triazolo[1,5-a]pyrimidin-7(4H)-one,
6-(1-methylethyl)-5-(3-morpholin-4-ylphenyl)[1,2,4]triazolo[1,5-a]pyrimidin-7(4H)-one,
ethyl {4-[6-(1-methylethyl)-7-oxo-4,7-dihydro[1,2,4]triazolo[1,5-a]pyrimidin-5-yl]phenyl}acetate,
6-(1-methylethyl)-5-(3-phenoxyphenyl)[1,2,4]triazolo[1,5-a]pyrimidin-7(4H)-one,
6-(1-methylethyl)-5-{1-[2-(methylsulfonyl)ethyl]-1H-pyrazol-4-yl}[1,2,4]triazolo[1,5-a]pyrimidin-7(4H)-one,
6-(1-methylethyl)-5-[4-(piperidin-1-ylmethyl)phenyl][1,2,4]triazolo[1,5-a]pyrimidin-7(4H)-one,
6-(1-methylethyl)-5-[3-(piperidin-1-ylmethyl)phenyl][1,2,4]triazolo[1,5-a]pyrimidin-7(4H)-one,
6-(1-methylethyl)-5-[4-(2,2,2-trifluoro-1-hydroxyethyl)phenyl][1,2,4]triazolo[1,5-a]pyrimidin-7(4H)-one,
5-[1-(3-chlorophenyl)-1H-pyrazol-4-yl]-6-(1-methylethyl)[1,2,4]triazolo[1,5-a]pyrimidin-7(4H)-one,
6-(1-methylethyl)-5-[1-(2-morpholin-4-ylethyl)-1H-pyrazol-4-yl][1,2,4]triazolo[1,5-a]pyrimidin-7(4H)-one,
6-(1-methylethyl)-5-(4,5,6,7-tetrahydropyrazolo[1,5-a]pyridin-3-yl)[1,2,4]triazolo[1,5-a]pyrimidin-7(4H)-one,
6-(1-methylethyl)-5-[3-(2,2,2-trifluoro-1-hydroxyethyl)phenyl][1,2,4]triazolo[1,5-a]pyrimidin-7(4H)-one,
6-(1-methylethyl)-5-[(E)-2-phenylethenyl][1,2,4]triazolo[1,5-a]pyrimidin-7(4H)-one,
4-[6-(1-methylethyl)-7-oxo-4,7-dihydro[1,2,4]triazolo[1,5-a]pyrimidin-5-yl]cyclohex-3-ene-1-carbonitrile,
5-(3-methoxyphenyl)-6-(1-methylethyl)[1,2,4]triazolo[1,5-a]pyrimidin-7(4H)-one,
5-(4-methoxyphenyl)-6-(1-methylethyl)[1,2,4]triazolo[1,5-a]pyrimidin-7(4H)-one, 5-[3-(hydroxymethyl)phenyl]-6-(1-methylethyl)[1,2,4]triazolo[1,5-a]pyrimidin-7(4H)-one,
5-[4-(hydroxymethyl)phenyl]-6-(1-methylethyl)[1,2,4]triazolo[1,5-a]pyrimidin-7(4H)-one,
6-(1-methylethyl)-5-(1,3,5-trimethyl-1H-pyrazol-4-yl)[1,2,4]triazolo[1,5-a]pyrimidin-7(4H)-one,
5-(4,4-dimethylcyclohex-1-en-1-yl)-6-(1-methylethyl)[1,2,4]triazolo[1,5-a]pyrimidin-7(4H)-one,
5-(4-chlorophenyl)-6-(1-methylethyl)[1,2,4]triazolo[1,5-a]pyrimidin-7(4H)-one,
5-(3-chlorophenyl)-6-(1-methylethyl)[1,2,4]triazolo[1,5-a]pyrimidin-7(4H)-one,
5-(2-chlorophenyl)-6-(1-methylethyl)[1,2,4]triazolo[1,5-a]pyrimidin-7(4H)-one,
{3-[6-(1-methylethyl)-7-oxo-4,7-dihydro[1,2,4]triazolo[1,5-a]pyrimidin-5-yl]phenyl}acetonitrile,
{4-[6-(1-methylethyl)-7-oxo-4,7-dihydro[1,2,4]triazolo[1,5-a]pyrimidin-5-yl]phenyl}acetonitrile,
6-(1-methylethyl)-5-(1H-pyrrolo[2,3-b]pyridin-5-yl)[1,2,4]triazolo[1,5-a]pyrimidin-7(4H)-one,
5-imidazo[1,2-a]pyridin-6-yl-6-(1-methylethyl)[1,2,4]triazolo[1,5-a]pyrimidin-7(4H)-one,
5-(1H-benzimidazol-6-yl)-6-(1-methylethyl)[1,2,4]triazolo[1,5-a]pyrimidin-7(4H)-one,
5-(1H-indazol-4-yl)-6-(1-methylethyl)[1,2,4]triazolo[1,5-a]pyrimidin-7(4H)-one,
6-(1-methylethyl)-5-pyrazolo[1,5-b]pyridazin-3-yl[1,2,4]triazolo[1,5-a]pyrimidin-7(4H)-one,
6-(1-methylethyl)-5-quinolin-7-yl[1,2,4]triazolo[1,5-a]pyrimidin-7(4H)-one,
6-(1-methylethyl)-5-quinolin-6-yl[1,2,4]triazolo[1,5-a]pyrimidin-7(4H)-one,
6-(1-methylethyl)-5-quinolin-4-yl[1,2,4]triazolo[1,5-a]pyrimidin-7(4H)-one,
6-(1-methylethyl)-5-quinolin-3-yl[1,2,4]triazolo[1,5-a]pyrimidin-7(4H)-one,
6-(1-methylethyl)-5-(1-methyl-1H-indol-2-yl)[1,2,4]triazolo[1,5-a]pyrimidin-7(4H)-one,
6-(1-methylethyl)-5-(1-methyl-1H-indazol-5-yl)[1,2,4]triazolo[1,5-a]pyrimidin-7(4H)-one,
methyl 4-[6-(1-methylethyl)-7-oxo-4,7-dihydro[1,2,4]triazolo[1,5-a]pyrimidin-5-yl]benzoate,
methyl 3-[6-(1-methylethyl)-7-oxo-4,7-dihydro[1,2,4]triazolo[1,5-a]pyrimidin-5-yl]benzoate,
6-(1-methylethyl)-5-(2,2,6,6-tetramethyl-3,6-dihydro-2H-pyran-4-yl)[1,2,4]triazolo[1,5-a]pyrimidin-7(4H)-one,
6-(1-methylethyl)-5-[4-(1H-pyrazol-1-yl)phenyl][1,2,4]triazolo[1,5-a]pyrimidin-7(4H)-one,
6-(1-methylethyl)-5-[3-(1H-pyrazol-1-yl)phenyl][1,2,4]triazolo[1,5-a]pyrimidin-7(4H)-one,
6-(1-methylethyl)-5-[4-(trifluoromethyl)phenyl][1,2,4]triazolo[1,5-a]pyrimidin-7(4H)-one,
6-(1-methylethyl)-5-[3-(trifluoromethyl)phenyl][1,2,4]triazolo[1,5-a]pyrimidin-7(4H)-one,
N,N-dimethyl-4-[6-(1-methylethyl)-7-oxo-4,7-dihydro[1,2,4]triazolo[1,5-a]pyrimidin-5-yl]benzamide,
6-(1-methylethyl)-5-[1-methyl-3-(trifluoromethyl)-1H-pyrazol-5-yl][1,2,4]triazolo[1,5-a]pyrimidin-7(4H)-one,
6-(1-methylethyl)-5-(4-pyridin-4-ylphenyl)[1,2,4]triazolo[1,5-a]pyrimidin-7(4H)-one,
5-(1-cyclopropyl-1H-benzimidazol-6-yl)-6-(1-methylethyl)[1,2,4]triazolo[1,5-a]pyrimidin-7(4H)-one,
6-(1-methylethyl)-5-[4-(1-methyl-1H-imidazol-2-yl)phenyl][1,2,4]triazolo[1,5-a]pyrimidin-7(4H)-one,
5-(1-benzyl-1H-pyrazol-5-yl)-6-(1-methylethyl)[1,2,4]triazolo[1,5-a]pyrimidin-7(4H)-one,
5-[1-(2-methoxy-1,1-dimethylethyl)-1H-pyrazol-4-yl]-6-(1-methylethyl)[1,2,4]triazolo[1,5-a]pyrimidin-7(4H)-one,
6-(1-methylethyl)-5-{4-[4-(1-methylethyl)piperazin-1-yl]phenyl}[1,2,4]triazolo[1,5-a]pyrimidin-7(4H)-one,
6-(1-methylethyl)-5-(4-pyrrolidin-1-ylphenyl)[1,2,4]triazolo[1,5-a]pyrimidin-7(4H)-one,
6-(1-methylethyl)-5-[4-(1H-1,2,3-triazol-1-yl)phenyl][1,2,4]triazolo[1,5-a]pyrimidin-7(4H)-one,
5-[4-(1,1-dioxidothiomorpholin-4-yl)phenyl]-6-(1-methylethyl)[1,2,4]triazolo[1,5-a]pyrimidin-7(4H)-one,
6-(1-methylethyl)-5-[4-(2H-1,2,3-triazol-2-yl)phenyl][1,2,4]triazolo[1,5-a]pyrimidin-7(4H)-one,
5-[2-fluoro-4-(1H-pyrazol-1-yl)phenyl]-6-(1-methylethyl)[1,2,4]triazolo[1,5-a]pyrimidin-7(4H)-one, 5-(4-aminophenyl)-6-(1-methylethyl)[1,2,4]triazolo[1,5-a]pyrimidin-7(4H)-one,
N-{4-[6-(1-methylethyl)-7-oxo-4,7-dihydro[1,2,4]triazolo[1,5-a]pyrimidin-5-yl]phenyl}methanesulfonamide,
6-[6-(1-methylethyl)-7-oxo-4,7-dihydro[1,2,4]triazolo[1,5-a]pyrimidin-5-yl]-3,4-dihydroquinolin-2(1H)-one,
7-[6-(1-methylethyl)-7-oxo-4,7-dihydro[1,2,4]triazolo[1,5-a]pyrimidin-5-yl]-2H-1,4-benzoxazin-3(4H)-one,
5-[4-(dimethylamino)phenyl]-6-(1-methylethyl)[1,2,4]triazolo[1,5-a]pyrimidin-7(4H)-one,
5-[4-(methylamino)phenyl]-6-(1-methylethyl)[1,2,4]triazolo[1,5-a]pyrimidin-7(4H)-one,
5-(4-methyl-3,4-dihydro-2H-1,4-benzoxazin-7-yl)-6-(1-methylethyl)[1,2,4]triazolo[1,5-a]pyrimidin-7(4H)-one,
6-(1-methylethyl)-5-[4-(4-methylpiperazin-1-yl)phenyl][1,2,4]triazolo[1,5-a]pyrimidin-7(4H)-one,
5-[1-(2-hydroxy-1,1-dimethylethyl)-1H-pyrazol-4-yl]-6-(1-methylethyl)[1,2,4]triazolo[1,5-a]pyrimidin-7(4H)-one,
6-(1-methylethyl)-5-[5-(morpholin-4-ylmethyl)thiophen-2-yl][1,2,4]triazolo[1,5-a]pyrimidin-7(4H)-one,
5-(1-cyclobutyl-1H-pyrazol-4-yl)-6-(1-methylethyl)[1,2,4]triazolo[1,5-a]pyrimidin-7(4H)-one,
6-(1-methylethyl)-5-[1-(thiophen-2-ylmethyl)-1H-pyrazol-4-yl][1,2,4]triazolo[1,5-a]pyrimidin-7(4H)-one,
5-[1-(2-hydroxyethyl)-1H-pyrazol-4-yl]-6-(1-methylethyl)[1,2,4]triazolo[1,5-a]pyrimidin-7(4H)-one,
5-(5,6-dihydro-4H-pyrrolo[1,2-b]pyrazol-3-yl)-6-(1-methylethyl)[1,2,4]triazolo[1,5-a]pyrimidin-7(4H)-one,
5-[2-(4-fluorophenyl)-1,3-oxazol-5-yl]-6-(1-methylethyl)[1,2,4]triazolo[1,5-a]pyrimidin-7(4H)-one,
6-(1-methylethyl)-5-(5-methyl-1-phenyl-1H-pyrazol-4-yl)[1,2,4]triazolo[1,5-a]pyrimidin-7(4H)-one,
6-(1-methylethyl)-5-(4-methylthiophen-2-yl)[1,2,4]triazolo[1,5-a]pyrimidin-7(4H)-one,
6-(1-methylethyl)-5-(4-methyl-2-phenyl-1,3-thiazol-5-yl)[1,2,4]triazolo[1,5-a]pyrimidin-7(4H)-one,
6-(1-methylethyl)-5-(5-methylfuran-2-yl)[1,2,4]triazolo[1,5-a]pyrimidin-7(4H)-one,
6-(1-methylethyl)-5-(4-piperazin-1-ylphenyl)[1,2,4]triazolo[1,5-a]pyrimidin-7(4H)-one,
5-(4-amino-3-fluorophenyl)-6-(1-methylethyl)[1,2,4]triazolo[1,5-a]pyrimidin-7(4H)-one,
6-(1-methylethyl)-5-[2-(trifluoromethyl)pyridin-4-yl][1,2,4]triazolo[1,5-a]pyrimidin-7(4H)-one,
5-[5-(1-hydroxy-1-methylethyl)pyridin-3-yl]-6-(1-methylethyl)[1,2,4]triazolo[1,5-a]pyrimidin-7(4H)-one,
6-(1-methylethyl)-5-(1H-pyrazol-4-yl)[1,2,4]triazolo[1,5-a]pyrimidin-7(4H)-one,
6-(1-methylethyl)-5-(2-oxo-2,3-dihydro-1H-indol-5-yl)[1,2,4]triazolo[1,5-a]pyrimidin-7(4H)-one,
N-{4-[6-(1-methylethyl)-7-oxo-4,7-dihydro[1,2,4]triazolo[1,5-a]pyrimidin-5-yl]phenyl}cyclopropanesulfonamide,
6-(1-methylethyl)-5-[1-(tetrahydro-2H-pyran-2-yl)-1H-pyrazol-4-yl][1,2,4]triazolo[1,5-a]pyrimidin-7(4H)-one,
6-(1-methylethyl)-5-(6-piperidin-1-ylpyridin-3-yl)[1,2,4]triazolo[1,5-a]pyrimidin-7(4H)-one,
6-(1-methylethyl)-5-(6-morpholin-4-ylpyridin-3-yl)[1,2,4]triazolo[1,5-a]pyrimidin-7(4H)-one,
6-(1-methylethyl)-5-[6-(1H-pyrazol-1-yl)pyridin-3-yl][1,2,4]triazolo[1,5-a]pyrimidin-7(4H)-one,
5-(6-fluoropyridin-3-yl)-6-(1-methylethyl)[1,2,4]triazolo[1,5-a]pyrimidin-7(4H)-one,
5-[6-(hydroxymethyl)pyridin-3-yl]-6-(1-methylethyl)[1,2,4]triazolo[1,5-a]pyrimidin-7(4H)-one,
5-[6-(1-methylethyl)-7-oxo-4,7-dihydro[1,2,4]triazolo[1,5-a]pyrimidin-5-yl]pyridine-2-carbonitrile,
6-(1-methylethyl)-5-[6-(trifluoromethyl)pyridin-3-yl][1,2,4]triazolo[1,5-a]pyrimidin-7(4H)-one,
5-(6-cyclopropylpyridin-3-yl)-6-(1-methylethyl)[1,2,4]triazolo[1,5-a]pyrimidin-7(4H)-one,
5-(1-tert-butyl-1H-pyrrol-3-yl)-6-(1-methylethyl)[1,2,4]triazolo[1,5-a]pyrimidin-7(4H)-one,
5-(3-tert-butyl-1H-pyrazol-5-yl)-6-(1-methylethyl)[1,2,4]triazolo[1,5-a]pyrimidin-7(4H)-one,
6-(1-methylethyl)-5-(2-phenyl-1,3-thiazol-4-yl)[1,2,4]triazolo[1,5-a]pyrimidin-7(4H)-one,
6-(1-methylethyl)-5-[2-(1H-pyrazol-1-yl)-1,3-thiazol-4-yl][1,2,4]triazolo[1,5-a]pyrimidin-7(4H)-one,
6-(1-methylethyl)-5-thiophen-3-yl[1,2,4]triazolo[1,5-a]pyrimidin-7(4H)-one,
6-(1-methylethyl)-5-(1,3-oxazol-5-yl)[1,2,4]triazolo[1,5-a]pyrimidin-7(4H)-one,
6-(1-methylethyl)-5-[2-(1H-pyrrol-1-yl)-1,3-thiazol-4-yl][1,2,4]triazolo[1,5-a]pyrimidin-7(4H)-one,
6-(1-methylethyl)-5-[4-(1-methylethyl)thiophen-2-yl][1,2,4]triazolo[1,5-a]pyrimidin-7(4H)-one,
5-(4-cyclobutylthiophen-2-yl)-6-(1-methylethyl)[1,2,4]triazolo[1,5-a]pyrimidin-7(4H)-one,
5-(4-cyclopropylthiophen-2-yl)-6-(1-methylethyl)[1,2,4]triazolo[1,5-a]pyrimidin-7(4H)-one,
6-(1-methylethyl)-5-(4-phenylthiophen-2-yl)[1,2,4]triazolo[1,5-a]pyrimidin-7(4H)-one,
5-(6-(1,1-difluoro-2-hydroxyethyl)pyridin-3-yl)-6-isopropyl-[1,2,4]triazolo[1,5-a]pyrimidin-7(4H)-one,
5-[6-(1,1-difluoro-2-hydroxyethyl)pyridin-3-yl]-6-(1-methylethyl)[1,2,4]triazolo[1,5-a]pyrimidin-7(4H)-one,
5-[5-(hydroxymethyl)pyridin-3-yl]-6-(1-methylethyl)[1,2,4]triazolo[1,5-a]pyrimidin-7(4H)-one,
6-isopropyl-5-(3-((isopropylamino)methyl)-1H-pyrazol-5-yl)-[1,2,4]triazolo[1,5-a]pyrimidin-7(4H)-one,
2-(4-(6-isopropyl-7-oxo-4,7-dihydro-[1,2,4]triazolo[1,5-a]pyrimidin-5-yl)-1H-pyrazol-1-yl)-2-methylpropanoic acid, or
5-(1-(tert-butyl)-1H-pyrazol-4-yl)-6-cyclopropyl-[1,2,4]triazolo[1,5-a]pyrimidin-7(4H)-one.

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient) for treating cancer. The term "antineoplastic agent" means a drug (medicament or pharmaceutically active ingredient) for treating cancer (i.e., a chemotherapeutic agent). The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "compound" with reference to the antineoplastic agents, includes the agents that are antibodies. The term "consecutively" means one following the other. The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of the invention) is that amount which results in the reduction in ERK (ERK2) activity and phosphorylation. The reduction in ERK activity may be determined by the analysis of pharmacodynamic markers such as phosphorylated RSK1,2 using techniques well known in the art. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The invention also provides a pharmaceutical composition comprising an effective amount of at least one compound of Formula I and a pharmaceutically acceptable carrier. The invention also provides a pharmaceutical composition comprising an effective amount of at least one compound of Formula I and an effective amount of at least one other pharmaceutically active ingredient (such as, for example, a chemotherapeutic agent), and a pharmaceutically acceptable carrier.

The invention also provides a method of inhibiting ERK2 in a patient in need of such treatment comprising administering to said patient an effective amount of at least one compound of Formula I. The invention also provides a method for treating cancer in a patient in need of such treatment, said method comprising administering to said patient an effective amount of at least one compound of Formula I. The invention also provides a method for treating cancer in a patient in need of such treatment, said method comprising administering to said patient an effective amount of at least one compound of Formula I, in combination with an effective amount of at least one chemotherapeutic agent. The methods of the invention include the administration of a pharmaceutical composition comprising at least one compound of the invention and a pharmaceutically acceptable carrier. The invention also provides any of the above methods of treating cancer wherein the cancer is colorectal. The invention also provides any of the above methods of treating cancer wherein the cancer is melanoma. The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of the invention is directed to a method of treating cancer in a patient in need of such treatment, said method comprising administering an effective amount of a compound of Formula I. Another example of the invention is directed to a method of treating cancer in a patient in need of such treatment, said method comprising administering to said patient an effective amount of a compound of Formula I, and an effective amount of at least one chemotherapeutic agent.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians' Desk Reference, $56^{th}$ Edition, 2002 (published by Medical Economics company, Inc. Montvale, N.J. 07645-1742), the Physicians' Desk Reference, $57^{th}$ Edition, 2003 (published by Thompson PDR, Montvale, N.J. 07645-1742), the Physicians' Desk Reference, $60^{th}$ Edition, 2006 (published by Thompson PDR, Montvale, N.J. 07645-1742), and the Physicians' Desk Reference, $64^{th}$ Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MM scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of Formula I, or a pharmaceutically acceptable salt thereof, to said patient. Another example of the invention is directed to a method of treating colo-rectal cancer in a patient in need of such treatment, said method comprising administering to said patient an effective amount of a compound of Formula I, or a pharmaceutically acceptable salt thereof, and an effective amount of at least one chemotherapeutic agent.

In one example of the invention the cancer treated is melanoma. Thus, another example of the invention is directed to a method of treating melanoma in a patient in need of such treatment, said method comprising administering an effective amount of a compound of Formula I, or a pharmaceutically acceptable salt thereof, to said patient. Another example of the invention is directed to a method of treating melanoma in a patient in need of such treatment, said method comprising administering to said patient an effective amount of a compound of Formula I, or a pharmaceutically acceptable salt thereof, and an effective amount of at least one chemotherapeutic agent.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V.T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

PD-1 inhibitors include pembrolizumab (lambrolizumab), nivolumab and MPDL3280A. PD-L1 inhibitors include atezolizumab, avelumab, and durvalumab.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydrooxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, Na6-[4-deoxy-4-[N2-[2(E),4(E)-tetradecadienoyl]glycylamino]-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273, 995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475

(1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734188, 60/652737, 60/670469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of the specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of the specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344, 991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the αvβ5 integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another example of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an example, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, per-sulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with unsolvated and anhydrous forms.

Reference to the compounds of the invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or CH₃ or a symbol that is an extended bond as the terminal group, e.g. ⸺, ethyl may be represented by "Et" or CH₂CH₃, propyl may be represented by "Pr" or CH₂CH₂CH₃, butyl may be represented by "Bu" or CH₂CH₂CH₂CH₃, etc. "C$_{1-4}$ alkyl" (or "C$_1$-C$_4$ alkyl") for example, means linear or branched chain alkyl groups, including all isomers, having the specified number of carbon atoms. For example, the structures

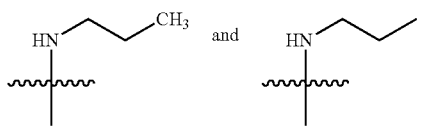

have equivalent meanings. C$_{1-4}$ alkyl includes n-, iso-, sec- and t-butyl, n- and isopropyl, ethyl and methyl. If no number is specified, 1-4 carbon atoms are intended for linear or branched alkyl groups. A "cycloalkyl" group is a ring of saturated aliphatic hydrocarbons having the specified number of carbon atoms. For example, C$_{3-8}$ cycloalkyl (or "C$_3$-C$_8$ cycloalkyl") is a saturated ring having 3-8 carbon atoms, e.g., cyclopropyl (cC₃H₅), cyclobutyl (cC₄H₇), cyclopentyl (cC₅H₉), etc.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of the invention which results in conversion in vivo to a compound within the scope of the invention is also within the scope of the invention. For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as prodrugs which can be hydrolyzed back to an acid (or —COO— depending on the pH of the fluid or tissue where conversion takes place) or hydroxy form particularly in vivo and as such are encompassed within the scope of the invention. Examples of pharmaceutically acceptable pro-drug modifications include, but are not limited to, —C$_{1-6}$alkyl esters and —C$_{1-6}$alkyl substituted with phenyl esters.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Alkyl groups may be unsubstituted, or substituted with 1 to 3 substituents on any one or more carbon atoms, with halogen, C$_1$-C$_{20}$ alkyl, CF₃, NH₂, —NH(C$_1$-C$_6$ alkyl), —N(C$_1$-C$_6$ alkyl)₂, NO₂, oxo, CN, N₃, —OH, —O(C$_1$-C$_6$ alkyl), C$_3$-C$_{10}$ cycloalkyl, C$_2$-C$_6$ alkenyl, C$_2$-C$_6$ alkynyl, (C$_1$-C$_6$ alkyl)S(O)$_{0-2}$—, HS(O)$_{0-2}$—, (C$_1$-C$_6$ alkyl)S(O)$_{0-2}$(C$_1$-C$_6$ alkyl)-, HS(O)$_{0-2}$(C$_1$-C$_6$ alkyl)-, (C$_0$-C$_6$ alkyl)C(O)NH—, H₂N—C(NH)—, —O(C$_1$-C$_6$ alkyl)CF₃, HC(O)—, (C$_1$-C$_6$ alkyl)C(O)—, HOC(O)—, (C$_1$-C$_6$ alkyl)OC(O)—, HO(C$_1$-C$_6$ (C$_1$-C$_6$ alkyl)O(C$_1$-C$_6$ (C$_1$-C$_6$ alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$—, HOC(O)NH—, (C$_1$-C$_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound. Unless otherwise specified, alkyl groups are unsubstituted.

Except where noted, the term "halogen" means fluorine, chlorine, bromine or iodine.

Except where noted, the term "saturated heterocycle" refers to a stable 4- to 7-membered mono-cyclic or stable 7- to 12-membered bicyclic or stable 12- to 14-membered tricyclic heteroatom-containing ring system unsubstituted or substituted with C$_{1-4}$ alkyl or halogen, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane, and homopiperazine.

Except where noted herein, the term "unsaturated heterocycle" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Additional examples are pyridine, pyrimidine, thiophene, imidazole, isothiazole, oxadiazole, and isoxazole.

Except where noted herein, the term "unsaturated bicyclic heterocycle" or "unsaturated tricyclic heterocycle" refers to a heterocycle having fused rings in which at least one of the rings is not fully saturated, e.g.

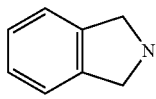

is a 9-membered unsaturated bicyclic heterocycle having one nitrogen atom.

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ monocyclic carbocycle, or a $C_9$ to $C_{12}$ bicyclic saturated or unsaturated ring, e.g., $C_{9-12}$ bicyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example, "aryl" rings. Unsaturated bicyclic carbocyclic ring systems include fused ring systems where all ring system members are carbon atoms and where at least one of the fused rings is not saturated.

Except where noted herein, the term "unsaturated bicyclic carbocycle" or "unsaturated tricyclic carbocycle" refers to a carbocycle having fused rings in which at least one of the rings is not fully saturated, e.g.

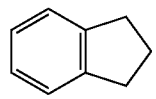

is a 9-membered unsaturated bicyclic carbocycle.

Except where noted, the term "aryl" refers to a stable 6- to 10-membered mono- or bicyclic unsaturated carbocyclic ring system such as phenyl, or naphthyl. The aryl ring can be unsubstituted or substituted with one or more of $C_{1-4}$ alkyl, hydroxyl, alkoxy, halogen, or amino.

"Celite®" (Fluka) diatomite is diatomaceous earth, and can be referred to as "celite".

Carbocycle groups may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, —P(O)(OH)$_2$, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound. Unless otherwise specified, carbocycle groups are unsubstituted.

Heterocycles may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$—, ($C_1$-$C_6$ alkyl)C(O)NH—, HC(O)NH—, $H_2$N—C(NH)—, —O($C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$, ($C_1$-$C_6$ alkyl)OC(O)NH—, HOC(O)NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl. Heterocycles may also be independently substituted with a substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NHC$_1$-$C_6$ alkyl, —C(O) $NH_2$, —$C_1$-$C_6$ alkylC(O) $NH_2$, —$C_1$-$C_6$ alkylOC(O)$NH_2$, or independently or additionally substituted with 1 substituent on any one or more sulfur atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, where such substitution results in formation of a stable compound. Heterocycles may also be substituted as described above on one or more carbon atoms and one or more heteroatoms, where such substitutions result in formation of a stable compound. Unless otherwise specified, heterocycle groups are unsubstituted.

Except where noted herein, structures containing substituent variables such as variable "R" below:

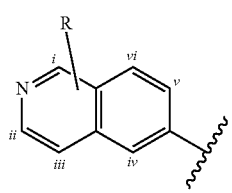

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also includes derivatives of the compound of Formula I, acting as prodrugs and solvates. Prodrugs, following administration to the patient, are converted in the body by normal metabolic or chemical processes, such as through hydrolysis in the blood, to the compound of Formula 1. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For the inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver about 0.01 mg per kg of body weight per day (mg/kg/day) to about 30 mg/kg/day, preferable 0.025-7.5 mg/kg/day, more preferably 0.1-2.5 mg/kg/day, and even more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes.

Substituent numbering as shown in the Reaction Schemes do not necessarily correlate to that used in the claims and often, for clarity, a single substituent is shown attached to the compound where multiple substituents are optionally allowed under the definitions of Formula I hereinabove.
Methods for Making the Compounds of Present Invention
General Methods The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

General Methods

All solvents used were commercially available and were used without further purification. Reactions were typically run using anhydrous solvents under an inert atmosphere of nitrogen.

$^1$H spectra were recorded at 300 or 400 MHz for proton on a Bruker Mercury Plus 400 NMR Spectrometer equipped with a Bruker 400 BBO probe. All deuterated solvents contained typically 0.03% to 0.05% v/v tetramethylsilane, which was used as the reference signal (set at δ 0.00 for both $^1$H and $^{13}$C).

LCMS analyses were performed on a SHIMADZU LCMS consisting of an UFLC 20-AD and LCMS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in MeCN) over 2.2 min with a total run time of 3.6 min. The column temperature was at 40° C. with the flow rate of 1.0 mL/min. The Diode Array Detector was scanned from 200-400 nm. The mass spectrometer was equipped with an electrospray ion source (ES) operated in a positive or negative mode.

HPLC analyses were performed on a SHIMADZU UFLC with two LC20 AD pump and a SPD-M20A Photodiode Array Detector. The column used was an)(Bridge $C_{18}$, 3.5 μm, 4.6×100 mm. A linear gradient was applied, starting at 90% A (A: 0.05% TFA in water) and ending at 95% B (B: 0.05% TFA in MeCN) over 10 min with a total run time of 15 min. The column temperature was at 40° C. with the flow rate of 1.5 mL/min. The Diode Array Detector was scanned from 200-400 nm.

Thin layer chromatography (TLC) was performed on Alugram (Silica gel 60 $F_{254}$) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24}\cdot 4H_2O$, 5 g $(NH_4)_2Ce(IV)(NO_3)_6$ in 450 mL water and 50 mL concentrated $H_2SO_4$) to visualize the compound. Flash chromatography was preformed using 40-63 μm (230-400 mesh) silica gel from Silicycle following analogous techniques to those disclosed in Still, W. C.; Kahn, M.; and Mitra, M. *Journal of Organic Chemistry*, 1978, 43, 2923. Typical solvents used for flash chromatography or thin layer chromatography were mixtures of chloroform/methanol, dichloromethane/methanol, ethyl acetate/methanol and petroleum ether/ethyl acetate.

Preparative HPLC was performed on either a Waters Prep LC 4000 System using a Waters 2487 Diode Array or on a Waters LC Module 1 plus. The column used was SunFire Prep C18 OBD Column, 5 μm, 19×150 mm. Narrow gradients with acetonitrile/water, with the water containing either 0.1% trifluoroacetic acid or 0.1% $NH_4HCO_3$, were used to elute the compound at a flow rate of 20 mL/min and a total run time between 20-30 min. Detector, 254 nm, 220 nm.

Chiral HPLC conditions: Column, Chiralpak IA, 5 μm, 20×150 mm; Mobile phase, Hex/EtOH or IPA; Detector, 254 nm, 220 nm.

Starting materials used were either available from commercial sources or prepared according to literature procedures and had experimental data in accordance with those reported.

The following abbreviations have been used:
AcOH acetic acid
aq. aqueous
BINAP 2,2'-bis(diphenylphosphino)-1,1'-binaphthyl
Boc tert-butyloxycarbonyl
$Boc_2O$ di-tert-butyl dicarbonate
BrettPhos 2-(Dicyclohexylphosphino)3,6-dimethoxy-2',4',6'-triisopropyl-1,1'-biphenyl
Conc. Concentrated
CDI carbonyl diimidazole
Calcd. calculated
DCM dichloromethane
DIEA diisopropylethylamine
DMAP 4-dimethylaminopyridine
DMF N,N-dimethylformamide
DMSO dimethylsulfoxide
DPP-Pd diphenylphosphine palladium (II)
EtOAc ethyl acetate
EI electron ionization
equiv. equivalent
EtOH ethanol
HPLC high performance liquid chromatography
IBX 2-iodoxybenzoic acid
J coupling constant
LCMS liquid chromatography-mass spectrometry
m-CPBA m-chloroperoxybenzoic acid
MeOH methanol
MeCN acetonitrile
$Na_2SO_4$ sodium sulfate
NMR nuclear magnetic resonance PPTS pyridinium p-toluenesulfonate
Prep-TLC preparative thin layer chromatography
pTsOH p-toluenesulfonic acid
TEA triethylamine
TFA trifluoroacetic acid
THF tetrahydrofuran
TMSCl trimethylchlorosilane
TLC thin layer chromatography
Ts tosyl
UV ultraviolet
W watts
wt. % percentage by weight
xg times gravity
$\alpha_D$ specific rotation of polarized light at 589 nm
° C. degrees Celsius
% w/v percentage in weight of the former agent relative to the volume of the latter agent General Scheme Compounds of the invention can be prepared following the general procedure described below:

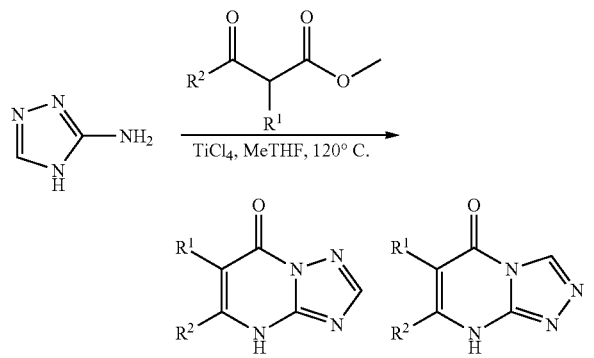

To a solution of 4H-1,2,4-triazol-3-amine (37.8 mg, 0.450 mmol) and β-ketoester (0.3 mmol) in 2-methyltetrahydrofuran (1.5 ml) is added titanium tetrachloride (0.300 ml, 0.300 mmol) and the resulting mixture is heated to 120° C. for 16 hours. The reaction mixture is concentrated, taken up in DMSO, filtered and purified by mass triggered reverse phase HPLC (MeCN/water with 0.1% TFA modifier, linear gradient) to afford the title compounds.

Scheme 1

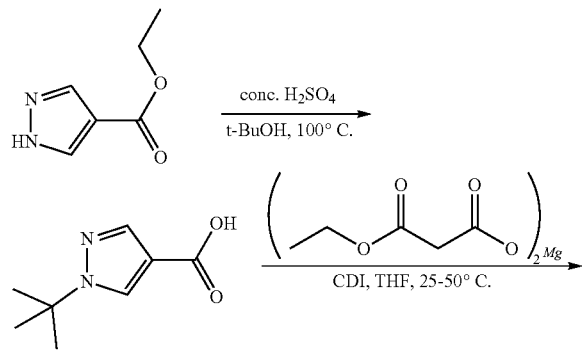

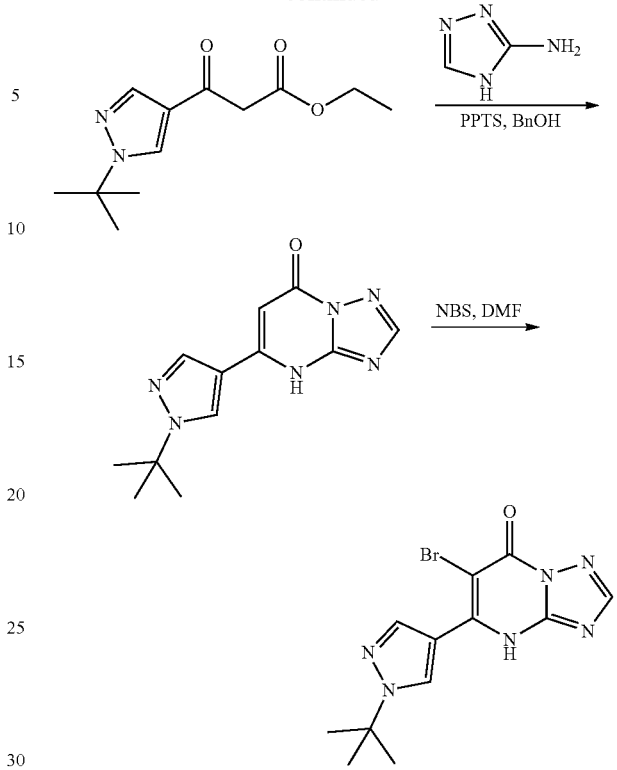

Synthesis of 6-bromo-5-(1-(tert-butyl)-1H-pyrazol-4-yl)-[1,2,4]triazolo[1,5-a]pyrimidin-7(4H)-one Step 1:
To a solution of ethyl 1H-pyrazole-4-carboxylate (5.4 g, 38.5 mmol) in t-butanol (20 mL) was added conc. $H_2SO_4$ (4 mL, 73.5 mmol) at 15° C. The mixture was stirred at 100° C. for 14 hours. The reaction was quenched with water (30 mL) and extracted with ethyl acetate (40 mL×3). The organic phase was washed with 2/1/NaOH (20 mL×2) and the aqueous was acidified with conc. HCl to pH-2 and extracted with ethyl acetate (30 mL×5). The combined organic phases were dried over anhydrous $Na_2SO_4$, filtered and concentrated to afford 1-(tert-butyl)-1H-pyrazole-4-carboxylic acid as a white solid. $^1$H NMR (400 MHz, DMSO-$d_6$) δ 12.17 (br, 1H); 8.24 (s, 1H); 7.81 (s, 1H); 1.52 (s, 9H).

Step 2:
A mixture of 1-(tert-butyl)-1H-pyrazole-4-carboxylic acid (3.74 g, 22.24 mmol) and CDI (4 g, 24.67 mmol) in THF (20 mL) was stirred at 15° C. for 10 hours. LCMS analysis showed no product formation. The reaction was heated to 55° C. for an additional 12 hours. LCMS analysis indicated the formation of the methyl ester via methanol quench. Magnesium 3-ethoxy-3-oxopropanoate (6.37 g, 22.23 mmol) was added and the resulting mixture was stirred at 55° C. for 14 hours. The reaction mixture was quenched with water (20 mL) and extracted with ethyl acetate (20 mL×3). The combined organic phases were washed with 1M NaOH (20 mL), brine (10 mL), dried over anhydrous $Na_2SO_4$, filtered and concentrated under reduced pressure. The residue was purified by column chromatography on silica (0-18% ethyl acetate/petroleum ether) to afford ethyl 3-(1-(tert-butyl)-1H-pyrazol-4-yl)-3-oxopropanoate as a brown solid. $^1$H NMR (400 MHz, chloroform-d) δ 8.08 (s, 1H); 7.96 (s, 1H); 4.22 (q, J=7.0 Hz, 2H); 3.76 (s, 2H); 1.61 (s, 9H); 1.28 (m, 3H).

Step 3:

A mixture of ethyl 3-(1-(tert-butyl)-1H-pyrazol-4-yl)-3-oxopropanoate (5 g, 20.98 mmol), 1H-1,2,4-triazol-5-amine (2.7 g, 31.5 mmol) and PPTS (5.3 g, 21.09 mmol) in benzyl alcohol (4 mL) was stirred at 120° C. for 18 hours. Water (50 mL) was added, and the formed precipitate collected by filtration. The crude was washed with water (100 mL×3) and ethyl acetate (100 mL×3) to afford 5-(1-(tert-butyl)-1H-pyrazol-4-yl)-[1,2,4]triazolo[1,5-a]pyrimidin-7(4H)-one as light yellow solid. $^1$H NMR (400 MHz, methanol-d$_4$) δ 8.49 (s, 1H); 8.20 (s, 1H); 8.11 (s, 1H); 6.35 (s, 1H); 1.64 (s, 9H).

Step 4:

A solution of 5-(1-(tert-butyl)-1H-pyrazol-4-yl)-[1,2,4]triazolo[1,5-a]pyrimidin-7(4H)-one (5.824 g, 22.55 mmol) and N-bromosuccinimide (4.01 g, 22.55 mmol) in DMF (160 mL) was stirred at 15° C. for 2 hours. The reaction was quenched with water (200 mL) and the formed precipitate collected via filtration. The precipitate was washed with water (100 mL×3), DCM (100 mL×2) and ethyl acetate (100 mL×3) to afford 6-bromo-5-(1-(tert-butyl)-1H-pyrazol-4-yl)-[1,2,4]triazolo[1,5-a]pyrimidin-7(4H)-one as a white solid. $^1$H NMR (400 MHz, DMSO-d$_6$) δ 8.59 (br, 1H); 8.51 (s, 1H); 8.21 (s, 1H); 1.58 (s, 9H).

Scheme 2

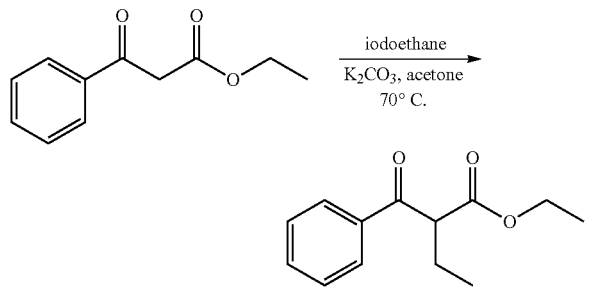

Synthesis of ethyl 2-benzoylbutanoate

To a 20 mL reaction vial charged with ethyl 3-oxo-3-phenylpropanoate (500 mg, 2.60 mmol), potassium carbonate (1438 mg, 10.41 mmol) and acetone (8 ml) was added iodoethane (0.210 ml, 2.60 mmol). The vial was capped and the contents heated to 70° C. with stirring for 16 hours. The mixture was cooled, diluted with ethyl acetate (10 mL), washed with water (10 mL), dried (MgSO$_4$), filtered, and the solvent was evaporated under reduced pressure to afford crude ethyl 2-benzoylbutanoate as a yellow oil. $^1$H NMR (600 MHz, DMSO-d$_6$): δ 7.95 (d, J=7.8 Hz, 2H); 7.64 (t, J=7.4 Hz, 1H); 7.52 (t, J=7.6 Hz, 2H); 4.52 (t, J=6.6 Hz, 1H); 4.02 (q, J=7.1 Hz, 2H); 1.82 (p, J=7.3 Hz, 2H); 1.04 (t, J=7.1 Hz, 3H); 0.86 (t, J=7.4 Hz, 3H).

Scheme 3

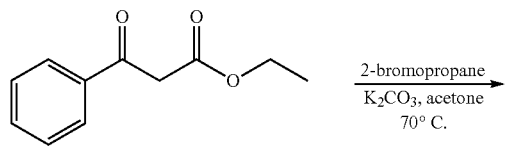

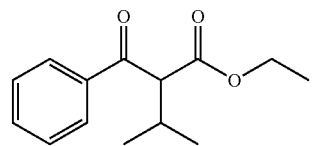

Synthesis of ethyl 2-benzoyl-3-methylbutanoate

To a 20 mL reaction vial charged with ethyl 3-oxo-3-phenylpropanoate (120 mg, 0.624 mmol), potassium carbonate (345 mg, 2.497 mmol) and acetone (5 ml) was added 2-bromopropane (0.059 ml, 0.624 mmol). The vial was capped and the contents heated to 70° C. with stirring for 16 hours. The mixture was cooled, diluted with ethyl acetate (10 mL), washed with water (10 mL), dried (MgSO$_4$), filtered, and the solvent was evaporated under reduced pressure. The residue was purified by column chromatography on silica (0-20% hexanes/ethyl acetate) to afford a 3:2 mixture of desired product and unreacted starting material, which was carried forward to the next step. MS ESI calcd. for $C_{14}H_{18}O_3$ [M+H]$^+$ 235, found 235.

Scheme 4

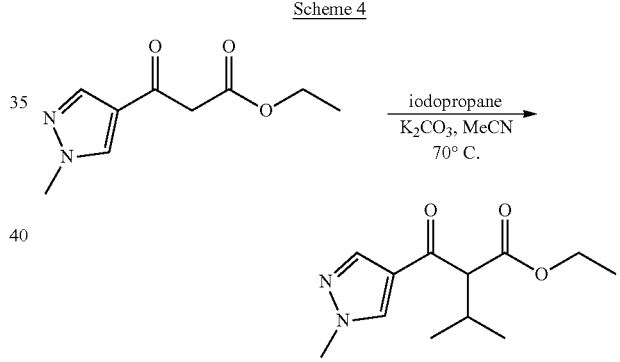

Synthesis of ethyl 2-benzoylbutanoate

To a 20 mL reaction vial charged with ethyl 3-(1-methyl-1H-pyrazol-4-yl)-3-oxopropanoate (100 mg, 0.510 mmol), potassium carbonate (282 mg, 2.039 mmol) and acetonitrile (5 ml) was added 2-iodopropane (0.102 ml, 1.019 mmol). The vial was capped and the contents heated to 70° C. with stirring for 16 hours. The mixture was cooled, diluted with chloroform/isopropanol—3:1 (10 mL), washed with water (10 mL), dried (MgSO$_4$), filtered and the solvent was evaporated under reduced pressure to afford crude ethyl 3-methyl-2-(1-methyl-1H-pyrazole-4-carbonyl)butanoate as a yellow oil. $^1$H NMR (600 MHz, DMSO-d$_6$): δ 8.42 (s, 1H); 7.94 (s, 1H); 4.04-4.02 (m, 2H); 3.84 (s, 3H); 2.34-2.29 (m, 1H); 1.19-1.15 (m, 1H); 1.07 (t, J=7.1 Hz, 3H); 0.91 (d, J=6.7 Hz, 3H); 0.79 (d, J=6.7 Hz, 3H).

Scheme 5

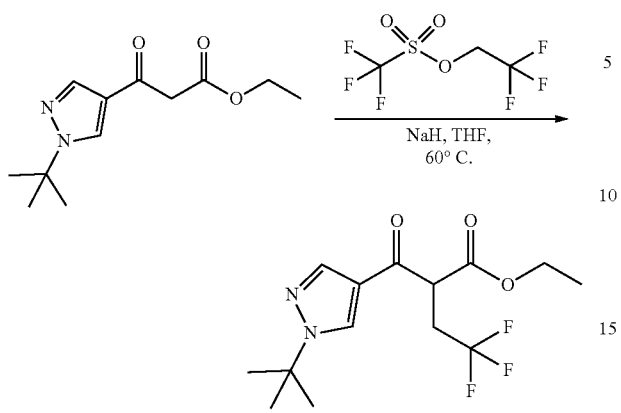

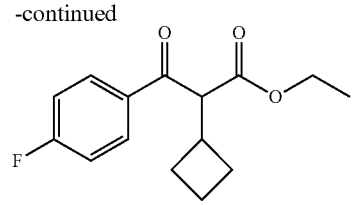

Synthesis of ethyl 2-(1-(tert-butyl)-1H-pyrazole-4-carbonyl)-4,4,4-trifluorobutanoate To an ice-cold solution of ethyl 3-(1-(tert-butyl)-1H-pyrazol-4-yl)-3-oxopropanoate (1.5 g, 6.30 mmol) in THF (15 mL) was added sodium hydride (0.504 g, 12.59 mmol, 60% in oil) portion-wise. The resulting mixture was stirred for 30 minutes at 0° C., followed by the addition of a solution of 2,2,2-trifluoroethyl trifluoromethanesulfonate (2.192 g, 9.44 mmol) in THF (5 mL). The reaction mixture was stirred at 60° C. for an additional 14 hours. The reaction was quenched with water (30 mL) and then extracted with ethyl acetate (30 mL×3). The combined organic phases were washed with saturated brine (20 mL×2), dried over anhydrous $Na_2SO_4$, filtered and concentrated in vacuo. The residue was purified by column chromatography on silica (0-30% ethyl acetate/petroleum ether) to afford the product with impurity. This was further re-purified by mass triggered reverse phase HPLC (MeCN/water with 0.1% TFA modifier, linear gradient) to afford ethyl 2-(1-(tert-butyl)-1H-pyrazole-4-carbonyl)-4,4,4-trifluorobutanoate as colorless oil. $^1$H NMR (400 MHz, chloroform-d) δ 8.15 (s, 1H); 8.05 (s, 1H); 4.20 (d, J=7.04 Hz, 3H); 2.98-2.81 (m, 2H); 1.63 (s, 9H); 1.24 (t, J=7.14 Hz, 3H).

Synthesis of ethyl 2-cyclobutyl-3-(4-fluorophenyl)-3-oxopropanoate

Step 1:

A 20 mL reaction vial was charged with ethyl 3-(4-fluorophenyl)-3-oxopropanoate (0.256 ml, 1.427 mmol), cyclobutanone (240 mg, 3.43 mmol) and 2-methyltetrahydrofuran (10 ml). Titanium tetrachloride (3.00 ml, 3.00 mmol) and pyridine (0.577 ml, 7.14 mmol) were added, the vial capped, and the contents stirred at 60° C. for 5 hours. The mixture was cooled, the formed precipitate removed by filtration, washing through with ethyl acetate. The filtrate was diluted with ethyl acetate (10 mL), washed with brine, dried ($MgSO_4$), filtered, and the solvent was evaporated under reduced pressure. The residue was purified by column chromatography on silica (0-20% hexanes/ethyl acetate) to afford ethyl 2-cyclobutylidene-3-(4-fluorophenyl)-3-oxopropanoate as a yellow oil. $^1$H NMR (600 MHz, DMSO-$d_6$): δ 7.82 (dd, J=8.3, 5.4 Hz, 2H); 7.32 (t, J=8.6 Hz, 2H); 4.02 (q, J=7.1 Hz, 2H); 2.69 (t, J=7.8 Hz, 2H); 2.03 (p, J=7.9 Hz, 2H); 1.03 (t, J=7.1 Hz, 3H).

Step 2:

A hydrogen filled balloon was attached to a flask charged with a stirring suspension of 10% palladium on carbon (149 mg, 0.140 mmol) in a solution of ethyl 2-cyclobutylidene-3-(4-fluorophenyl)-3-oxopropanoate (184 mg, 0.702 mmol) and ethyl acetate (10 ml). The reaction vessel was evacuated and flushed with hydrogen. This procedure was carried out a further two times. The reaction mixture was stirred at room temperature for 2 hours. The reaction was filtered through celite and concentrated to afford crude ethyl 2-cyclobutyl-3-(4-fluorophenyl)-3-oxopropanoate as a colorless oil which was taken forward without further purification. $^1$H NMR (600 MHz, DMSO-$d_6$): δ 8.04 (dd, J=8.4, 5.4 Hz, 2H); 7.35 (t, J=8.5 Hz, 2H); 4.68 (d, J=10.1 Hz, 1H); 4.00 (q, J=7.1 Hz, 2H); 2.91-2.85 (m, 1H); 2.01 (t, J=8.7 Hz, 1H); 1.90-1.79 (m, 3H); 1.76-1.71 (m, 1H); 1.67-1.61 (m, 1H); 1.02 (t, J=7.1 Hz, 3H).

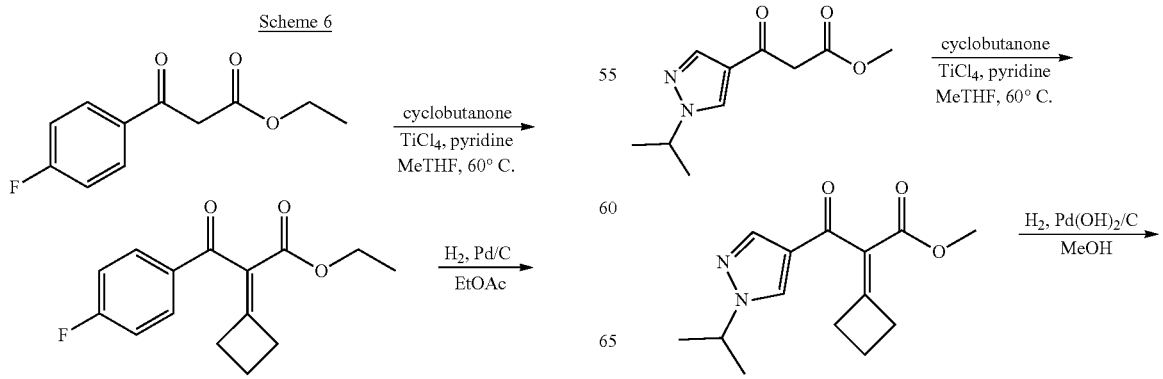

-continued

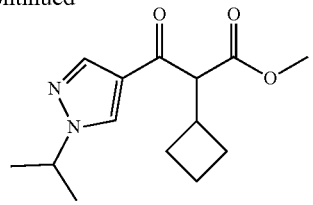

Synthesis of methyl 2-cyclobutyl-3-(1-isopropyl-1H-pyrazol-4-yl)-3-oxopropanoate Step 1:

A 20 mL reaction vial was charged with methyl 3-(1-isopropyl-1H-pyrazol-4-yl)-3-oxopropanoate (328 mg, 1.560 mmol), cyclobutanone (262 mg, 3.74 mmol) and 2-methyltetrahydrofuran (10 ml). Titanium tetrachloride (3.28 ml, 3.28 mmol) and pyridine (0.631 ml, 7.80 mmol) were added. The vial was capped and the contents stirred at 60° C. for 5 hours. The mixture was cooled, the formed precipitate removed by filtration, washing through with ethyl acetate. The filtrate was diluted with ethyl acetate (10 mL), washed with 1N HCl (10 mL), brine, dried ($MgSO_4$), filtered, and the solvent was evaporated under reduced pressure to afford crude methyl 2-cyclobutylidene-3-(1-isopropyl-1H-pyrazol-4-yl)-3-oxopropanoate. $^1$H NMR (600 MHz, DMSO-$d_6$): δ 8.29 (s, 1H); 7.77 (s, 1H); 4.53-4.49 (m, 1H); 3.58 (s, 3H); 3.14 (t, J=7.9 Hz, 2H); 2.70 (t, J=7.7 Hz, 2H); 2.03-1.97 (2H); 1.38 (d, J=6.6 Hz, 6H).

Step 2:

A hydrogen filled balloon was attached to a flask charged with a stirring suspension of 20% palladium hydroxide on carbon (171 mg, 0.244 mmol) in a solution of methyl 2-cyclobutylidene-3-(1-isopropyl-1H-pyrazol-4-yl)-3-oxo-propanoate (320 mg, 1.220 mmol) and methanol (10 ml). The reaction vessel was evacuated and flushed with hydrogen. This procedure was carried out a further two times. The reaction mixture was stirred at room temperature for 16 hours. The reaction mixture was filtered through celite, washing with methanol and concentrated to afford methyl 2-cyclobutyl-3-(1-isopropyl-1H-pyrazol-4-yl)-3-oxopropanoate. $^1$H NMR (600 MHz, DMSO-$d_6$): δ 8.51 (s, 1H); 7.97 (s, 1H); 4.53-4.49 (m, 1H); 4.29 (d, J=10.4 Hz, 1H); 3.53 (s, 3H); 2.86-2.82 (m, 1H); 2.04-2.03 (s, 1H); 1.79-1.76 (m, 4H); 1.74-1.71 (m, 1H); 1.64 (t, J=10.2 Hz, 1H); 1.40 (d, J=6.7 Hz, 6H).

Scheme 8

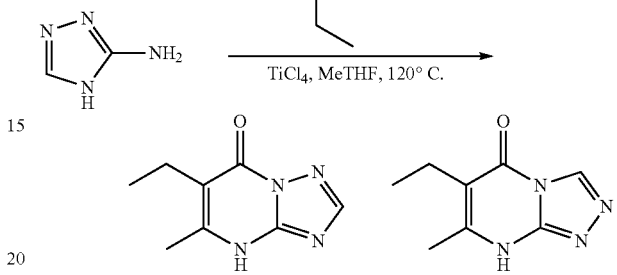

Example 8-1 and 8-2

Synthesis of 6-ethyl-5-methyl-[1,2,4]triazolo[1,5-a]pyrimidin-7(4H)-one and 6-ethyl-7-methyl-[1,2,4]triazolo[4,3-a]pyrimidin-5(8H)-one To a solution of 4H-1,2,4-triazol-3-amine (37.8 mg, 0.450 mmol) and ethyl 2-ethyl-3-oxobutanoate (0.048 ml, 0.3 mmol) in 2-methyltetrahydrofuran (1.5 ml) was added titanium tetrachloride (0.300 ml, 0.300 mmol), and the resulting mixture was heated to 120° C. for 16 hours. The reaction mixture was concentrated, taken up in DMSO, filtered and purified by mass triggered reverse phase HPLC (MeCN/water with 0.1% TFA modifier, linear gradient) to afford 6-ethyl-5-methyl-[1,2,4]triazolo[1,5-a]pyrimidin-7(4H)-one; $^1$H NMR (600 MHz, DMSO-$d_6$): δ 12.96 (s, 1H); 8.11 (s, 1H); 2.44-2.42 (m, 2H); 2.32 (s, 3H); 0.99 (t, J=7.4 Hz, 3H) and 6-ethyl-7-methyl-[1,2,4]triazolo[4,3-a]pyrimidin-5(8H)-one (20.4 mg, 0.114 mmol, 38.2% yield); $^1$H NMR (600 MHz, DMSO-$d_6$): δ 8.92 (s, 1H); 2.41 (q, J=7.4 Hz, 2H); 2.31 (s, 3H); 0.97 (t, J=7.4 Hz, 3H).

The following compounds (Table 1) were synthesized as described;

TABLE 1

| Ex No. | Structure | Name | Exact Mass [M + H]+ | IC50 (nM) |
|---|---|---|---|---|
| 8-36 | 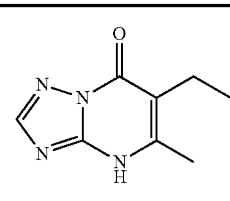 | 6-ethyl-5-methyl-[1,2,4]triazolo[1,5-a]pyrimidin-7(4H)-one | Calc'd 179, found 179 | 3494 |
| 8-37 | 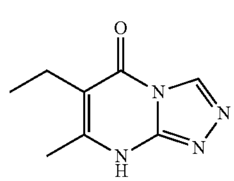 | 6-ethyl-7-methyl[1,2,4]triazolo[4,3-a]pyrimidin-5(8H)-one | Calc'd 179, found 179 | 91680 |

TABLE 1-continued

| Ex No. | Structure | Name | Exact Mass [M + H]+ | IC50 (nM) |
|---|---|---|---|---|
| 8-3 | 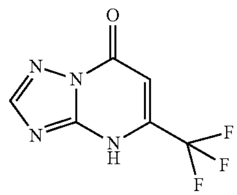 [SMILES: O=c1cc(C(F)(F)F)[nH]c2ncnn12] | 5-(trifluoromethyl)[1,2,4]triazolo[1,5-a]pyrimidin-7(4H)-one | Calc'd 205, found 205 | 13400 |
| 8-4 | 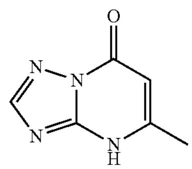 | 5-methyl-[1,2,4]triazolo[1,5-a]pyrimidin-7(4H)-one | Calc'd 151, found 151 | 26400 |
| 8-5 | 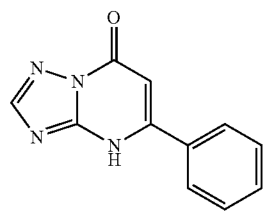 [SMILES: O=c1cc(-c2ccccc2)[nH]c2ncnn12] | 5-phenyl-[1,2,4]triazolo[1,5-a]pyrimidin-7(4H)-one | Calc'd 213, found 213 | 2240 |
| 8-6 | 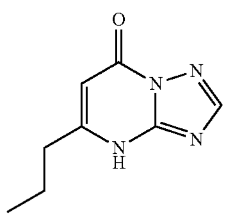 | 5-propyl[1,2,4]triazolo[1,5-a]pyrimidin-7(4H)-one | Calc'd 179, found 179 | 47620 |
| 8-7 | 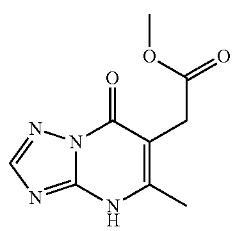 [SMILES: COC(=O)Cc1c(C)[nH]c2ncnn2c1=O] | methyl (5-methyl-7-oxo-4,7-dihydro[1,2,4]triazolo[1,5-a]pyrimidin-6-yl)acetate | Calc'd 223, found 223 | 21280 |
| 8-8 | 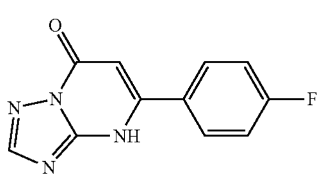 [SMILES: O=c1cc(-c2ccc(F)cc2)[nH]c2ncnn12] | 5-(4-fluorophenyl)[1,2,4]triazolo[1,5-a]pyrimidin-7(4H)-one | Calc'd 231, found 231 | 1302 |
| 8-9 | 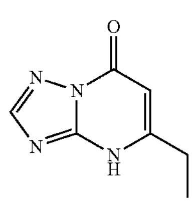 | 5-ethyl-[1,2,4]triazolo[1,5-a]pyrimidin-7(4H)-one | Calc'd 165, found 165 | 21790 |

TABLE 1-continued

| Ex No. | Structure | Name | Exact Mass [M + H]+ | IC50 (nM) |
|---|---|---|---|---|
| 8-10 | 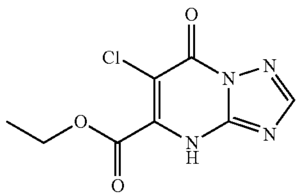 [SMILES: CCOC(=O)c1[nH]c2ncnn2c(=O)c1Cl] | ethyl 6-chloro-7-oxo-4,7-dihydro[1,2,4]triazolo[1,5-a]pyrimidine-5-carboxylate | Calc'd 243, found 243 | 6278 |
| 8-11 | 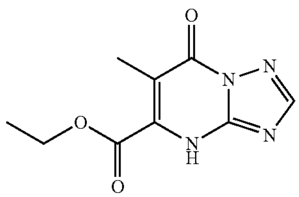 [SMILES: CCOC(=O)c1[nH]c2ncnn2c(=O)c1C] | ethyl 6-methyl-7-oxo-4,7-dihydro[1,2,4]triazolo[1,5-a]pyrimidine-5-carboxylate | Calc'd 223, found 223 | 6745 |
| 8-12 | 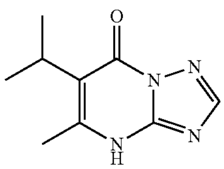 | 5-methyl-6-(1-methylethyl)[1,2,4]triazolo[1,5-a]pyrimidin-7(4H)-one | Calc'd 193, found 193 | 474.3 |
| 8-13 | 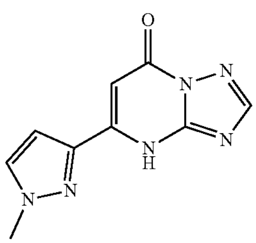 [SMILES: Cn1ccc(-c2cc(=O)n3ncnc3[nH]2)n1] | 5-(1-methyl-1H-pyrazol-3-yl)[1,2,4]triazolo[1,5-a]pyrimidin-7(4H)-one | Calc'd 217, found 217 | 29210 |
| 8-14 | 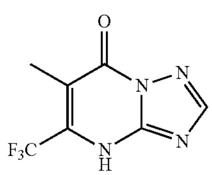 | 5-methyl-6-(trifluoromethyl)[1,2,4]triazolo[1,5-a]pyrimidin-7(4H)-one | Calc'd 219, found 219 | 9734 |
| 8-15 | 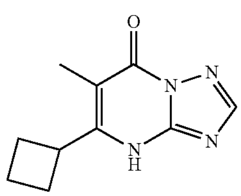 | 6-cyclobutyl-5-methyl[1,2,4]triazolo[1,5-a]pyrimidin-7(4H)-one | Calc'd 205, found 205 | 19230 |
| 8-16 | 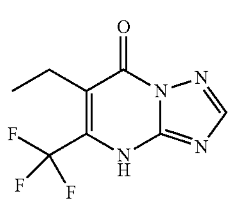 [SMILES: CCc1c(C(F)(F)F)[nH]c2ncnn2c1=O] | 6-ethyl-5-(trifluoromethyl)[1,2,4]triazolo[1,5-a]pyrimidin-7(4H)-one | Calc'd 233, found 233 | 1587 |
| 8-17 | 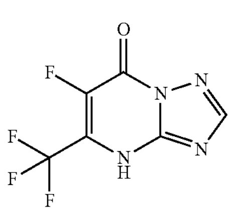 [SMILES: O=c1c(F)c(C(F)(F)F)[nH]c2ncnn12] | 6-fluoro-5-(trifluoromethyl)[1,2,4]triazolo[1,5-a]pyrimidin-7(4H)-one | Calc'd 223, found 223 | 25660 |

TABLE 1-continued

| Ex No. | Structure | Name | Exact Mass [M + H]+ | IC50 (nM) |
|---|---|---|---|---|
| 8-18 | 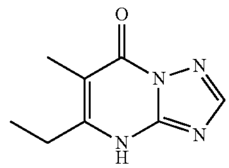 | 5-ethyl-6-methyl[1,2,4]triazolo[1,5-a]pyrimidin-7(4H)-one | Calc'd 179, found 179 | 31860 |
| 8-19 | 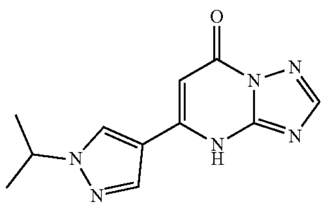 [SMILES: CC(C)n1cc(-c2cc(=O)n3ncnc3[nH]2)cn1] | 5-[1-(1-methylethyl)-1H-pyrazol-4-yl][1,2,4]triazolo[1,5-a]pyrimidin-7(4H)-one | Calc'd 245, found 245 | 1534 |
| 8-20 | 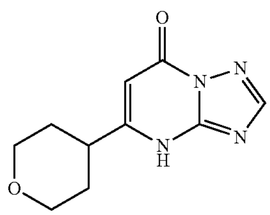 [SMILES: O=c1cc(C2CCOCC2)[nH]c2ncnn12] | 5-(tetrahydro-2H-pyran-4-yl)[1,2,4]triazolo[1,5-a]pyrimidin-7(4H)-one | Calc'd 221, found 221 | 81320 |
| 8-21 | 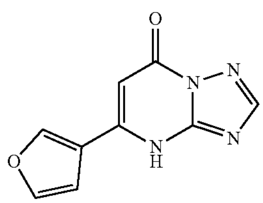 [SMILES: O=c1cc(-c2ccoc2)[nH]c2ncnn12] | 5-furan-3-yl[1,2,4]triazolo[1,5-a]pyrimidin-7(4H)-one | Calc'd 203, found 203 | 4103 |
| 8-22 | 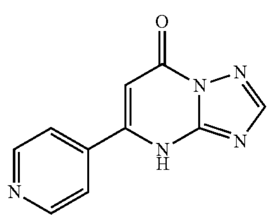 [SMILES: O=c1cc(-c2ccncc2)[nH]c2ncnn12] | 5-pyridin-4-yl[1,2,4]triazolo[1,5-a]pyrimidin-7(4H)-one | Calc'd 214, found 214 | 18890 |
| 8-23 | 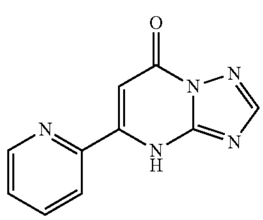 [SMILES: O=c1cc(-c2ccccn2)[nH]c2ncnn12] | 5-pyridin-2-yl[1,2,4]triazolo[1,5-a]pyrimidin-7(4H)-one | Calc'd 214, found 214 | 2423 |
| 8-24 | 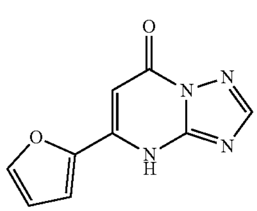 [SMILES: O=c1cc(-c2ccco2)[nH]c2ncnn12] | 5-furan-2-yl[1,2,4]triazolo[1,5-a]pyrimidin-7(4H)-one | Calc'd 203, found 203 | 6785 |

TABLE 1-continued

| Ex No. | Structure | Name | Exact Mass [M + H]+ | IC50 (nM) |
|---|---|---|---|---|
| 8-25 | 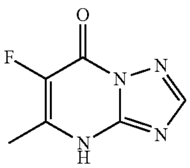 | 6-fluoro-5-methyl[1,2,4]triazolo[1,5-a]pyrimidin-7(4H)-one | Calc'd 169, found 169 | 17910 |
| 8-26 | 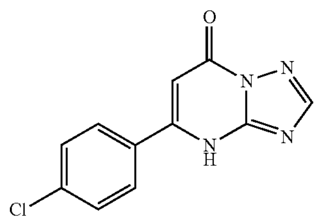 [SMILES: O=c1cc(-c2ccc(Cl)cc2)[nH]c2ncnn12] | 5-(4-chlorophenyl)[1,2,4]triazolo[1,5-a]pyrimidin-7(4H)-one | Calc'd 247, found 247 | 1389 |
| 8-27 | 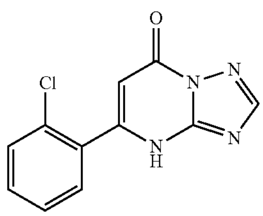 [SMILES: O=c1cc(-c2ccccc2Cl)[nH]c2ncnn12] | 5-(2-chlorophenyl)[1,2,4]triazolo[1,5-a]pyrimidin-7(4H)-one | Calc'd 247, found 247 | 10140 |
| 8-28 | 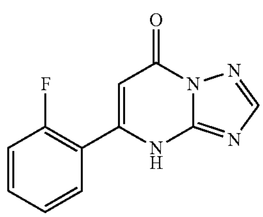 [SMILES: O=c1cc(-c2ccccc2F)[nH]c2ncnn12] | 5-(2-fluorophenyl)[1,2,4]triazolo[1,5-a]pyrimidin-7(4H)-one | Calc'd 231, found 231 | 5536 |
| 8-29 | 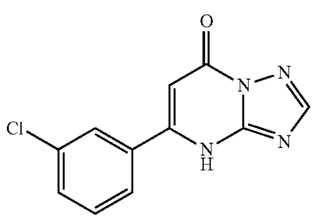 [SMILES: O=c1cc(-c2cccc(Cl)c2)[nH]c2ncnn12] | 5-(3-chlorophenyl)[1,2,4]triazolo[1,5-a]pyrimidin-7(4H)-one | Calc'd 247, found 247 | 2982 |
| 8-30 | 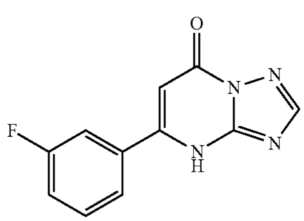 [SMILES: O=c1cc(-c2cccc(F)c2)[nH]c2ncnn12] | 5-(3-fluorophenyl)[1,2,4]triazolo[1,5-a]pyrimidin-7(4H)-one | Calc'd 231, found 231 | 2453 |
| 8-31 | 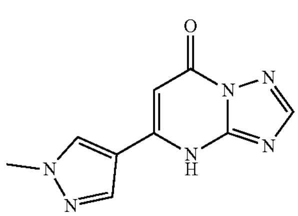 [SMILES: Cn1cc(-c2cc(=O)n3ncnc3[nH]2)cn1] | 5-(1-methyl-1H-pyrazol-4-yl)[1,2,4]triazolo[1,5-a]pyrimidin-7(4H)-one | Calc'd 217, found 217 | 3333 |

TABLE 1-continued

| Ex No. | Structure | Name | Exact Mass [M + H]+ | IC50 (nM) |
|---|---|---|---|---|
| 8-32 | 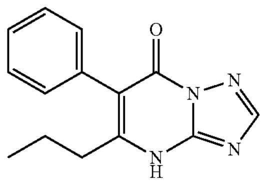 [SMILES: CCCc1[nH]c2ncnn2c(=O)c1-c1ccccc1] | 6-phenyl-5-propyl[1,2,4]triazolo[1,5-a]pyrimidin-7(4H)-one | Calc'd 255, found 255 | 37610 |
| 8-33 | 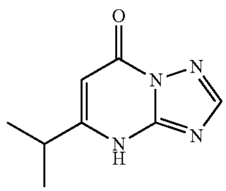 | 5-(1-methylethyl)[1,2,4]triazolo[1,5-a]pyrimidin-7(4H)-one | Calc'd 179, found 179 | 82280 |
| 8-34 | 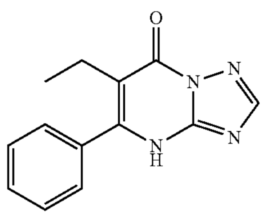 [SMILES: CCc1c(-c2ccccc2)[nH]c2ncnn2c1=O] | 6-ethyl-5-phenyl[1,2,4]triazolo[1,5-a]pyrimidin-7(4H)-one | Calc'd 241, found 241 | 518.8 |
| 8-35 | 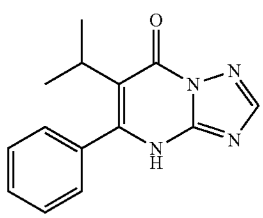 [SMILES: CC(C)c1c(-c2ccccc2)[nH]c2ncnn2c1=O] | 6-(1-methylethyl)-5-phenyl[1,2,4]triazolo[1,5-a]pyrimidin-7(4H)-one | Calc'd 255, found 255 | 270.6 |
| 8-40 | 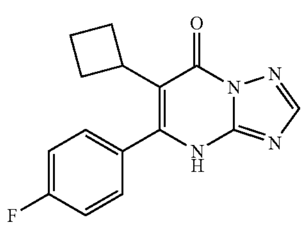 [SMILES: O=c1c(C2CCC2)c(-c2ccc(F)cc2)[nH]c2ncnn12] | 6-cyclobutyl-5-(4-fluorophenyl)[1,2,4]triazolo[1,5-a]pyrimidin-7(4H)-one | Calc'd 285, found 285 | 1032 |
| 8-41 | 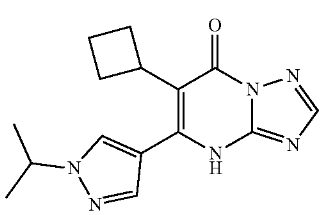 [SMILES: CC(C)n1cc(-c2[nH]c3ncnn3c(=O)c2C2CCC2)cn1] | 6-cyclobutyl-5-[1-(1-methylethyl)-1H-pyrazol-4-yl][1,2,4]triazolo[1,5-a]pyrimidin-7(4H)-one | Calc'd 299, found 299 | 32.9 |
| 8-38 | 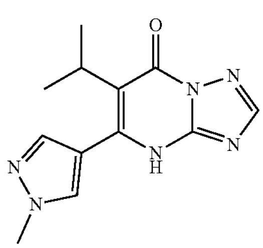 [SMILES: CC(C)c1c(-c2cnn(C)c2)[nH]c2ncnn2c1=O] | 6-(1-methylethyl)-5-(1-methyl-1H-pyrazol-4-yl)[1,2,4]triazolo[1,5-a]pyrimidin-7(4H)-one | Calc'd 259, found 259 | 16.22 |

TABLE 1-continued

| Ex No. | Structure | Name | Exact Mass [M + H]+ | IC50 (nM) |
|---|---|---|---|---|
| 8-39 | (structure) | 5-(1-tert-butyl-1H-pyrazol-4-yl)-6-(2,2,2-trifluoroethyl)[1,2,4]triazolo[1,5-a]pyrimidin-7(4H)-one | Calc'd 341, found 341 | 87.13 |

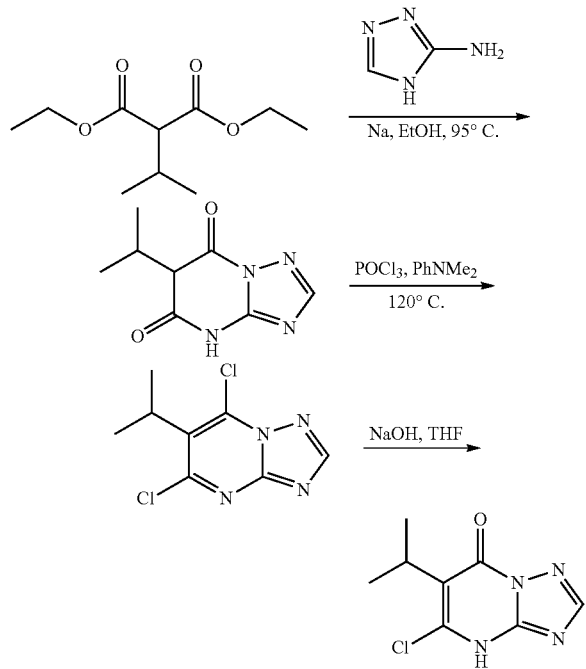

Scheme 9

Synthesis of 5-chloro-6-isopropyl-[1,2,4]triazolo[1,5-a]pyrimidin-7(4H)-one

Step 1:

To a mixture of sodium (5.5 g, 239 mmol) and ethanol (135 ml) which was stirred at 15° C. for 1 hour was added successively diethyl 2-isopropylmalonate (32 ml, 155 mmol) and 1H-1,2,4-triazol-5-amine (9.06 g, 108 mmol). The resulting mixture was stirred at 95° C. for 24 hours to form a white solution. After cooling to room temperature, the precipitates were collected by filtration and dissolved in water. The aqueous solution was acidified with 2N HCl (pH-2). The resulting precipitates were collected by filtration, washed with petroleum ether, water and dried under vacuum to afford 6-isopropyl-[1,2,4]triazolo[1,5-a]pyrimidine-5,7(4H,6H)-dione as a white powder. $^1$H NMR (400 MHz, methanol-d$_4$) δ 8.40 (s, 1H); 3.38-3.32 (m, 1H); 1.29 (d, J=7.1 Hz, 6H), 1.18-1.02 (m, 1H).

Step 2:

To a mixture of 6-isopropyl-[1,2,4]triazolo[1,5-a]pyrimidine-5,7(4H,6H)-dione (10 g, 51.5 mmol) and phosphoryl trichloride (49.9 ml, 533 mmol) was added N,N-dimethylaniline (6.04 ml, 51.5 mmol) at 15° C. The resulting mixture was stirred at 120° C. for 3 hours to form a brown solution. The mixture was concentrated, and the residue quenched carefully with ice water (200 g). The resulting mixture was neutralized with sat. NaHCO$_3$ to pH-8 and extracted with ethyl acetate (150 mL×3). The combined organic phases were washed with brine (20 mL), dried over anhydrous Na$_2$SO$_4$, filtered and concentrated under reduced pressure. The residue was purified by column chromatography on silica (10-25% ethyl acetate/petroleum ether) to afford 5,7-dichloro-6-isopropyl-[1,2,4]triazolo[1,5-a]pyrimidine as a white solid. $^1$H NMR (400 MHz, chloroform-d) δ 8.50 (s, 1H); 3.87 (td, J=6.8, 13.7 Hz, 1H); 1.52 (d, J=7.0 Hz, 6H).

Step 3:

To a mixture of 5,7-dichloro-6-isopropyl-[1,2,4]triazolo[1,5-a]pyrimidine (30.1 g, 130 mmol) and THF (300 ml) was added 2M aqueous sodium hydroxide (261 ml, 521 mmol) at 15° C. The mixture was stirred at 15° C. for 18 hours. The mixture was acidified to pH~4 with 1M HCl to form a white precipitate which was extracted with ethyl acetate (300 mL×3). The combined organic layers were dried over anhydrous Na$_2$SO$_4$, filtered and concentrated. The resulting residue was washed with DCM/methanol (10/1) (200 mL) and dried under high vacuum to afford 5-chloro-6-isopropyl-[1,2,4]triazolo[1,5-a]pyrimidin-7(4H)-one as a white solid which was taken forward without further purification. $^1$H NMR (400 MHz, DMSO-d$_6$) δ 8.82 (s, 1H); 3.31 (m, 1H); 1.28 (d, J=7.1 Hz, 6H).

Scheme 10

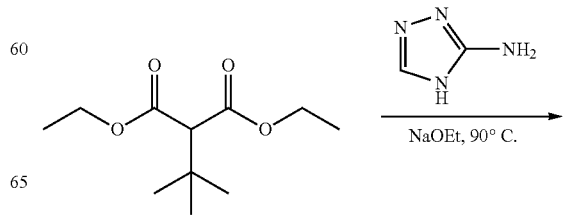

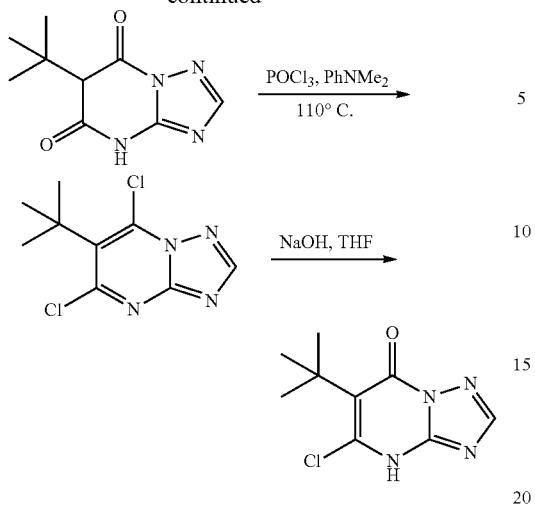

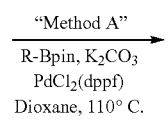

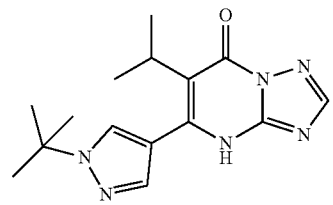

Synthesis of 6-(tert-butyl)-5-chloro-[1,2,4]triazolo[1,5-a]pyrimidin-7(4H)-one Step 1:

To a 20 mL pressure vial charged with 1H-1,2,4-triazol-5-amine (155 mg, 1.843 mmol), diethyl 2-(tert-butyl)malonate (399 mg, 1.843 mmol) and ethanol (4 ml) was added sodium ethoxide (1.445 ml, 3.87 mmol). The vial was capped, and the contents heated to 90° C. for 16 hours. The mixture was cooled, concentrated, acidified to pH 2 with 1N HCl, and extracted with ethyl acetate (2×10 mL). The organic layer was dried (MgSO$_4$), filtered and the solvent was evaporated under reduced pressure to afforde crude 6-(tert-butyl)-[1,2,4]triazolo[1,5-a]pyrimidine-5,7(4H,6H)-dione as an orange oil. MS ESI calcd. for $C_9H_{12}N_4O_2$ [M+H]$^+$ 209, found 209.

Step 2:

A 20 mL reaction vial was charged with 6-(tert-butyl)-[1,2,4]triazolo[1,5-a]pyrimidine-5,7(4H,6H)-dione (184 mg, 0.884 mmol), phosphoryl trichloride (659 7.07 mmol) and N,N-dimethylaniline (112 µl, 0.884 mmol). The vial was capped and the contents heated to 110° C. for 5 hours. The reaction mixture was concentrated, diluted with ethyl acetate (5 mL), washed with hydrochloric acid (1M, 5 mL), dried (MgSO$_4$), filtered and the solvent was evaporated under reduced pressure. The resulting crude 6-(tert-butyl)-5,7-dichloro-[1,2,4]triazolo[1,5-a]pyrimidine was taken forward without further purification. MS ESI calcd. for $C_9H_{10}Cl_2N_4$ [M+H]$^+$ 245, found 245.

Step 3:

To a 20 mL reaction vial charged with 6-(tert-butyl)-5,7-dichloro-[1,2,4]triazolo[1,5-a]pyrimidine (162 mg, 0.661 mmol) in THF (4 ml) was added sodium hydroxide (1.322 ml, 3.30 mmol). The reaction mixture was stirred at room temperature for 3 hours. The mixture was diluted with ethyl acetate (5 mL), washed with hydrochloric acid (1M, 2×5 mL), dried (MgSO$_4$), filtered and the solvent was evaporated under reduced pressure. The resulting crude 6-(tert-butyl)-5-chloro-[1,2,4]triazolo[1,5-a]pyrimidin-7(4H)-one was taken forward to the next step. MS ESI calcd. for $C_9H_{11}ClN_4O$ [M+H]$^+$ 227, found 227.

Scheme 11

Example 11-1

Synthesis of 5-(1-(tert-butyl)-1H-pyrazol-4-yl)-6-isopropyl-[1,2,4]triazolo[1,5-a]pyrimidin-7(4H)-one Method A:

A 5 mL microwave vial was charged with 5-chloro-6-isopropyl-[1,2,4]triazolo[1,5-a]pyrimidin-7(4H)-one (40 mg, 0.188 mmol), 1-(tert-butyl)-4-(4,4,5,5-tetramethyl-1,3,2-dioxaborolan-2-yl)-1H-pyrazole (70.6 mg, 0.282 mmol), 1,1'-bis(diphenylphosphino)ferrocene-palladium(II)dichloride dichloromethane complex (15.4 mg, 0.019 mmol) and dioxane (1.5 ml). An aqueous solution of potassium carbonate (0.282 ml, 0.564 mmol) was added, the vial capped, and the contents heated to 110° C. for 3 hours. The mixture was concentrated, diluted with chloroform/isopropanol—3:1 (5 mL), washed with hydrochloric acid (1M, 2×5 mL), dried (MgSO$_4$), filtered, and the solvent was evaporated under reduced pressure. The resulting residue was taken up in DMSO, filtered and purified by mass triggered reverse phase HPLC (MeCN/water with 0.1% TFA modifier, linear gradient) to afford 5-(1-(tert-butyl)-1H-pyrazol-4-yl)-6-isopropyl-[1,2,4]triazolo[1,5-a]pyrimidin-7(4H)-one as a white solid. $^1$H NMR (600 MHz, DMSO-d$_6$): δ 12.79 (br s, 1H); 8.16 (d, J=13.0 Hz, 2H); 7.70 (s, 1H); 3.02 (t, J=8.2 Hz, 1H); 1.54 (s, 9H); 1.28 (d, J=6.8 Hz, 6H).

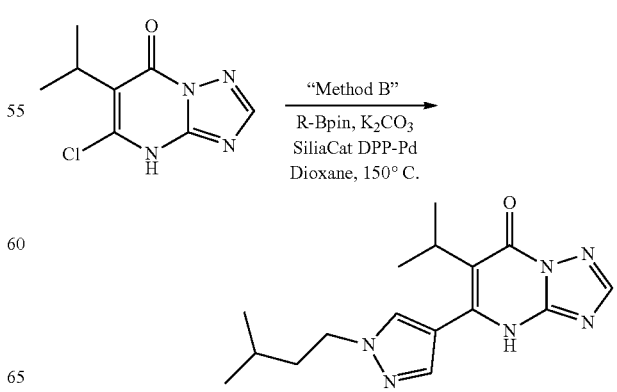

Example 11-2

Synthesis of 5-(1-isopentyl-1H-pyrazol-4-yl)-6-isopropyl-[1,2,4]triazolo[1,5-a]pyrimidin-7(4H)-one Method B:

A 5 mL microwave vial was charged with 5-chloro-6-isopropyl-[1,2,4]triazolo[1,5-a]pyrimidin-7(4H)-one (28 mg, 0.132 mmol), 1-isopentyl-4-(4,4,5,5-tetramethyl-1,3,2-dioxaborolan-2-yl)-1H-pyrazole (52.2 mg, 0.198 mmol), SiliaCat® DPP-Pd (132 mg, 0.033 mmol) and dioxane (1.8 ml). An aqueous solution of potassium carbonate (0.198 ml, 0.395 mmol) was added, the vial capped and the contents irradiated in the microwave at 150° C. for 20 minutes. The mixture was cooled, diluted with dichloromethane (5 mL), washed with water (5 mL), and the organic layer collected using a phase separator column (25 mL). The organic layer was concentrated, taken up in DMSO, filtered and purified by mass triggered reverse phase HPLC (MeCN/water with 0.1% TFA modifier, linear gradient) to afford 5-(1-isopentyl-1H-pyrazol-4-yl)-6-isopropyl-[1,2,4]triazolo[1,5-a]pyrimidin-7(4H)-one as a white solid. $^1$H NMR (600 MHz, DMSO-$d_6$): δ 12.85 (br s, 1H); 8.15 (s, 1H); 8.12 (s, 1H); 7.68 (s, 1H); 4.17 (t, J=7.3 Hz, 2H); 3.01-2.96 (m, 1H); 1.68 (q, J=7.1 Hz, 2H); 1.52-1.45 (m, 1H); 1.26 (d, J=6.9 Hz, 6H); 0.88 (d, J=6.6 Hz, 6H).

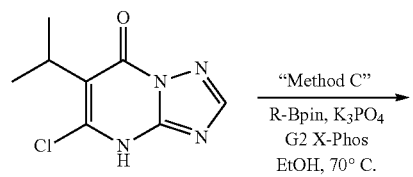

"Method C"
R-Bpin, K₃PO₄
G2 X-Phos
EtOH, 70° C.

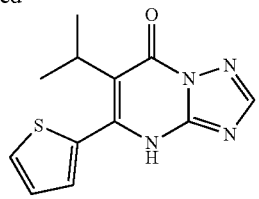

Example 11-3

Synthesis of 6-isopropyl-5-(thiophen-2-yl)-[1,2,4]triazolo[1,5-a]pyrimidin-7(4H)-one Method C:

A 5 mL microwave vial was charged with 5-chloro-6-isopropyl-[1,2,4]triazolo[1,5-a]pyrimidin-7(4H)-one (21.26 mg, 0.1 mmol), thiophen-2-ylboronic acid (38.4 mg, 0.300 mmol), chloro(2-dicyclohexylphosphino-2',4',6'-triisopropyl-1,1'-biphenyl)[2-(2'-amino-1,1'-biphenyl)]palladium(II) (15.74 mg, 0.020 mmol) and ethanol (1.25 ml). An aqueous solution of potassium phosphate tribasic (0.300 ml, 0.300 mmol) was added, the vial capped, and the contents heated to 70° C. for 16 hours. The mixture was concentrated, diluted with chloroform/isopropanol—3:1 (5 mL), washed with hydrochloric acid (1M, 5 mL), and the organic layer collected using a phase separator column (25 mL). The reaction mixture was concentrated, taken up in DMSO, filtered and purified by mass triggered reverse phase HPLC (MeCN/water with 0.1% TFA modifier, linear gradient) to afford 6-isopropyl-5-(thiophen-2-yl)-[1,2,4]triazolo[1,5-a]pyrimidin-7(4H)-one as a white solid. $^1$H NMR (600 MHz, DMSO-$d_6$): δ 13.19 (br s, 1H); 8.21 (br s, 1H); 7.81 (s, 1H); 7.35 (s, 1H); 7.19 (s, 1H); 2.95-2.85 (m, 1H); 1.24 (d, J=6.9 Hz, 6H).

The following compounds (Table 2) were synthesized as described;

TABLE 2

| Ex. No. | Structure | Name | Exact Mass [M + H]+ | Method | IC50 (nM) |
|---|---|---|---|---|---|
| 11-145 | 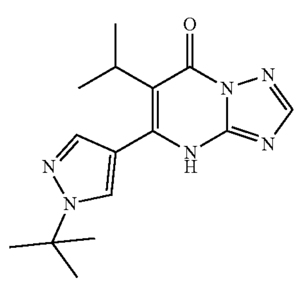 [SMILES: CC(C)c1c(-c2cnn(C(C)(C)C)c2)[nH]c2ncnn2c1=O] | 5-(1-tert-butyl-1H-pyrazol-4-yl)-6-(1-methylethyl)[1,2,4]triazolo[1,5-a]pyrimidin-7(4H)-one | Calc'd 301, found 301 | A | 5.081 |
| 11-146 | 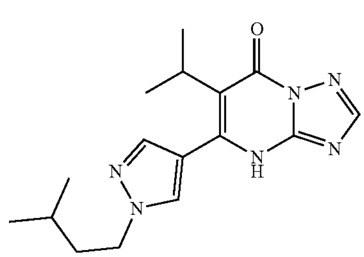 [SMILES: CC(C)CCn1cc(-c2[nH]c3ncnn3c(=O)c2C(C)C)cn1] | 5-[1-(3-methylbutyl)-1H-pyrazol-4-yl]-6-(1-methylethyl)[1,2,4]triazolo[1,5-a]pyrimidin-7(4H)-one | Calc'd 315, found 315 | B | 5.222 |

TABLE 2-continued

| Ex. No. | Structure | Name | Exact Mass [M + H]+ | Method | IC50 (nM) |
|---|---|---|---|---|---|
| 11-147 | 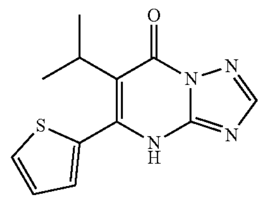 [SMILES: CC(C)c1c(-c2cccs2)[nH]c2ncnn2c1=O] | 6-(1-methylethyl)-5-thiophen-2-yl[1,2,4]triazolo[1,5-a]pyrimidin-7(4H)-one | Calc'd 261, found 261 | C | 413.2 |
| 11-4 | 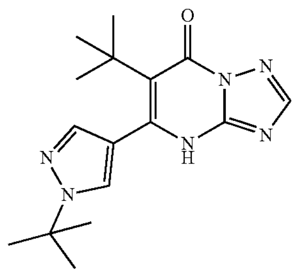 [SMILES: CC(C)(C)c1c(-c2cnn(C(C)(C)C)c2)[nH]c2ncnn2c1=O] | 6-tert-butyl-5-(1-tert-butyl-1H-pyrazol-4-yl)[1,2,4]triazolo[1,5-a]pyrimidin-7(4H)-one | Calc'd 315, found 315 | A | 904.5 |
| 11-5 | 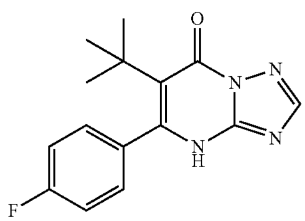 [SMILES: CC(C)(C)c1c(-c2ccc(F)cc2)[nH]c2ncnn2c1=O] | 6-tert-butyl-5-(4-fluorophenyl)[1,2,4]triazolo[1,5-a]pyrimidin-7(4H)-one | Calc'd 287, found 287 | A | 5401 |
| 11-6 | 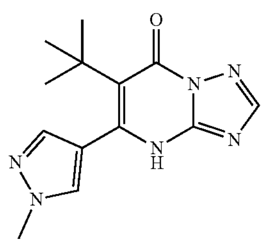 [SMILES: Cn1cc(-c2[nH]c3ncnn3c(=O)c2C(C)(C)C)cn1] | 6-tert-butyl-5-(1-methyl-1H-pyrazol-4-yl)[1,2,4]triazolo[1,5-a]pyrimidin-7(4H)-one | Calc'd 273, found 273 | A | 1268 |
| 11-7 | 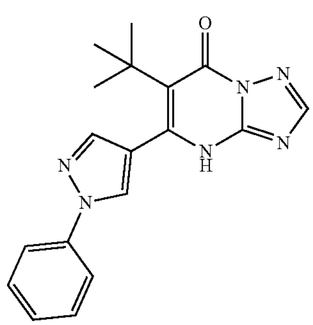 [SMILES: CC(C)(C)c1c(-c2cnn(-c3ccccc3)c2)[nH]c2ncnn2c1=O] | 6-tert-butyl-5-(1-phenyl-1H-pyrazol-4-yl)[1,2,4]triazolo[1,5-a]pyrimidin-7(4H)-one | Calc'd 335, found 335 | A | 771.9 |
| 11-8 | 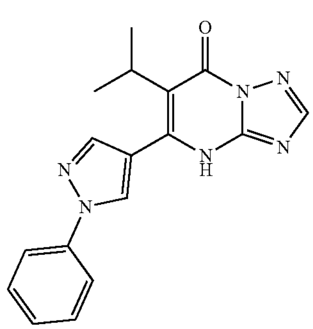 [SMILES: CC(C)c1c(-c2cnn(-c3ccccc3)c2)[nH]c2ncnn2c1=O] | 6-(1-methylethyl)-5-(1-phenyl-1H-pyrazol-4-yl)[1,2,4]triazolo[1,5-a]pyrimidin-7(4H)-one | Calc'd 321, found 321 | A | 6.276 |

TABLE 2-continued

| Ex. No. | Structure | Name | Exact Mass [M + H]+ | Method | IC50 (nM) |
| --- | --- | --- | --- | --- | --- |
| 11-9 | 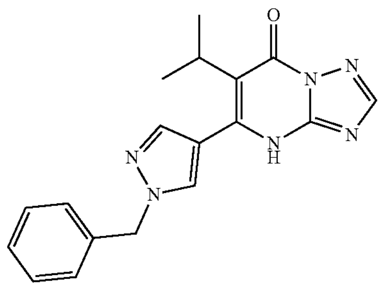 [SMILES: CC(C)c1c(-c2cnn(Cc3ccccc3)c2)[nH]c2ncnn2c1=O] | 5-(1-benzyl-1H-pyrazol-4-yl)-6-(1-methylethyl)[1,2,4]triazolo[1,5-a]pyrimidin-7(4H)-one | Calc'd 335, found 335 | B | 7.296 |
| 11-10 | 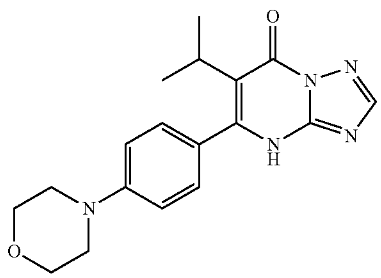 [SMILES: CC(C)c1c(-c2ccc(N3CCOCC3)cc2)[nH]c2ncnn2c1=O] | 6-(1-methylethyl)-5-(4-morpholin-4-ylphenyl)[1,2,4]triazolo[1,5-a]pyrimidin-7(4H)-one | Calc'd 340, found 340 | B | 7.52 |
| 11-11 | 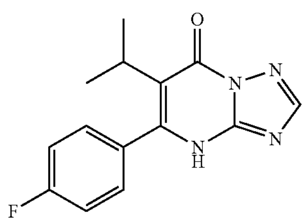 [SMILES: CC(C)c1c(-c2ccc(F)cc2)[nH]c2ncnn2c1=O] | 5-(4-fluorophenyl)-6-(1-methylethyl)[1,2,4]triazolo[1,5-a]pyrimidin-7(4H)-one | Calc'd 273, found 273 | B | 159.8 |
| 11-12 | 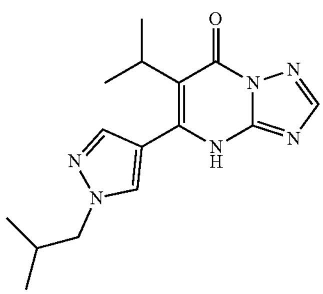 [SMILES: CC(C)Cn1cc(-c2[nH]c3ncnn3c(=O)c2C(C)C)cn1] | 6-(1-methylethyl)-5-[1-(2-methylpropyl)-1H-pyrazol-4-yl][1,2,4]triazolo[1,5-a]pyrimidin-7(4H)-one | Calc'd 301, found 301 | B | 5.081 |
| 11-13 | 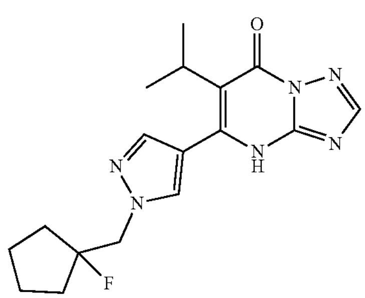 [SMILES: CC(C)c1c(-c2cnn(CC3(F)CCCC3)c2)[nH]c2ncnn2c1=O] | 5-{1-[(1-fluorocyclopentyl)methyl]-1H-pyrazol-4-yl}-6-(1-methylethyl)[1,2,4]triazolo[1,5-a]pyrimidin-7(4H)-one | Calc'd 345, found 345 | B | 5.081 |

TABLE 2-continued

| Ex. No. | Structure | Name | Exact Mass [M + H]+ | Method | IC50 (nM) |
|---|---|---|---|---|---|
| 11-14 | 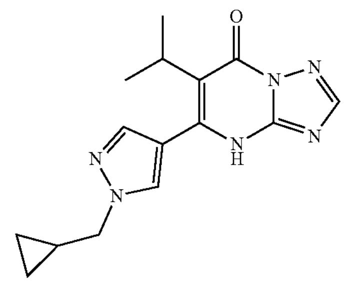 [SMILES: CC(C)c1c(-c2cnn(CC3CC3)c2)[nH]c2ncnn2c1=O] | 5-[1-(cyclopropylmethyl)-1H-pyrazol-4-yl]-6-(1-methylethyl)[1,2,4]triazolo[1,5-a]pyrimidin-7(4H)-one | Calc'd 299, found 299 | B | 5.081 |
| 11-15 | 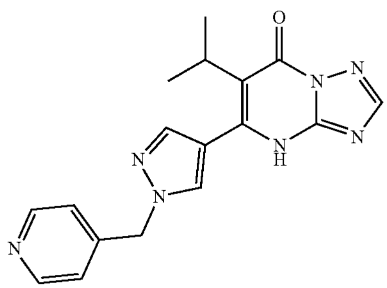 [SMILES: CC(C)c1c(-c2cnn(Cc3ccncc3)c2)[nH]c2ncnn2c1=O] | 6-(1-methylethyl)-5-[1-(pyridin-4-ylmethyl)-1H-pyrazol-4-yl][1,2,4]triazolo[1,5-a]pyrimidin-7(4H)-one | Calc'd 336, found 336 | B | 7.502 |
| 11-16 | 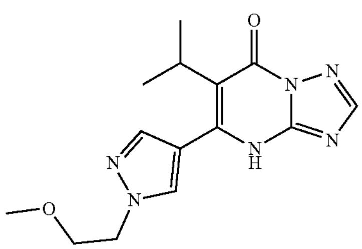 [SMILES: COCCn1cc(-c2[nH]c3ncnn3c(=O)c2C(C)C)cn1] | 5-[1-(2-methoxyethyl)-1H-pyrazol-4-yl]-6-(1-methylethyl)[1,2,4]triazolo[1,5-a]pyrimidin-7(4H)-one | Calc'd 303, found 303 | B | 5.73 |
| 11-17 | 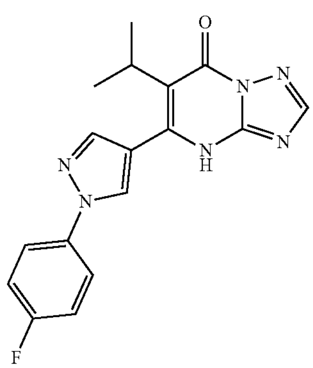 [SMILES: CC(C)c1c(-c2cnn(-c3ccc(F)cc3)c2)[nH]c2ncnn2c1=O] | 5-[1-(4-fluorophenyl)-1H-pyrazol-4-yl]-6-(1-methylethyl)[1,2,4]triazolo[1,5-a]pyrimidin-7(4H)-one | Calc'd 339, found 339 | B | 6.471 |
| 11-18 | 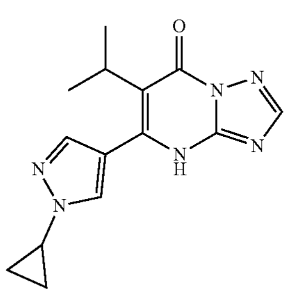 [SMILES: CC(C)c1c(-c2cnn(C3CC3)c2)[nH]c2ncnn2c1=O] | 5-(1-cyclopropyl-1H-pyrazol-4-yl)-6-(1-methylethyl)[1,2,4]triazolo[1,5-a]pyrimidin-7(4H)-one | Calc'd 285, found 285 | B | 5.737 |

TABLE 2-continued

| Ex. No. | Structure | Name | Exact Mass [M + H]+ | Method | IC50 (nM) |
|---|---|---|---|---|---|
| 11-19 | 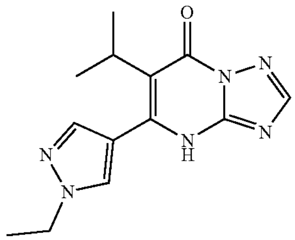 [SMILES: CCn1cc(-c2[nH]c3ncnn3c(=O)c2C(C)C)cn1] | 5-(1-ethyl-1H-pyrazol-4-yl)-6-(1-methylethyl)[1,2,4]triazolo[1,5-a]pyrimidin-7(4H)-one | Calc'd 273, found 273 | B | 6.271 |
| 11-20 | 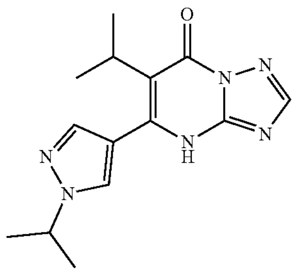 [SMILES: CC(C)c1c(-c2cnn(C(C)C)c2)[nH]c2ncnn2c1=O] | 6-(1-methylethyl)-5-[1-(1-methylethyl)-1H-pyrazol-4-yl][1,2,4]triazolo[1,5-a]pyrimidin-7(4H)-one | Calc'd 287, found 287 | B | 5.081 |
| 11-21 | 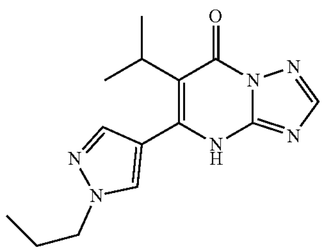 [SMILES: CCCn1cc(-c2[nH]c3ncnn3c(=O)c2C(C)C)cn1] | 6-(1-methylethyl)-5-(1-propyl-1H-pyrazol-4-yl)[1,2,4]triazolo[1,5-a]pyrimidin-7(4H)-one | Calc'd 287, found 287 | B | 5.081 |
| 11-22 | 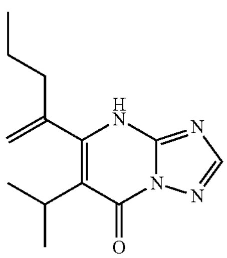 [SMILES: C=C(CCC)c1[nH]c2ncnn2c(=O)c1C(C)C] | 6-(1-methylethyl)-5-(1-methylidene-butyl)[1,2,4]triazolo[1,5-a]pyrimidin-7(4H)-one | Calc'd 247, found 247 | B | 807.9 |
| 11-23 | 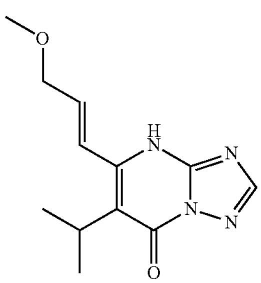 [SMILES: COC/C=C/c1[nH]c2ncnn2c(=O)c1C(C)C] | 5-[(1E)-3-methoxyprop-1-en-1-yl]-6-(1-methylethyl)[1,2,4]triazolo[1,5-a]pyrimidin-7(4H)-one | Calc'd 249, found 249 | B | 27.74 |
| 11-24 | 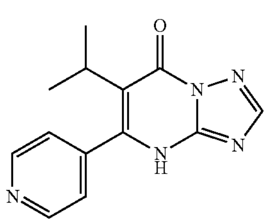 [SMILES: CC(C)c1c(-c2ccncc2)[nH]c2ncnn2c1=O] | 6-(1-methylethyl)-5-pyridin-4-yl[1,2,4]triazolo[1,5-a]pyrimidin-7(4H)-one | Calc'd 256, found 256 | B | 41.17 |

TABLE 2-continued

| Ex. No. | Structure | Name | Exact Mass [M + H]+ | Method | IC50 (nM) |
|---|---|---|---|---|---|
| 11-25 | 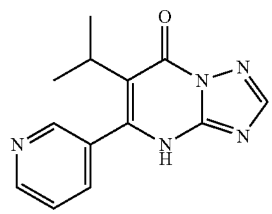 [SMILES: CC(C)c1c(-c2cccnc2)[nH]c2ncnn2c1=O] | 6-(1-methylethyl)-5-pyridin-3-yl[1,2,4]triazolo[1,5-a]pyrimidin-7(4H)-one | Calc'd 256, found 256 | B | 47.08 |
| 11-26 | 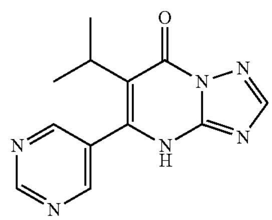 [SMILES: CC(C)c1c(-c2cncnc2)[nH]c2ncnn2c1=O] | 6-(1-methylethyl)-5-pyrimidin-5-yl[1,2,4]triazolo[1,5-a]pyrimidin-7(4H)-one | Calc'd 257, found 257 | B | 103 |
| 11-27 | 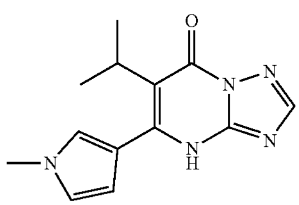 [SMILES: CC(C)c1c(-c2ccn(C)c2)[nH]c2ncnn2c1=O] | 6-(1-methylethyl)-5-(1-methyl-1H-pyrrol-3-yl)[1,2,4]triazolo[1,5-a]pyrimidin-7(4H)-one | Calc'd 258, found 258 | B | 17.87 |
| 11-28 | 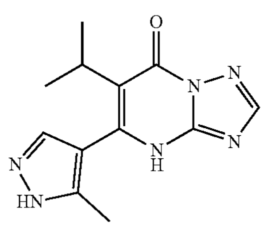 [SMILES: Cc1[nH]ncc1-c1[nH]c2ncnn2c(=O)c1C(C)C] | 6-(1-methylethyl)-5-(5-methyl-1H-pyrazol-4-yl)[1,2,4]triazolo[1,5-a]pyrimidin-7(4H)-one | Calc'd 259, found 259 | B | 154.6 |
| 11-29 | 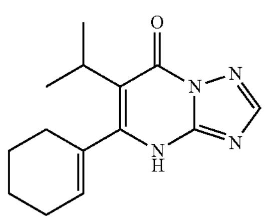 [SMILES: CC(C)c1c(C2=CCCCC2)[nH]c2ncnn2c1=O] | 5-cyclohex-1-en-1-yl-6-(1-methylethyl)[1,2,4]triazolo[1,5-a]pyrimidin-7(4H)-one | Calc'd 259, found 259 | B | 399.2 |
| 11-30 | 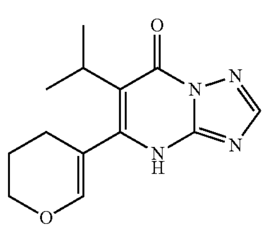 [SMILES: CC(C)c1c(C2=COCCC2)[nH]c2ncnn2c1=O] | 5-(3,4-dihydro-2H-pyran-5-yl)-6-(1-methylethyl)[1,2,4]triazolo[1,5-a]pyrimidin-7(4H)-one | Calc'd 261, found 261 | B | 253.9 |
| 11-31 | 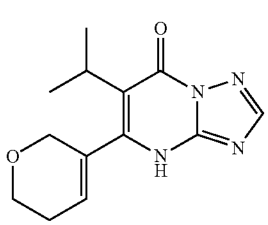 [SMILES: CC(C)c1c(C2=CCCOC2)[nH]c2ncnn2c1=O] | 5-(5,6-dihydro-2H-pyran-3-yl)-6-(1-methylethyl)[1,2,4]triazolo[1,5-a]pyrimidin-7(4H)-one | Calc'd 261, found 261 | B | 372.3 |

TABLE 2-continued

| Ex. No. | Structure | Name | Exact Mass [M + H]+ | Method | IC50 (nM) |
|---|---|---|---|---|---|
| 11-32 | 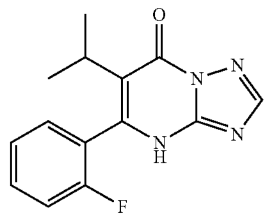 [SMILES: CC(C)c1c(-c2ccccc2F)[nH]c2ncnn2c1=O] | 5-(2-fluorophenyl)-6-(1-methylethyl)[1,2,4]triazolo[1,5-a]pyrimidin-7(4H)-one | Calc'd 273, found 273 | B | 393.5 |
| 11-33 | 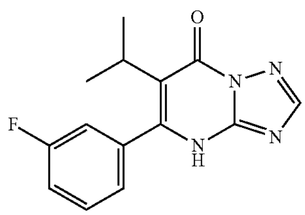 | 5-(3-fluorophenyl)-6-(1-methylethyl)[1,2,4]triazolo[1,5-a]pyrimidin-7(4H)-one | Calc'd 273, found 273 | B | 135.8 |
| 11-34 | 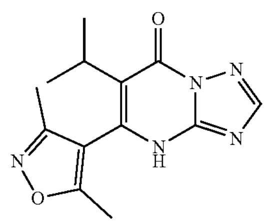 [SMILES: Cc1noc(C)c1-c1[nH]c2ncnn2c(=O)c1C(C)C] | 5-(3,5-dimethylisoxazol-4-yl)-6-(1-methylethyl)[1,2,4]triazolo[1,5-a]pyrimidin-7(4H)-one | Calc'd 274, found 274 | B | 11090 |
| 11-35 | 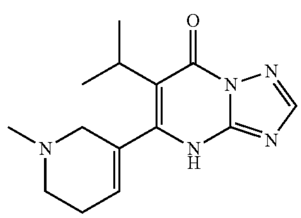 [SMILES: CC(C)c1c(C2=CCCN(C)C2)[nH]c2ncnn2c1=O] | 6-(1-methylethyl)-5-(1-methyl-1,2,5,6-tetrahydropyridin-3-yl)[1,2,4]triazolo[1,5-a]pyrimidin-7(4H)-one | Calc'd 274, found 274 | B | 506.2 |
| 11-36 | 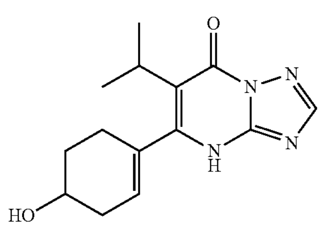 [SMILES: CC(C)c1c(C2=CCC(O)CC2)[nH]c2ncnn2c1=O] | 5-(4-hydroxycyclohex-1-en-1-yl)-6-(1-methylethyl)[1,2,4]triazolo[1,5-a]pyrimidin-7(4H)-one | Calc'd 275, found 275 | B | 136.8 |
| 11-37 | 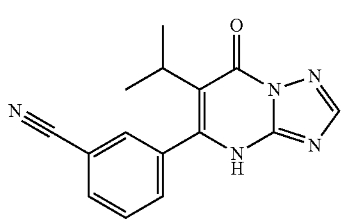 [SMILES: CC(C)c1c(-c2cccc(C#N)c2)[nH]c2ncnn2c1=O] | 3-[6-(1-methylethyl)-7-oxo-4,7-dihydro[1,2,4]triazolo[1,5-a]pyrimidin-5-yl]benzonitrile | Calc'd 280, found 280 | B | 21.59 |
| 11-38 | 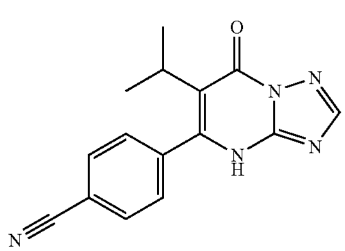 [SMILES: CC(C)c1c(-c2ccc(C#N)cc2)[nH]c2ncnn2c1=O] | 4-[6-(1-methylethyl)-7-oxo-4,7-dihydro[1,2,4]triazolo[1,5-a]pyrimidin-5-yl]benzonitrile | Calc'd 280, found 280 | B | 21.59 |

TABLE 2-continued

| Ex. No. | Structure | Name | Exact Mass [M + H]+ | Method | IC50 (nM) |
|---|---|---|---|---|---|
| 11-39 | 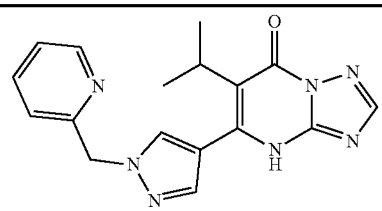 | 6-(1-methylethyl)-5-[1-(pyridin-2-ylmethyl)-1H-pyrazol-4-yl][1,2,4]triazolo[1,5-a]pyrimidin-7(4H)-one | Calc'd 336, found 336 | B | 5.826 |
| 11-40 | 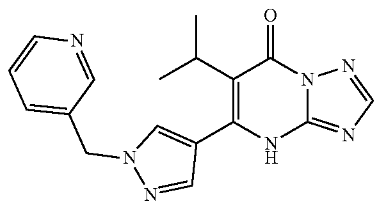 [SMILES: CC(C)c1c(-c2cnn(Cc3cccnc3)c2)[nH]c2ncnn2c1=O] | 6-(1-methylethyl)-5-[1-(pyridin-3-ylmethyl)-1H-pyrazol-4-yl][1,2,4]triazolo[1,5-a]pyrimidin-7(4H)-one | Calc'd 336, found 336 | B | 5.771 |
| 11-41 | 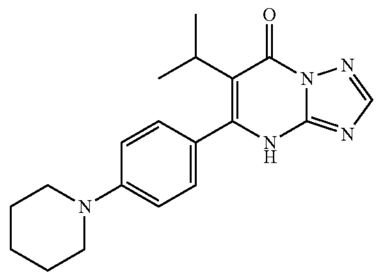 [SMILES: CC(C)c1c(-c2ccc(N3CCCCC3)cc2)[nH]c2ncnn2c1=O] | 6-(1-methylethyl)-5-(4-piperidin-1-ylphenyl)[1,2,4]triazolo[1,5-a]pyrimidin-7(4H)-one | Calc'd 338, found 338 | B | 11.8 |
| 11-42 | 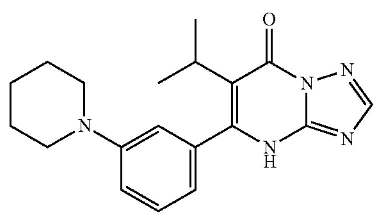 [SMILES: CC(C)c1c(-c2cccc(N3CCCCC3)c2)[nH]c2ncnn2c1=O] | 6-(1-methylethyl)-5-(3-piperidin-1-ylphenyl)[1,2,4]triazolo[1,5-a]pyrimidin-7(4H)-one | Calc'd 338, found 338 | B | 74.65 |
| 11-43 | 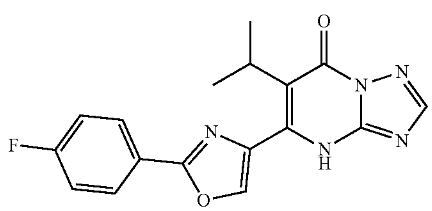 [SMILES: CC(C)c1c(-c2coc(-c3ccc(F)cc3)n2)[nH]c2ncnn2c1=O] | 5-[2-(4-fluorophenyl)-1,3-oxazol-4-yl]-6-(1-methylethyl)[1,2,4]triazolo[1,5-a]pyrimidin-7(4H)-one | Calc'd 340, found 340 | B | 23.78 |
| 11-44 | 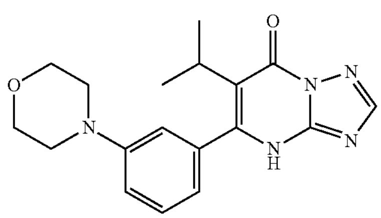 [SMILES: CC(C)c1c(-c2cccc(N3CCOCC3)c2)[nH]c2ncnn2c1=O] | 6-(1-methylethyl)-5-(3-morpholin-4-ylphenyl)[1,2,4]triazolo[1,5-a]pyrimidin-7(4H)-one | Calc'd 340, found 340 | B | 46.26 |
| 11-45 | 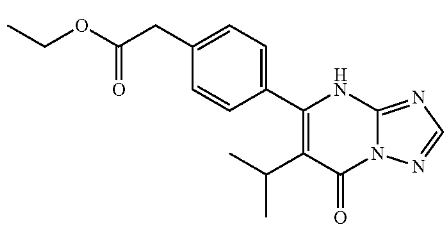 [SMILES: CCOC(=O)Cc1ccc(-c2[nH]c3ncnn3c(=O)c2C(C)C)cc1] | ethyl {4-[6-(1-methylethyl)-7-oxo-4,7-dihydro[1,2,4]triazolo[1,5-a]pyrimidin-5-yl]phenyl}acetate | Calc'd 341, found 341 | B | 17.44 |

TABLE 2-continued

| Ex. No. | Structure | Name | Exact Mass [M + H]+ | Method | IC50 (nM) |
|---|---|---|---|---|---|
| 11-46 | 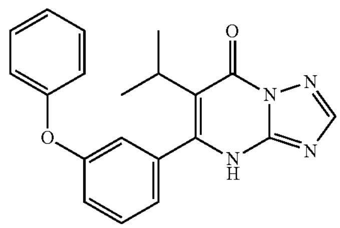 [SMILES: CC(C)c1c(-c2cccc(Oc3ccccc3)c2)[nH]c2ncnn2c1=O] | 6-(1-methylethyl)-5-(3-phenoxyphenyl)[1,2,4]triazolo[1,5-a]pyrimidin-7(4H)-one | Calc'd 347, found 347 | B | 302.7 |
| 11-47 | 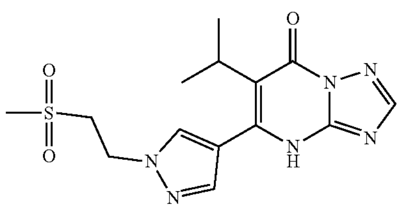 [SMILES: CC(C)c1c(-c2cnn(CCS(C)(=O)=O)c2)[nH]c2ncnn2c1=O] | 6-(1-methylethyl)-5-{1-[2-(methylsulfonyl)ethyl]-1H-pyrazol-4-yl}[1,2,4]triazolo[1,5-a]pyrimidin-7(4H)-one | Calc'd 351, found 351 | B | 6.929 |
| 11-48 | 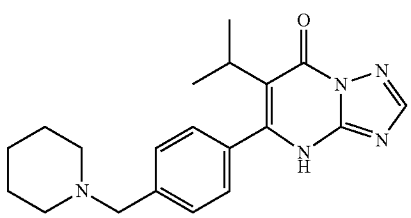 [SMILES: CC(C)c1c(-c2ccc(CN3CCCCC3)cc2)[nH]c2ncnn2c1=O] | 6-(1-methylethyl)-5-[4-(piperidin-1-ylmethyl)phenyl][1,2,4]triazolo[1,5-a]pyrimidin-7(4H)-one | Calc'd 352, found 352 | B | 16.78 |
| 11-49 | 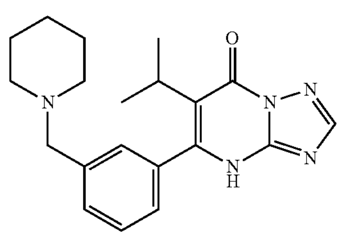 [SMILES: CC(C)c1c(-c2cccc(CN3CCCCC3)c2)[nH]c2ncnn2c1=O] | 6-(1-methylethyl)-5-[3-(piperidin-1-ylmethyl)phenyl][1,2,4]triazolo[1,5-a]pyrimidin-7(4H)-one | Calc'd 352, found 352 | B | 33.23 |
| 11-50 | 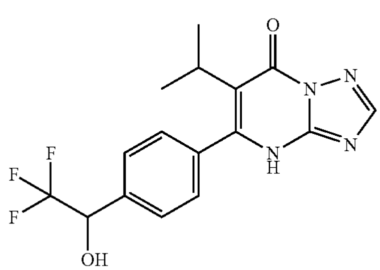 [SMILES: CC(C)c1c(-c2ccc(C(O)C(F)(F)F)cc2)[nH]c2ncnn2c1=O] | 6-(1-methylethyl)-5-[4-(2,2,2-trifluoro-1-hydroxyethyl)-phenyl][1,2,4]triazolo[1,5-a]pyrimidin-7(4H)-one | Calc'd 353, found 353 | B | 20.06 |
| 11-51 | 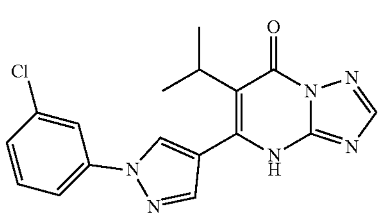 [SMILES: CC(C)c1c(-c2cnn(-c3cccc(Cl)c3)c2)[nH]c2ncnn2c1=O] | 5-[1-(3-chlorophenyl)-1H-pyrazol-4-yl]-6-(1-methylethyl)[1,2,4]triazolo[1,5-a]pyrimidin-7(4H)-one | Calc'd 355, found 355 | B | 9.665 |

TABLE 2-continued

| Ex. No. | Structure | Name | Exact Mass [M + H]+ | Method | IC50 (nM) |
|---|---|---|---|---|---|
| 11-52 | 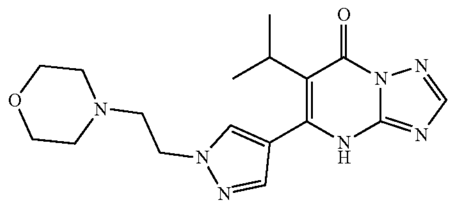 [SMILES: CC(C)c1c(-c2cnn(CCN3CCOCC3)c2)[nH]c2ncnn2c1=O] | 6-(1-methylethyl)-5-[1-(2-morpholin-4-ylethyl)-1H-pyrazol-4-yl][1,2,4]triazolo[1,5-a]pyrimidin-7(4H)-one | Calc'd 358, found 358 | B | 6.962 |
| 11-53 | 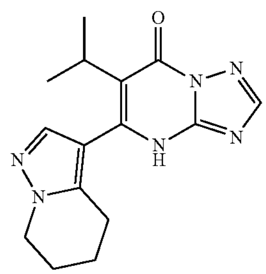 [SMILES: CC(C)c1c(-c2cnn3c2CCCC3)[nH]c2ncnn2c1=O] | 6-(1-methylethyl)-5-(4,5,6,7-tetrahydropyrazolo[1,5-a]pyridin-3-yl)[1,2,4]triazolo[1,5-a]pyrimidin-7(4H)-one | Calc'd 299, found 299 | B | 75.06 |
| 11-54 | 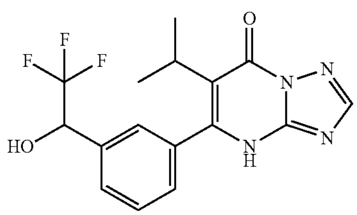 [SMILES: CC(C)c1c(-c2cccc(C(O)C(F)(F)F)c2)[nH]c2ncnn2c1=O] | 6-(1-methylethyl)-5-[3-(2,2,2-trifluoro-1-hydroxyethyl)phenyl][1,2,4]triazolo[1,5-a]pyrimidin-7(4H)-one | Calc'd 353, found 353 | B | 31.41 |
| 11-55 | 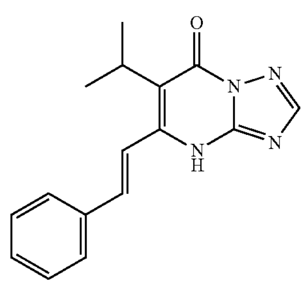 [SMILES: CC(C)c1c(/C=C/c2ccccc2)[nH]c2ncnn2c1=O] | 6-(1-methylethyl)-5-[(E)-2-phenylethenyl][1,2,4]triazolo[1,5-a]pyrimidin-7(4H)-one | Calc'd 281, found 281 | B | 9.452 |
| 11-56 | 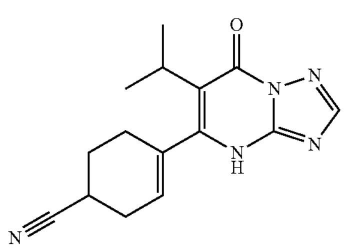 [SMILES: CC(C)c1c(C2=CCC(C#N)CC2)[nH]c2ncnn2c1=O] | 4-[6-(1-methylethyl)-7-oxo-4,7-dihydro[1,2,4]triazolo[1,5-a]pyrimidin-5-yl]cyclohex-3-ene-1-carbonitrile | Calc'd 284, found 284 | B | 110.3 |
| 11-57 | 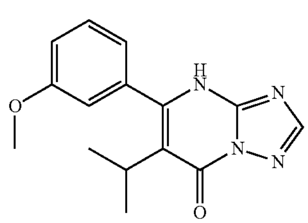 [SMILES: COc1cccc(-c2[nH]c3ncnn3c(=O)c2C(C)C)c1] | 5-(3-methoxyphenyl)-6-(1-methylethyl)[1,2,4]triazolo[1,5-a]pyrimidin-7(4H)-one | Calc'd 285, found 285 | B | 55.37 |

TABLE 2-continued

| Ex. No. | Structure | Name | Exact Mass [M + H]+ | Method | IC50 (nM) |
|---|---|---|---|---|---|
| 11-58 | 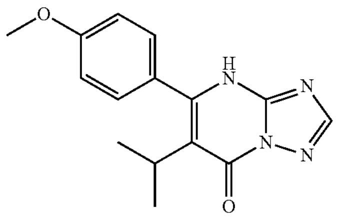 [SMILES: COc1ccc(-c2[nH]c3ncnn3c(=O)c2C(C)C)cc1] | 5-(4-methoxyphenyl)-6-(1-methylethyl)[1,2,4]triazolo[1,5-a]pyrimidin-7(4H)-one | Calc'd 285, found 285 | B | 37.31 |
| 11-59 | 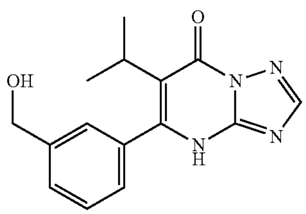 [SMILES: CC(C)c1c(-c2cccc(CO)c2)[nH]c2ncnn2c1=O] | 5-[3-(hydroxymethyl)phenyl]-6-(1-methylethyl)[1,2,4]triazolo[1,5-a]pyrimidin-7(4H)-one | Calc'd 285, found 285 | B | 26.52 |
| 11-60 | 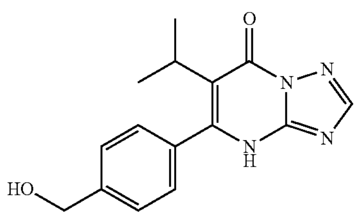 [SMILES: CC(C)c1c(-c2ccc(CO)cc2)[nH]c2ncnn2c1=O] | 5-[4-(hydroxymethyl)phenyl]-6-(1-methylethyl)[1,2,4]triazolo[1,5-a]pyrimidin-7(4H)-one | Calc'd 285, found 285 | B | 13.52 |
| 11-61 | 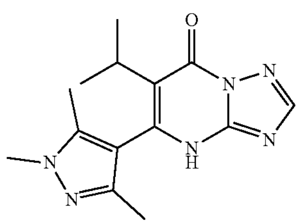 [SMILES: Cc1nn(C)c(C)c1-c1[nH]c2ncnn2c(=O)c1C(C)C] | 6-(1-methylethyl)-5-(1,3,5-trimethyl-1H-pyrazol-4-yl)[1,2,4]triazolo[1,5-a]pyrimidin-7(4H)-one | Calc'd 287, found 287 | B | 2168 |
| 11-62 | 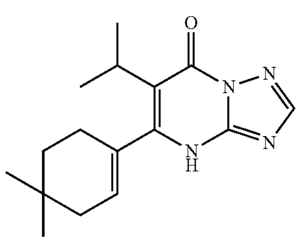 [SMILES: CC(C)c1c(C2=CCC(C)(C)CC2)[nH]c2ncnn2c1=O] | 5-(4,4-dimethylcyclohex-1-en-1-yl)-6-(1-methylethyl)[1,2,4]triazolo[1,5-a]pyrimidin-7(4H)-one | Calc'd 287, found 287 | B | 1034 |
| 11-63 | 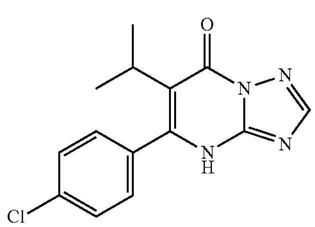 [SMILES: CC(C)c1c(-c2ccc(Cl)cc2)[nH]c2ncnn2c1=O] | 5-(4-chlorophenyl)-6-(1-methylethyl)[1,2,4]triazolo[1,5-a]pyrimidin-7(4H)-one | Calc'd 289, found 289 | B | 71.46 |
| 11-64 | 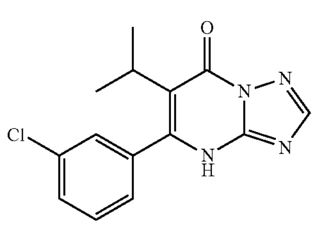 [SMILES: CC(C)c1c(-c2cccc(Cl)c2)[nH]c2ncnn2c1=O] | 5-(3-chlorophenyl)-6-(1-methylethyl)[1,2,4]triazolo[1,5-a]pyrimidin-7(4H)-one | Calc'd 289, found 289 | B | 91.81 |

TABLE 2-continued

| Ex. No. | Structure | Name | Exact Mass [M + H]+ | Method | IC50 (nM) |
|---|---|---|---|---|---|
| 11-65 | 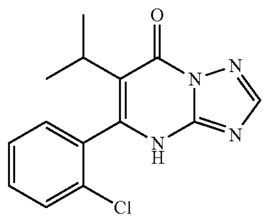 | 5-(2-chlorophenyl)-6-(1-methylethyl)[1,2,4]triazolo[1,5-a]pyrimidin-7(4H)-one | Calc'd 289, found 289 | B | 3365 |
| 11-66 | 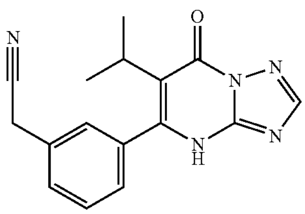 [SMILES: CC(C)c1c(-c2cccc(CC#N)c2)[nH]c2ncnn2c1=O] | {3-[6-(1-methylethyl)-7-oxo-4,7-dihydro[1,2,4]triazolo[1,5-a]pyrimidin-5-yl]phenyl}acetonitrile | Calc'd 294, found 294 | B | 8.926 |
| 11-67 | 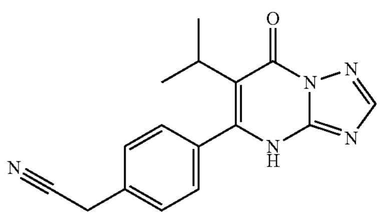 [SMILES: CC(C)c1c(-c2ccc(CC#N)cc2)[nH]c2ncnn2c1=O] | {4-[6-(1-methylethyl)-7-oxo-4,7-dihydro[1,2,4]triazolo[1,5-a]pyrimidin-5-yl]phenyl}acetonitrile | Calc'd 294, found 294 | B | 18.17 |
| 11-68 | 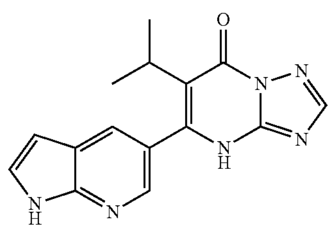 [SMILES: CC(C)c1c(-c2cnc3[nH]ccc3c2)[nH]c2ncnn2c1=O] | 6-(1-methylethyl)-5-(1H-pyrrolo[2,3-b]pyridin-5-yl)[1,2,4]triazolo[1,5-a]pyrimidin-7(4H)-one | Calc'd 295, found 295 | B | 20.04 |
| 11-69 | 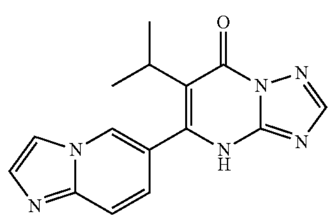 [SMILES: CC(C)c1c(-c2ccc3nccn3c2)[nH]c2ncnn2c1=O] | 5-imidazo[1,2-a]pyridin-6-yl-6-(1-methylethyl)[1,2,4]triazolo[1,5-a]pyrimidin-7(4H)-one | Calc'd 295, found 295 | B | 25.83 |
| 11-70 | 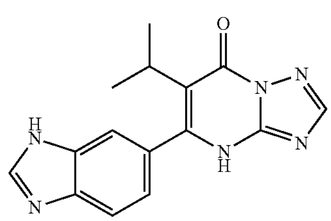 [SMILES: CC(C)c1c(-c2ccc3nc[nH]c3c2)[nH]c2ncnn2c1=O] | 5-(1H-benzimidazol-6-yl)-6-(1-methylethyl)[1,2,4]triazolo[1,5-a]pyrimidin-7(4H)-one | Calc'd 295, found 295 | B | 13.54 |
| 11-71 | 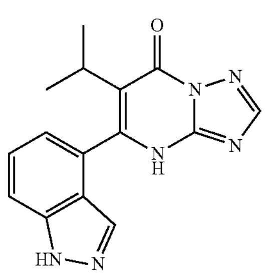 [SMILES: CC(C)c1c(-c2cccc3[nH]ncc23)[nH]c2ncnn2c1=O] | 5-(1H-indazol-4-yl)-6-(1-methylethyl)[1,2,4]triazolo[1,5-a]pyrimidin-7(4H)-one | Calc'd 295, found 295 | B | 208.3 |

TABLE 2-continued

| Ex. No. | Structure | Name | Exact Mass [M + H]+ | Method | IC50 (nM) |
|---|---|---|---|---|---|
| 11-72 | 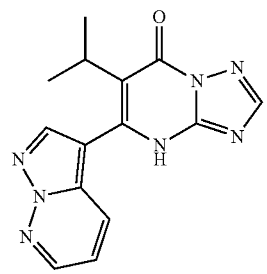 [SMILES: CC(C)c1c(-c2cnn3ncccc23)[nH]c2ncnn2c1=O] | 6-(1-methylethyl)-5-pyrazolo[1,5-b]pyridazin-3-yl[1,2,4]triazolo[1,5-a]pyrimidin-7(4H)-one | Calc'd 296, found 296 | B | 20.08 |
| 11-73 | 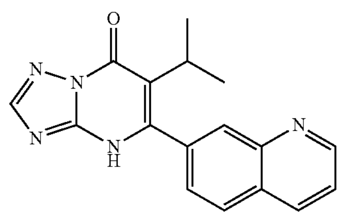 [SMILES: CC(C)c1c(-c2ccc3cccnc3c2)[nH]c2ncnn2c1=O] | 6-(1-methylethyl)-5-quinolin-7-yl[1,2,4]triazolo[1,5-a]pyrimidin-7(4H)-one | Calc'd 306, found 306 | B | 27.21 |
| 11-74 | 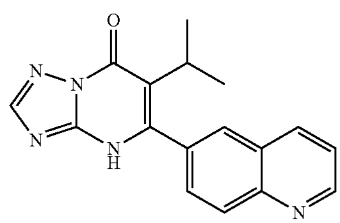 [SMILES: CC(C)c1c(-c2ccc3ncccc3c2)[nH]c2ncnn2c1=O] | 6-(1-methylethyl)-5-quinolin-6-yl[1,2,4]triazolo[1,5-a]pyrimidin-7(4H)-one | Calc'd 306, found 306 | B | 14.69 |
| 11-75 | 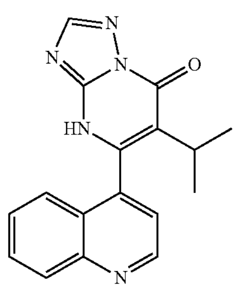 [SMILES: CC(C)c1c(-c2ccnc3ccccc23)[nH]c2ncnn2c1=O] | 6-(1-methylethyl)-5-quinolin-4-yl[1,2,4]triazolo[1,5-a]pyrimidin-7(4H)-one | Calc'd 306, found 306 | B | 903.6 |
| 11-76 | 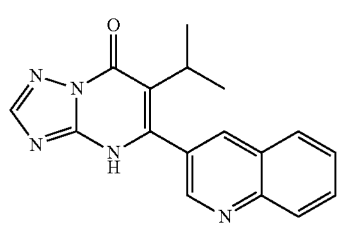 [SMILES: CC(C)c1c(-c2cnc3ccccc3c2)[nH]c2ncnn2c1=O] | 6-(1-methylethyl)-5-quinolin-3-yl[1,2,4]triazolo[1,5-a]pyrimidin-7(4H)-one | Calc'd 306, found 306 | B | 23.75 |
| 11-77 | 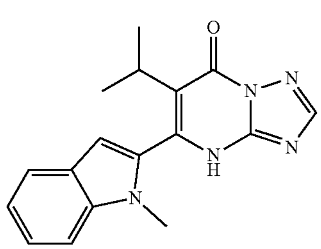 [SMILES: CC(C)c1c(-c2cc3ccccc3n2C)[nH]c2ncnn2c1=O] | 6-(1-methylethyl)-5-(1-methyl-1H-indol-2-yl)[1,2,4]triazolo[1,5-a]pyrimidin-7(4H)-one | Calc'd 308, found 308 | B | 1264 |

TABLE 2-continued

| Ex. No. | Structure | Name | Exact Mass [M + H]+ | Method | IC50 (nM) |
|---|---|---|---|---|---|
| 11-78 | 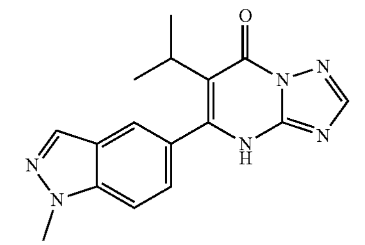 [SMILES: CC(C)c1c(-c2ccc3c(cnn3C)c2)[nH]c2ncnn2c1=O] | 6-(1-methylethyl)-5-(1-methyl-1H-indazol-5-yl)[1,2,4]triazolo[1,5-a]pyrimidin-7(4H)-one | Calc'd 309, found 309 | B | 10.44 |
| 11-79 | 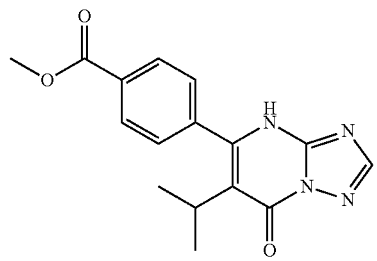 [SMILES: COC(=O)c1ccc(-c2[nH]c3ncnn3c(=O)c2C(C)C)cc1] | methyl 4-[6-(1-methylethyl)-7-oxo-4,7-dihydro[1,2,4]triazolo[1,5-a]pyrimidin-5-yl]benzoate | Calc'd 313, found 313 | B | 19.44 |
| 11-80 | 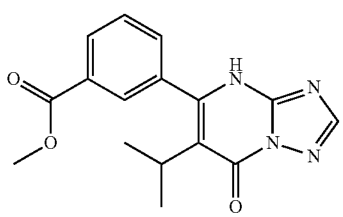 [SMILES: COC(=O)c1cccc(-c2[nH]c3ncnn3c(=O)c2C(C)C)c1] | methyl 3-[6-(1-methylethyl)-7-oxo-4,7-dihydro[1,2,4]triazolo[1,5-a]pyrimidin-5-yl]benzoate | Calc'd 313, found 313 | B | 34.24 |
| 11-81 | 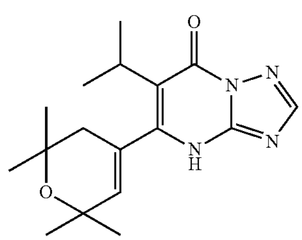 [SMILES: CC(C)c1c(C2=CC(C)(C)OC(C)(C)C2)[nH]c2ncnn2c1=O] | 6-(1-methylethyl)-5-(2,2,6,6-tetramethyl-3,6-dihydro-2H-pyran-4-yl)[1,2,4]triazolo[1,5-a]pyrimidin-7(4H)-one | Calc'd 317, found 317 | B | 305.5 |
| 11-82 | 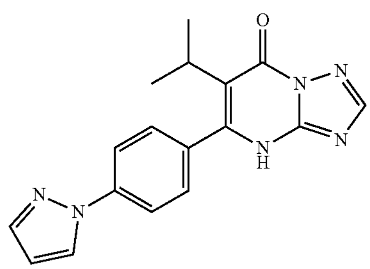 | 6-(1-methylethyl)-5-[4-(1H-pyrazol-1-yl)phenyl][1,2,4]triazolo[1,5-a]pyrimidin-7(4H)-one | Calc'd 321, found 321 | B | 8.783 |
| 11-83 | 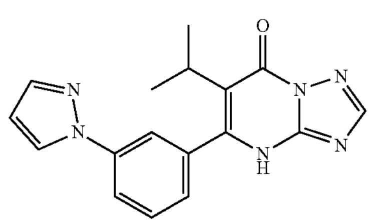 [SMILES: CC(C)c1c(-c2cccc(-n3cccn3)c2)[nH]c2ncnn2c1=O] | 6-(1-methylethyl)-5-[3-(1H-pyrazol-1-yl)phenyl][1,2,4]triazolo[1,5-a]pyrimidin-7(4H)-one | Calc'd 321, found 321 | B | 21.23 |

TABLE 2-continued

| Ex. No. | Structure | Name | Exact Mass [M + H]+ | Method | IC50 (nM) |
|---|---|---|---|---|---|
| 11-84 | 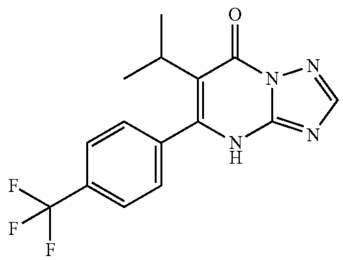 [SMILES: CC(C)c1c(-c2ccc(C(F)(F)F)cc2)[nH]c2ncnn2c1=O] | 6-(1-methylethyl)-5-[4-(trifluoromethyl)-phenyl][1,2,4]triazolo[1,5-a]pyrimidin-7(4H)-one | Calc'd 323, found 323 | B | 67.17 |
| 11-85 | 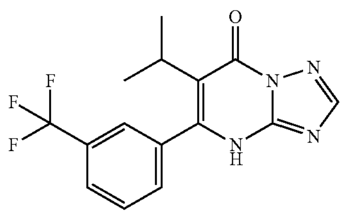 [SMILES: CC(C)c1c(-c2cccc(C(F)(F)F)c2)[nH]c2ncnn2c1=O] | 6-(1-methylethyl)-5-[3-(trifluoromethyl)phenyl][1,2,4]triazolo[1,5-a]pyrimidin-7(4H)-one | Calc'd 323, found 323 | B | 41.25 |
| 11-86 | 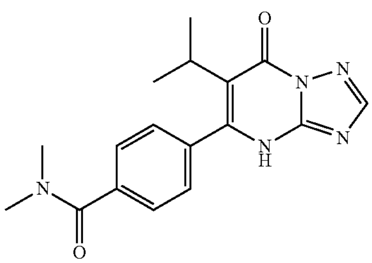 [SMILES: CC(C)c1c(-c2ccc(C(=O)N(C)C)cc2)[nH]c2ncnn2c1=O] | N,N-dimethyl-4-[6-(1-methylethyl)-7-oxo-4,7-dihydro[1,2,4]triazolo[1,5-a]pyrimidin-5-yl]benzamide | Calc'd 326, found 326 | B | 12.58 |
| 11-87 | 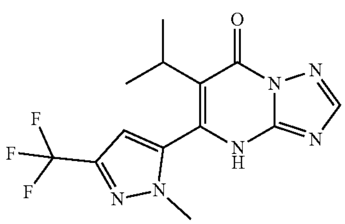 [SMILES: CC(C)c1c(-c2cc(C(F)(F)F)nn2C)[nH]c2ncnn2c1=O] | 6-(1-methylethyl)-5-[1-methyl-3-(trifluoromethyl)-1H-pyrazol-5-yl][1,2,4]triazolo[1,5-a]pyrimidin-7(4H)-one | Calc'd 327, found 327 | B | 1217 |
| 11-88 | 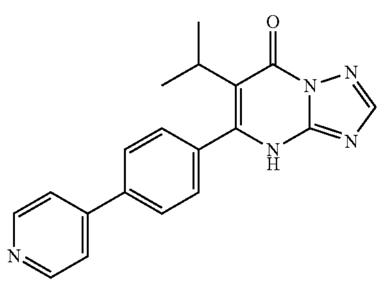 [SMILES: CC(C)c1c(-c2ccc(-c3ccncc3)cc2)[nH]c2ncnn2c1=O] | 6-(1-methylethyl)-5-(4-pyridin-4-ylphenyl)[1,2,4]triazolo[1,5-a]pyrimidin-7(4H)-one | Calc'd 332, found 332 | B | 8.575 |
| 11-89 | 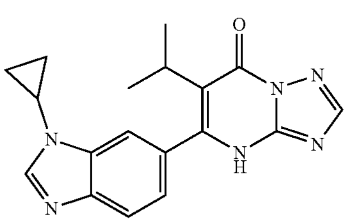 [SMILES: CC(C)c1c(-c2ccc3ncn(C4CC4)c3c2)[nH]c2ncnn2c1=O] | 5-(1-cyclopropyl-1H-benzimidazol-6-yl)-6-(1-methylethyl)[1,2,4]triazolo[1,5-a]pyrimidin-7(4H)-one | Calc'd 335, found 335 | B | 21.33 |

TABLE 2-continued

| Ex. No. | Structure | Name | Exact Mass [M + H]+ | Method | IC50 (nM) |
|---|---|---|---|---|---|
| 11-90 | 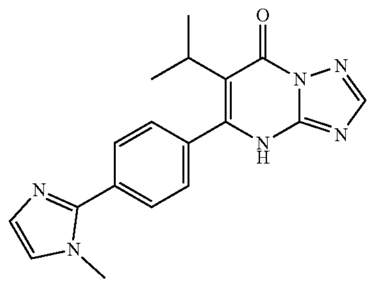 [SMILES: CC(C)c1c(-c2ccc(-c3nccn3C)cc2)[nH]c2ncnn2c1=O] | 6-(1-methylethyl)-5-[4-(1-methyl-1H-imidazol-2-yl)phenyl][1,2,4]triazolo[1,5-a]pyrimidin-7(4H)-one | Calc'd 335, found 335 | B | 7.256 |
| 11-91 | 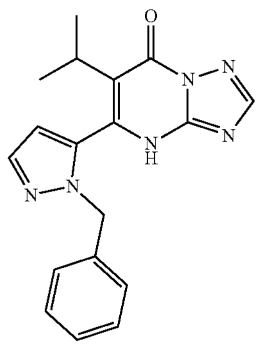 [SMILES: CC(C)c1c(-c2ccnn2Cc2ccccc2)[nH]c2ncnn2c1=O] | 5-(1-benzyl-1H-pyrazol-5-yl)-6-(1-methylethyl)[1,2,4]triazolo[1,5-a]pyrimidin-7(4H)-one | Calc'd 335, found 335 | B | 633.8 |
| 11-92 | 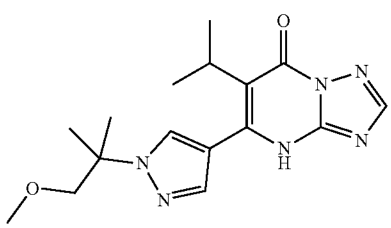 [SMILES: COCC(C)(C)n1cc(-c2[nH]c3ncnn3c(=O)c2C(C)C)cn1] | 5-[1-(2-methoxy-1,1-dimethylethyl)-1H-pyrazol-4-yl]-6-(1-methylethyl)[1,2,4]triazolo[1,5-a]pyrimidin-7(4H)-one | Calc'd 331, found 331 | A | 5.287 |
| 11-93 | 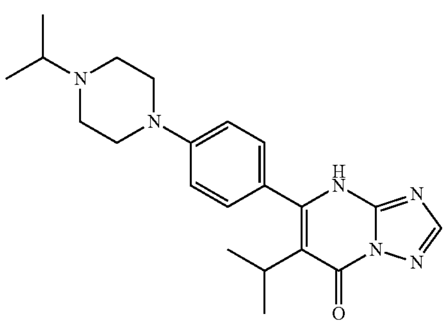 [SMILES: CC(C)c1c(-c2ccc(N3CCN(C(C)C)CC3)cc2)[nH]c2ncnn2c1=O] | 6-(1-methylethyl)-5-{4-[4-(1-methylethyl)piperazin-1-yl]phenyl}[1,2,4]triazolo[1,5-a]pyrimidin-7(4H)-one | Calc'd 381, found 381 | B | 15.5 |
| 11-94 | 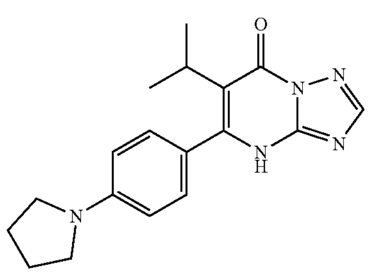 [SMILES: CC(C)c1c(-c2ccc(N3CCCC3)cc2)[nH]c2ncnn2c1=O] | 6-(1-methylethyl)-5-(4-pyrrolidin-1-ylphenyl)[1,2,4]triazolo[1,5-a]pyrimidin-7(4H)-one | Calc'd 324, found 324 | B | 20.15 |

TABLE 2-continued

| Ex. No. | Structure | Name | Exact Mass [M + H]+ | Method | IC50 (nM) |
|---|---|---|---|---|---|
| 11-95 | 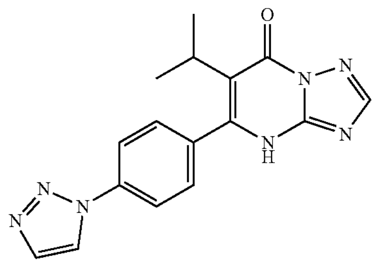 [SMILES: CC(C)c1c(-c2ccc(-n3ccnn3)cc2)[nH]c2ncnn2c1=O] | 6-(1-methylethyl)-5-[4-(1H-1,2,3-triazol-1-yl)phenyl][1,2,4]triazolo[1,5-a]pyrimidin-7(4H)-one | Calc'd 322, found 322 | B | 8.592 |
| 11-96 | 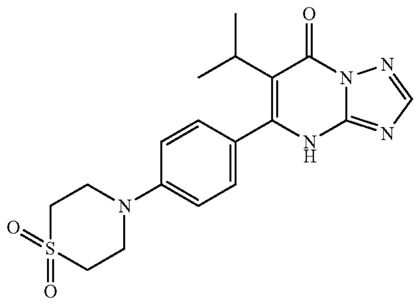 [SMILES: CC(C)c1c(-c2ccc(N3CCS(=O)(=O)CC3)cc2)[nH]c2ncnn2c1=O] | 5-[4-(1,1-dioxidothiomorpholin-4-yl)phenyl]-6-(1-methylethyl)[1,2,4]triazolo[1,5-a]pyrimidin-7(4H)-one | Calc'd 388, found 388 | B | 13.5 |
| 11-97 | 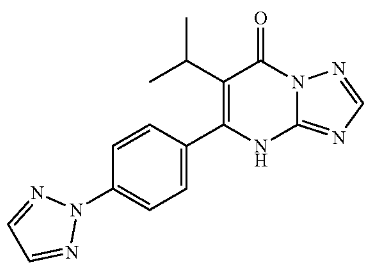 [SMILES: CC(C)c1c(-c2ccc(-n3nccn3)cc2)[nH]c2ncnn2c1=O] | 6-(1-methylethyl)-5-[4-(2H-1,2,3-triazol-2-yl)phenyl][1,2,4]triazolo[1,5-a]pyrimidin-7(4H)-one | Calc'd 322, found 322 | B | 32.35 |
| 11-98 | 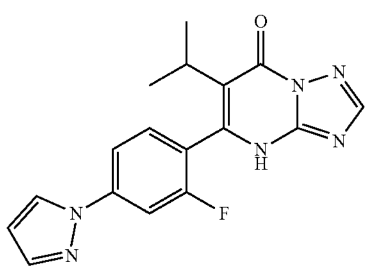 [SMILES: CC(C)c1c(-c2ccc(-n3cccn3)cc2F)[nH]c2ncnn2c1=O] | 5-[2-fluoro-4-(1H-pyrazol-1-yl)phenyl]-6-(1-methylethyl)[1,2,4]triazolo[1,5-a]pyrimidin-7(4H)-one | Calc'd 339, found 339 | B | 121.8 |
| 11-99 | 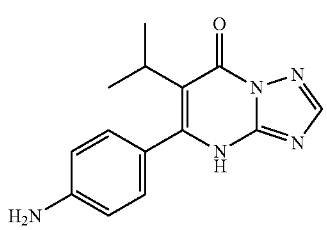 [SMILES: CC(C)c1c(-c2ccc(N)cc2)[nH]c2ncnn2c1=O] | 5-(4-aminophenyl)-6-(1-methylethyl)[1,2,4]triazolo[1,5-a]pyrimidin-7(4H)-one | Calc'd 270, found 270 | B | 32.86 |
| 11-100 | 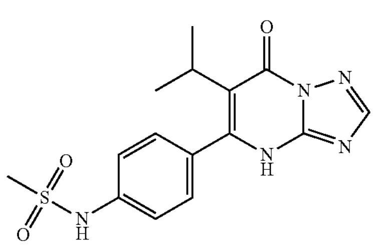 [SMILES: CC(C)c1c(-c2ccc(NS(C)(=O)=O)cc2)[nH]c2ncnn2c1=O] | N-{4-[6-(1-methylethyl)-7-oxo-4,7-dihydro[1,2,4]triazolo[1,5-a]pyrimidin-5-yl]phenyl}methanesulfonamide | Calc'd 348, found 348 | B | 20.06 |

TABLE 2-continued

| Ex. No. | Structure | Name | Exact Mass [M + H]+ | Method | IC50 (nM) |
|---|---|---|---|---|---|
| 11-101 | 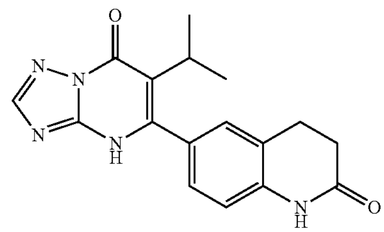 [SMILES: CC(C)c1c(-c2ccc3c(c2)CCC(=O)N3)[nH]c2ncnn2c1=O] | 6-[6-(1-methylethyl)-7-oxo-4,7-dihydro[1,2,4]triazolo[1,5-a]pyrimidin-5-yl]-3,4-dihydroquinolin-2(1H)-one | Calc'd 324, found 324 | B | 7.568 |
| 11-102 | 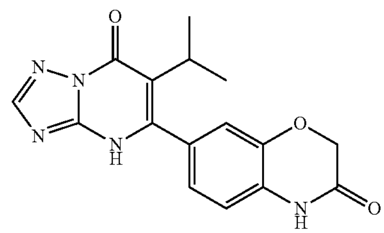 [SMILES: CC(C)c1c(-c2ccc3c(c2)OCC(=O)N3)[nH]c2ncnn2c1=O] | 7-[6-(1-methylethyl)-7-oxo-4,7-dihydro[1,2,4]triazolo[1,5-a]pyrimidin-5-yl]-2H-1,4-benzoxazin-3(4H)-one | Calc'd 326, found 326 | B | 17.82 |
| 11-103 | 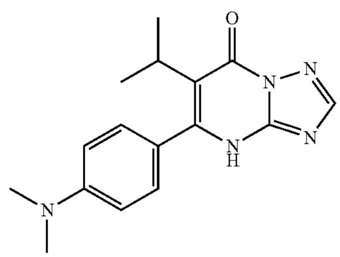 [SMILES: CC(C)c1c(-c2ccc(N(C)C)cc2)[nH]c2ncnn2c1=O] | 5-[4-(dimethylamino)phenyl]-6-(1-methylethyl)[1,2,4]triazolo[1,5-a]pyrimidin-7(4H)-one | Calc'd 298, found 298 | B | 36.94 |
| 11-104 | 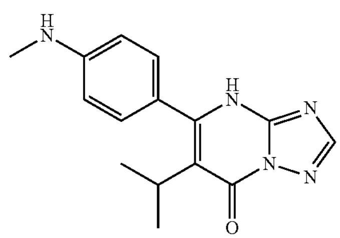 [SMILES: CNc1ccc(-c2[nH]c3ncnn3c(=O)c2C(C)C)cc1] | 5-[4-(methylamino)phenyl]-6-(1-methylethyl)[1,2,4]triazolo[1,5-a]pyrimidin-7(4H)-one | Calc'd 284, found 284 | B | 43.82 |
| 11-105 | 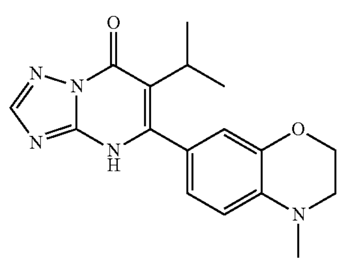 [SMILES: CC(C)c1c(-c2ccc3c(c2)OCCN3C)[nH]c2ncnn2c1=O] | 5-(4-methyl-3,4-dihydro-2H-1,4-benzoxazin-7-yl)-6-(1-methylethyl)[1,2,4]triazolo[1,5-a]pyrimidin-7(4H)-one | Calc'd 326, found 326 | B | 34.19 |
| 11-106 | 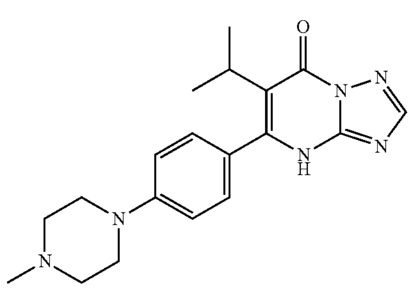 [SMILES: CC(C)c1c(-c2ccc(N3CCN(C)CC3)cc2)[nH]c2ncnn2c1=O] | 6-(1-methylethyl)-5-[4-(4-methylpiperazin-1-yl)phenyl][1,2,4]triazolo[1,5-a]pyrimidin-7(4H)-one | Calc'd 353, found 353 | B | 16.59 |

TABLE 2-continued

| Ex. No. | Structure | Name | Exact Mass [M + H]+ | Method | IC50 (nM) |
|---|---|---|---|---|---|
| 11-107 | 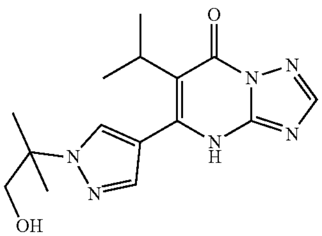 [SMILES: CC(C)c1c(-c2cnn(C(C)(C)CO)c2)[nH]c2ncnn2c1=O] | 5-[1-(2-hydroxy-1,1-dimethylethyl)-1H-pyrazol-4-yl]-6-(1-methylethyl)[1,2,4]triazolo[1,5-a]pyrimidin-7(4H)-one | Calc'd 317, found 317 | A | 5.081 |
| 11-108 | 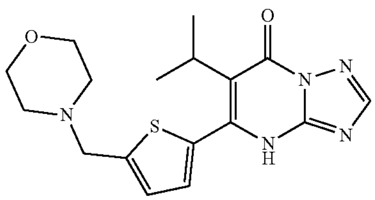 [SMILES: CC(C)c1c(-c2ccc(CN3CCOCC3)s2)[nH]c2ncnn2c1=O] | 6-(1-methylethyl)-5-[5-(morpholin-4-ylmethyl)thiophen-2-yl][1,2,4]triazolo[1,5-a]pyrimidin-7(4H)-one | Calc'd 360, found 360 | B | 5.081 |
| 11-109 | 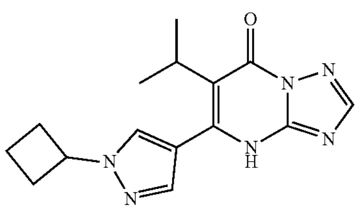 [SMILES: CC(C)c1c(-c2cnn(C3CCC3)c2)[nH]c2ncnn2c1=O] | 5-(1-cyclobutyl-1H-pyrazol-4-yl)-6-(1-methylethyl)[1,2,4]triazolo[1,5-a]pyrimidin-7(4H)-one | Calc'd 299, found 299 | B | 5.081 |
| 11-110 | 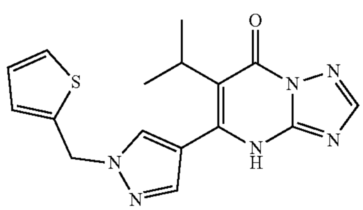 [SMILES: CC(C)c1c(-c2cnn(Cc3cccs3)c2)[nH]c2ncnn2c1=O] | 6-(1-methylethyl)-5-[1-(thiophen-2-ylmethyl)-1H-pyrazol-4-yl][1,2,4]triazolo[1,5-a]pyrimidin-7(4H)-one | Calc'd 341, found 341 | B | 6.7 |
| 11-111 | 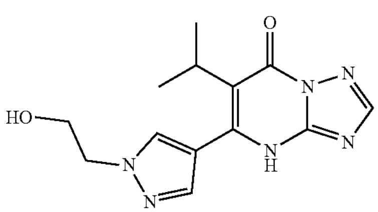 [SMILES: CC(C)c1c(-c2cnn(CCO)c2)[nH]c2ncnn2c1=O] | 5-[1-(2-hydroxyethyl)-1H-pyrazol-4-yl]-6-(1-methylethyl)[1,2,4]triazolo[1,5-a]pyrimidin-7(4H)-one | Calc'd 289, found 289 | B | 11.69 |
| 11-112 | 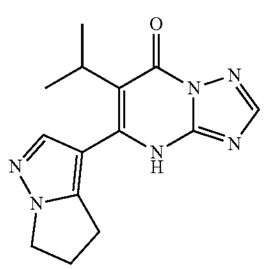 [SMILES: CC(C)c1c(-c2cnn3c2CCC3)[nH]c2ncnn2c1=O] | 5-(5,6-dihydro-4H-pyrrolo[1,2-b]pyrazol-3-yl)-6-(1-methylethyl)[1,2,4]triazolo[1,5-a]pyrimidin-7(4H)-one | Calc'd 285, found 285 | B | 51.24 |

TABLE 2-continued

| Ex. No. | Structure | Name | Exact Mass [M + H]+ | Method | IC50 (nM) |
|---|---|---|---|---|---|
| 11-113 | 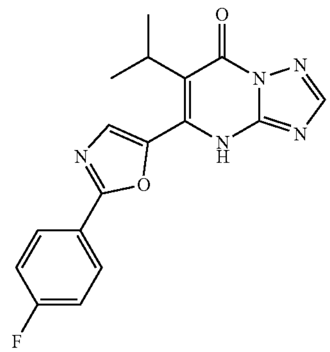 [SMILES: CC(C)c1c(-c2cnc(-c3ccc(F)cc3)o2)[nH]c2ncnn2c1=O] | 5-[2-(4-fluorophenyl)-1,3-oxazol-5-yl]-6-(1-methylethyl)[1,2,4]triazolo[1,5-a]pyrimidin-7(4H)-one | Calc'd 340, found 340 | B | 17.31 |
| 11-114 | 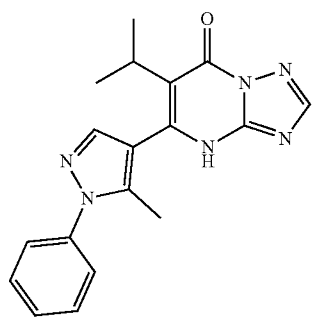 [SMILES: Cc1c(-c2[nH]c3ncnn3c(=O)c2C(C)C)cnn1-c1ccccc1] | 6-(1-methylethyl)-5-(5-methyl-1-phenyl-1H-pyrazol-4-yl)[1,2,4]triazolo[1,5-a]pyrimidin-7(4H)-one | Calc'd 335, found 335 | B | 336.7 |
| 11-115 | 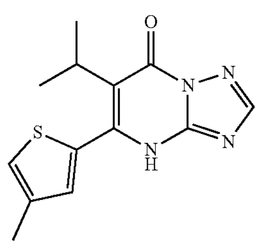 [SMILES: Cc1csc(-c2[nH]c3ncnn3c(=O)c2C(C)C)c1] | 6-(1-methylethyl)-5-(4-methylthiophen-2-yl)[1,2,4]triazolo[1,5-a]pyrimidin-7(4H)-one | Calc'd 275, found 275 | B | 121.8 |
| 11-116 | 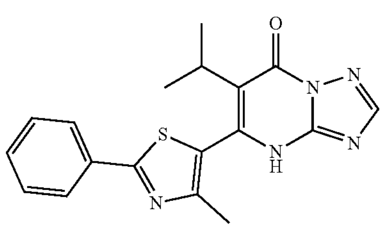 [SMILES: Cc1nc(-c2ccccc2)sc1-c1[nH]c2ncnn2c(=O)c1C(C)C] | 6-(1-methylethyl)-5-(4-methyl-2-phenyl-1,3-thiazol-5-yl)[1,2,4]triazolo[1,5-a]pyrimidin-7(4H)-one | Calc'd 352, found 352 | B | 443.6 |
| 11-117 | 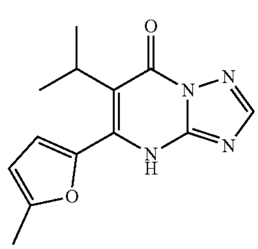 [SMILES: Cc1ccc(-c2[nH]c3ncnn3c(=O)c2C(C)C)o1] | 6-(1-methylethyl)-5-(5-methylfuran-2-yl)[1,2,4]triazolo[1,5-a]pyrimidin-7(4H)-one | Calc'd 259, found 259 | B | 552.4 |

TABLE 2-continued

| Ex. No. | Structure | Name | Exact Mass [M + H]+ | Method | IC50 (nM) |
|---|---|---|---|---|---|
| 11-118 | 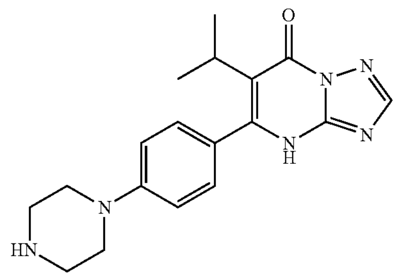 [SMILES: CC(C)c1c(-c2ccc(N3CCNCC3)cc2)[nH]c2ncnn2c1=O] | 6-(1-methylethyl)-5-(4-piperazin-1-ylphenyl)[1,2,4]triazolo[1,5-a]pyrimidin-7(4H)-one | Calc'd 339, found 339 | B | 9.787 |
| 11-119 | 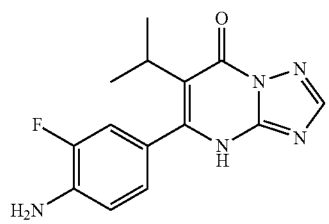 [SMILES: CC(C)c1c(-c2ccc(N)c(F)c2)[nH]c2ncnn2c1=O] | 5-(4-amino-3-fluorophenyl)-6-(1-methylethyl)[1,2,4]triazolo[1,5-a]pyrimidin-7(4H)-one | Calc'd 288, found 288 | B | 27.49 |
| 11-120 | 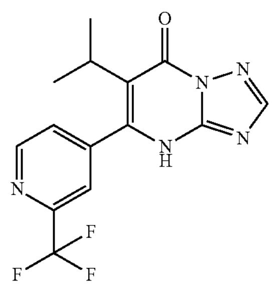 [SMILES: CC(C)c1c(-c2ccnc(C(F)(F)F)c2)[nH]c2ncnn2c1=O] | 6-(1-methylethyl)-5-[2-(trifluoromethyl)pyridin-4-yl][1,2,4]triazolo[1,5-a]pyrimidin-7(4H)-one | Calc'd 324.0, found | A | 16.98 |
| 11-121 | 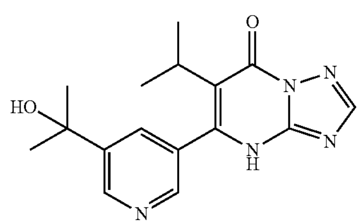 [SMILES: CC(C)c1c(-c2cncc(C(C)(C)O)c2)[nH]c2ncnn2c1=O] | 5-[5-(1-hydroxy-1-methylethyl)pyridin-3-yl]-6-(1-methylethyl)[1,2,4]triazolo[1,5-a]pyrimidin-7(4H)-one | Calc'd 314.0, found | A | 43.47 |
| 11-122 | 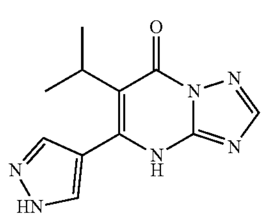 [SMILES: CC(C)c1c(-c2cn[nH]c2)[nH]c2ncnn2c1=O] | 6-(1-methylethyl)-5-(1H-pyrazol-4-yl)[1,2,4]triazolo[1,5-a]pyrimidin-7(4H)-one | Calc'd 245, found 245 | B | 13.29 |
| 11-123 | 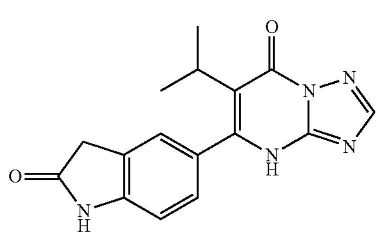 [SMILES: CC(C)c1c(-c2ccc3c(c2)CC(=O)N3)[nH]c2ncnn2c1=O] | 6-(1-methylethyl)-5-(2-oxo-2,3-dihydro-1H-indol-5-yl)[1,2,4]triazolo[1,5-a]pyrimidin-7(4H)-one | Calc'd 310, found 310 | B | 6.931 |

TABLE 2-continued

| Ex. No. | Structure | Name | Exact Mass [M + H]+ | Method | IC50 (nM) |
|---|---|---|---|---|---|
| 11-124 | 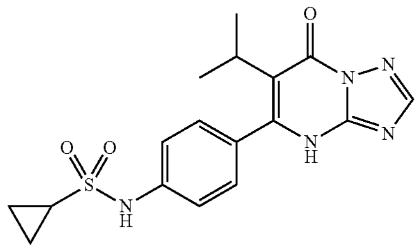 [SMILES: CC(C)c1c(-c2ccc(NS(=O)(=O)C3CC3)cc2)[nH]c2ncnn2c1=O] | N-{4-[6-(1-methylethyl)-7-oxo-4,7-dihydro[1,2,4]triazolo[1,5-a]pyrimidin-5-yl]phenyl}cyclopropanesulfonamide | Calc'd 374, found 374 | B | 8.762 |
| 11-125 | 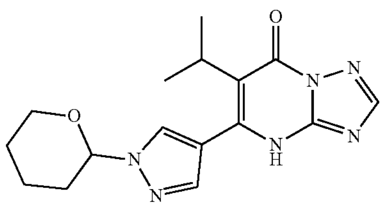 [SMILES: CC(C)c1c(-c2cnn(C3CCCCO3)c2)[nH]c2ncnn2c1=O] | 6-(1-methylethyl)-5-[1-(tetrahydro-2H-pyran-2-yl)-1H-pyrazol-4-yl][1,2,4]triazolo[1,5-a]pyrimidin-7(4H)-one | Calc'd 329, found 329 | B | 7.359 |
| 11-126 | 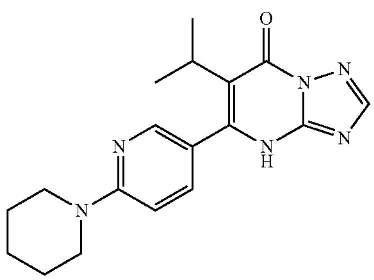 [SMILES: CC(C)c1c(-c2ccc(N3CCCCC3)nc2)[nH]c2ncnn2c1=O] | 6-(1-methylethyl)-5-(6-piperidin-1-ylpyridin-3-yl)[1,2,4]triazolo[1,5-a]pyrimidin-7(4H)-one | Calc'd 339, found 339 | B | 10.38 |
| 11-127 | 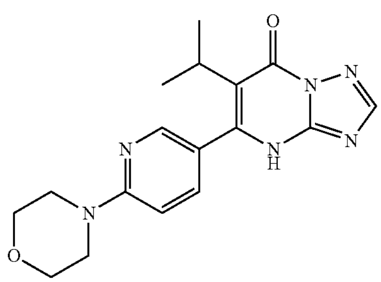 [SMILES: CC(C)c1c(-c2ccc(N3CCOCC3)nc2)[nH]c2ncnn2c1=O] | 6-(1-methylethyl)-5-(6-morpholin-4-ylpyridin-3-yl)[1,2,4]triazolo[1,5-a]pyrimidin-7(4H)-one | Calc'd 341, found 341 | B | 11.6 |
| 11-128 | 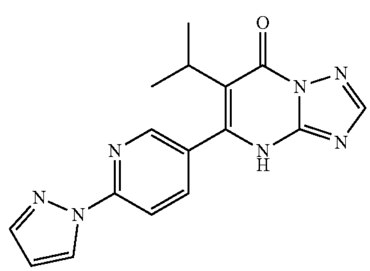 [SMILES: CC(C)c1c(-c2ccc(-n3cccn3)nc2)[nH]c2ncnn2c1=O] | 6-(1-methylethyl)-5-[6-(1H-pyrazol-1-yl)pyridin-3-yl][1,2,4]triazolo[1,5-a]pyrimidin-7(4H)-one | Calc'd 322, found 322 | B | 12.3 |
| 11-129 | 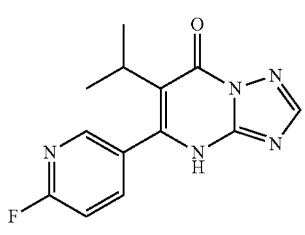 [SMILES: CC(C)c1c(-c2ccc(F)nc2)[nH]c2ncnn2c1=O] | 5-(6-fluoropyridin-3-yl)-6-(1-methylethyl)[1,2,4]triazolo[1,5-a]pyrimidin-7(4H)-one | Calc'd 274, found 274 | B | 66.84 |

TABLE 2-continued

| Ex. No. | Structure | Name | Exact Mass [M + H]+ | Method | IC50 (nM) |
|---|---|---|---|---|---|
| 11-130 | 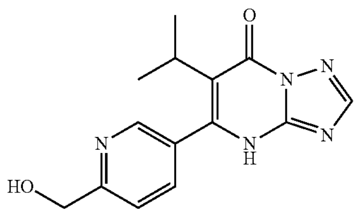 [SMILES: CC(C)c1c(-c2ccc(CO)nc2)[nH]c2ncnn2c1=O] | 5-[6-(hydroxymethyl)pyridin-3-yl]-6-(1-methylethyl)[1,2,4]triazolo[1,5-a]pyrimidin-7(4H)-one | Calc'd 286, found 286 | B | 54.46 |
| 11-131 | 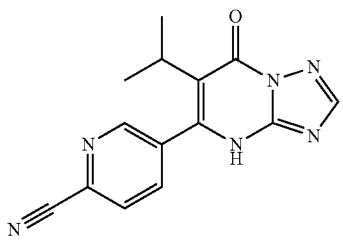 [SMILES: CC(C)c1c(-c2ccc(C#N)nc2)[nH]c2ncnn2c1=O] | 5-[6-(1-methylethyl)-7-oxo-4,7-dihydro[1,2,4]triazolo[1,5-a]pyrimidin-5-yl]pyridine-2-carbonitrile | Calc'd 281, found 281 | B | 48.73 |
| 11-132 | 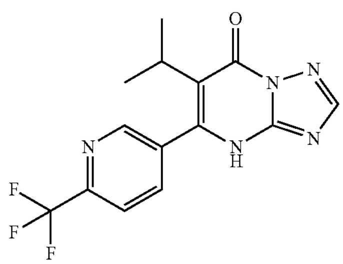 [SMILES: CC(C)c1c(-c2ccc(C(F)(F)F)nc2)[nH]c2ncnn2c1=O] | 6-(1-methylethyl)-5-[6-(trifluoromethyl)pyridin-3-yl][1,2,4]triazolo[1,5-a]pyrimidin-7(4H)-one | Calc'd 324, found 324 | B | 41.68 |
| 11-133 | 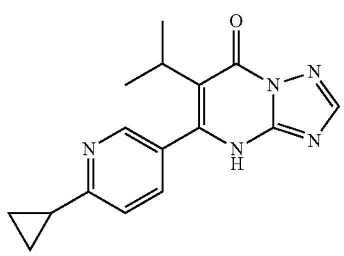 [SMILES: CC(C)c1c(-c2ccc(C3CC3)nc2)[nH]c2ncnn2c1=O] | 5-(6-cyclopropylpyridin-3-yl)-6-(1-methylethyl)[1,2,4]triazolo[1,5-a]pyrimidin-7(4H)-one | Calc'd 296, found 296 | B | 44.4 |
| 11-134 | 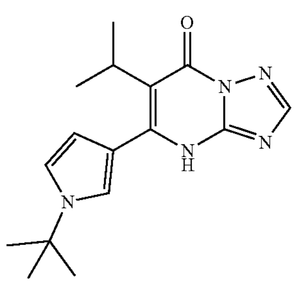 [SMILES: CC(C)c1c(-c2ccn(C(C)(C)C)c2)[nH]c2ncnn2c1=O] | 5-(1-tert-butyl-1H-pyrrol-3-yl)-6-(1-methylethyl)[1,2,4]triazolo[1,5-a]pyrimidin-7(4H)-one | Calc'd 300, found 300 | A | 5.081 |
| 11-135 | 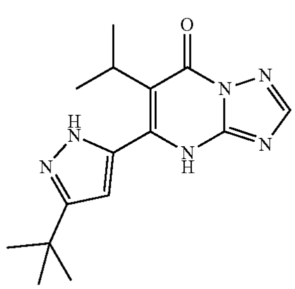 [SMILES: CC(C)c1c(-c2cc(C(C)(C)C)n[nH]2)[nH]c2ncnn2c1=O] | 5-(3-tert-butyl-1H-pyrazol-5-yl)-6-(1-methylethyl)[1,2,4]triazolo[1,5-a]pyrimidin-7(4H)-one | Calc'd 301, found 301 | A | 60.97 |

TABLE 2-continued

| Ex. No. | Structure | Name | Exact Mass [M + H]+ | Method | IC50 (nM) |
|---|---|---|---|---|---|
| 11-136 | 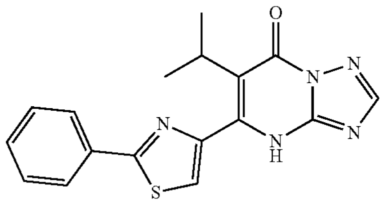 [SMILES: CC(C)c1c(-c2csc(-c3ccccc3)n2)[nH]c2ncnn2c1=O] | 6-(1-methylethyl)-5-(2-phenyl-1,3-thiazol-4-yl)[1,2,4]triazolo[1,5-a]pyrimidin-7(4H)-one | Calc'd 338, found 338 | B | 468.8 |
| 11-137 | 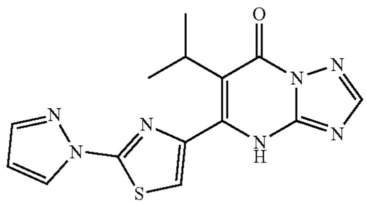 [SMILES: CC(C)c1c(-c2csc(-n3cccn3)n2)[nH]c2ncnn2c1=O] | 6-(1-methylethyl)-5-[2-(1H-pyrazol-1-yl)-1,3-thiazol-4-yl][1,2,4]triazolo[1,5-a]pyrimidin-7(4H)-one | Calc'd 328, found 328 | B | 41.94 |
| 11-138 | 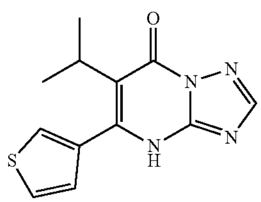 [SMILES: CC(C)c1c(-c2ccsc2)[nH]c2ncnn2c1=O] | 6-(1-methylethyl)-5-thiophen-3-yl[1,2,4]triazolo[1,5-a]pyrimidin-7(4H)-one | Calc'd 261, found 261 | A | 657.1 |
| 11-139 | 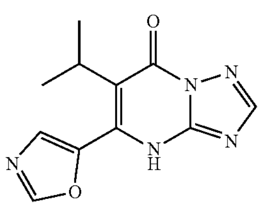 [SMILES: CC(C)c1c(-c2cnco2)[nH]c2ncnn2c1=O] | 6-(1-methylethyl)-5-(1,3-oxazol-5-yl)[1,2,4]triazolo[1,5-a]pyrimidin-7(4H)-one | Calc'd 246, found 246 | A | 193.1 |
| 11-140 | 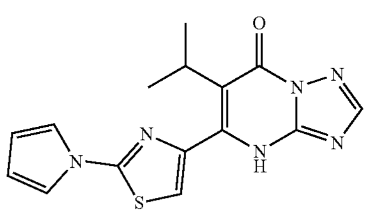 [SMILES: CC(C)c1c(-c2csc(-n3cccc3)n2)[nH]c2ncnn2c1=O] | 6-(1-methylethyl)-5-[2-(1H-pyrrol-1-yl)-1,3-thiazol-4-yl][1,2,4]triazolo[1,5-a]pyrimidin-7(4H)-one | Calc'd 327, found 327 | C | 124.2 |
| 11-141 | 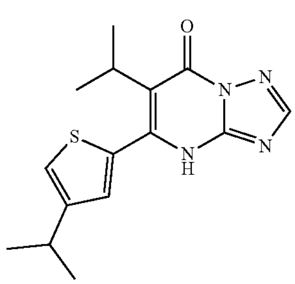 [SMILES: CC(C)c1csc(-c2[nH]c3ncnn3c(=O)c2C(C)C)c1] | 6-(1-methylethyl)-5-[4-(1-methylethyl)thiophen-2-yl][1,2,4]triazolo[1,5-a]pyrimidin-7(4H)-one | Calc'd 303, found 303 | C | 59.75 |

TABLE 2-continued

| Ex. No. | Structure | Name | Exact Mass [M + H]+ | Method | IC50 (nM) |
|---|---|---|---|---|---|
| 11-142 | 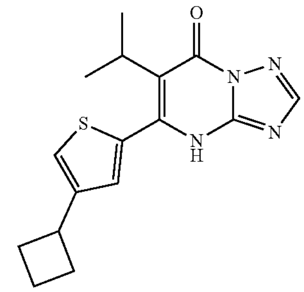 [SMILES: CC(C)c1c(-c2cc(C3CCC3)cs2)[nH]c2ncnn2c1=O] | 5-(4-cyclobutylthiophen-2-yl)-6-(1-methylethyl)[1,2,4]triazolo[1,5-a]pyrimidin-7(4H)-one | Calc'd 315, found 315 | C | 112 |
| 11-143 | 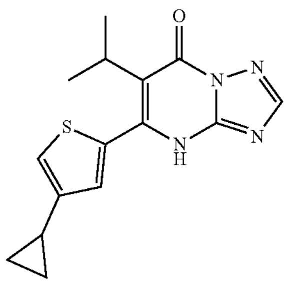 [SMILES: CC(C)c1c(-c2cc(C3CC3)cs2)[nH]c2ncnn2c1=O] | 5-(4-cyclopropylthiophen-2-yl)-6-(1-methylethyl)[1,2,4]triazolo[1,5-a]pyrimidin-7(4H)-one | Calc'd 301, found 301 | C | 79.33 |
| 11-144 | 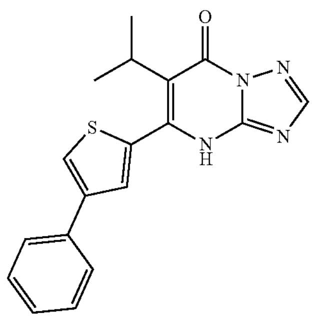 [SMILES: CC(C)c1c(-c2cc(-c3ccccc3)cs2)[nH]c2ncnn2c1=O] | 6-(1-methylethyl)-5-(4-phenylthiophen-2-yl)[1,2,4]triazolo[1,5-a]pyrimidin-7(4H)-one | Calc'd 337, found 337 | C | 76.19 |

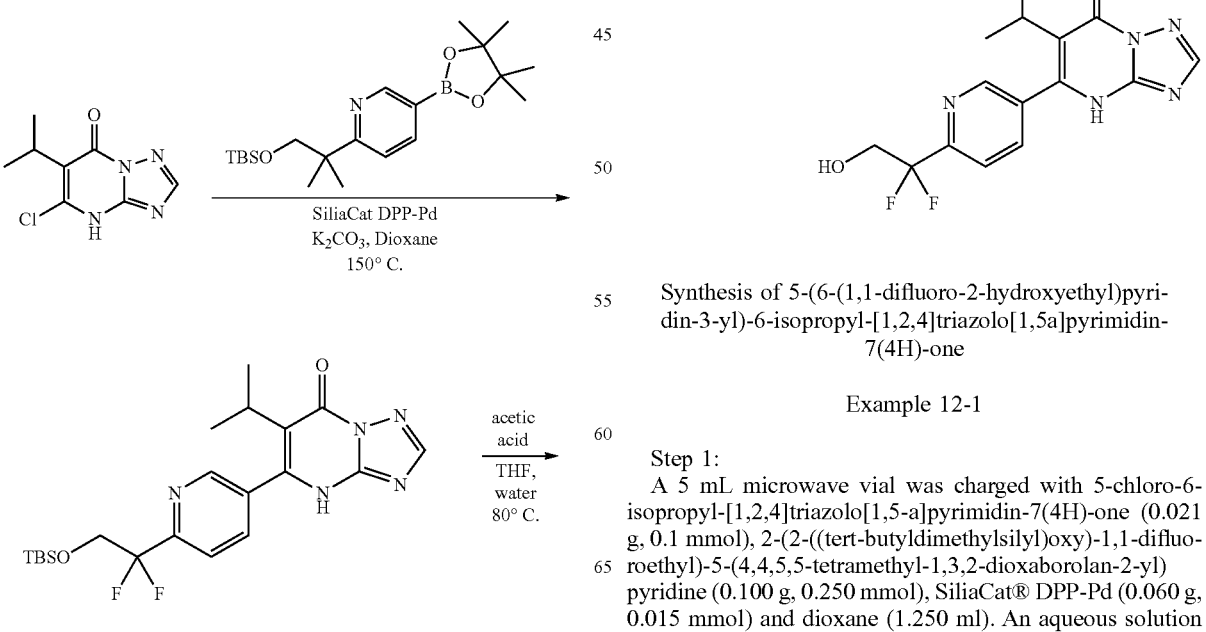

Synthesis of 5-(6-(1,1-difluoro-2-hydroxyethyl)pyridin-3-yl)-6-isopropyl-[1,2,4]triazolo[1,5a]pyrimidin-7(4H)-one Example 12-1

Step 1:

A 5 mL microwave vial was charged with 5-chloro-6-isopropyl-[1,2,4]triazolo[1,5-a]pyrimidin-7(4H)-one (0.021 g, 0.1 mmol), 2-(2-((tert-butyldimethylsilyl)oxy)-1,1-difluoroethyl)-5-(4,4,5,5-tetramethyl-1,3,2-dioxaborolan-2-yl)pyridine (0.100 g, 0.250 mmol), SiliaCat® DPP-Pd (0.060 g, 0.015 mmol) and dioxane (1.250 ml). An aqueous solution of potassium carbonate (0.150 ml, 0.300 mmol) was added, the vial capped and the contents irradiated in the microwave at 150° C. for 20 minutes. The reaction mixture was filtered, washed through with DCM (2 mL), and concentrated. The crude was taken forward without further purification. MS ESI calcd. for $C_{21}H_{29}F_2N_5O_2Si$ [M+H]$^+$ 450, found 450.

Step 2:

A 20 mL reaction vial was charged with 5-(6-(2-((tert-butyldimethylsilyl)oxy)-1,1-difluoroethyl)pyridin-3-yl)-6-isopropyl-[1,2,4]triazolo[1,5-a]pyrimidin-7(4H)-one (0.019 g, 0.033 mmol), THF (0.5 ml), water (0.5 ml) and acetic acid (1.5 mL, 26.2 mmol). The vial was capped and the contents heated at 80° C. for 16 hours. The reaction mixture was concentrated, taken up in DMSO, filtered and purified by mass triggered reverse phase HPLC (MeCN/water with 0.1% TFA modifier, linear gradient) to afford 5-(6-(1,1-difluoro-2-hydroxyethyl)pyridin-3-yl)-6-isopropyl-[1,2,4]triazolo[1,5-a]pyrimidin-7(4H)-one, TFA as a white solid. $^1$H NMR (600 MHz, DMSO-d$_6$): δ 8.79 (s, 1H); 8.27 (br s, 1H); 8.10 (d, J=8.0 Hz, 1H); 7.86 (d, J=8.0 Hz, 1H); 4.04 (t, J=13.8 Hz, 2H); 2.51-2.47 (m, 1H); 1.23 (d, J=6.9 Hz, 6H).

The following compounds (Table 3) were synthesized as described;

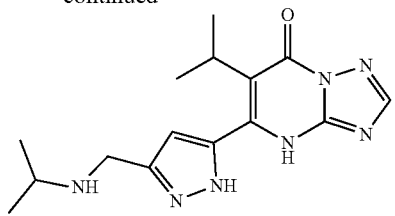

Synthesis of 6-isopropyl-5-(3-((isopropylamino)methyl)-1H-pyrazol-5-yl)-[1,2,4]triazolo[1,5-a]pyrimidin-7(4H)-one A mixture of tert-butyl isopropyl((5-(4,4,5,5-tetramethyl-1,3,2-dioxaborolan-2-yl)-1-((2-(trimethylsilyl)ethoxy)methyl)-1H-pyrazol-3-yl)methyl)carbamate (151 mg, 0.306 mmol), 5-chloro-6-isopropyl-[1,2,4]triazolo[1,5-a]pyrimidin-7(4H)-one (52 mg, 0.245 mmol), potassium carbonate (101 mg, 0.734 mmol) and 1,1'-bis(diphenylphosphino)ferrocene-palladium(II)dichloride dichloromethane complex (19.97 mg, 0.024 mmol) in a solution of dioxane (1.112 mL) and water (0.111 mL) was degassed (3×) under nitrogen and heated overnight at 110° C. The mixture was diluted with methanol, filtered and concentrated in vacuo. The residue

TABLE 3

| Ex. No. | Structure | Name | Exact Mass [M + H]+ | IC50 (nM) |
|---|---|---|---|---|
| 12-2 | (structure shown) | 5-[6-(1,1-difluoro-2-hydroxyethyl)pyridin-3-yl]-6-(1-methylethyl)[1,2,4]triazolo[1,5-a]pyrimidin-7(4H)-one | Cald'c 336, found 336 | 30.74 |
| 12-3 | (structure shown) | 5-[5-(hydroxymethyl)pyridin-3-yl]-6-(1-methylethyl)[1,2,4]triazolo[1,5-a]pyrimidin-7(4H)-one | Cald'c 286, found 286 | 22.51 |

Scheme 13

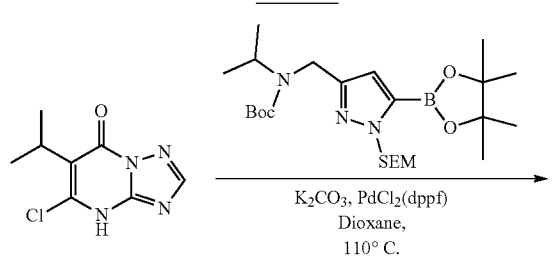

K$_2$CO$_3$, PdCl$_2$(dppf)
Dioxane,
110° C.

was purified by column chromatography on silica (0-10% methanol/DCM) to afford tert-butyl isopropyl((5-(6-isopropyl-7-oxo-4,7-dihydro-[1,2,4]triazolo[1,5-a]pyrimidin-5-yl)-1-((2-(trimethylsilyl)ethoxy)methyl)-1H-pyrazol-3-yl)methyl)carbamate which was taken up in a solution of hydrochloric acid (4 M, 4 mL, 16 mmol) and heated to 60° C. for 20 minutes. N,N'-Dimethylethylenediamine (0.105 mL, 0.978 mmol) was added and the reaction mixture stirred for an additional 30 minutes. The reaction mixture was concentrated in vacuo, taken up in DMSO, filtered and purified by mass triggered reverse phase HPLC (ACN/water with 0.1% TFA modifier, linear gradient) to afford 6-isopropyl-5-(3-((isopropylamino)methyl)-1H-pyrazol-5-yl)-[1,2, 4]triazolo[1,5-a]pyrimidin-7(4H)-one, TFA as a white solid. MS ESI calcd. for $C_{15}H_{21}N_7O$ [M+H]+ 316, found 316.

Scheme 14

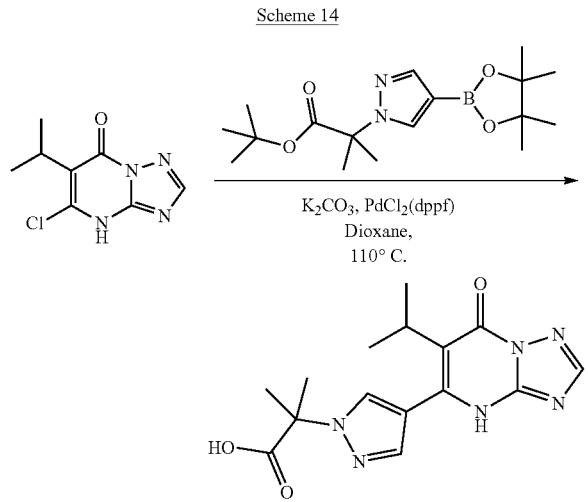

Synthesis of 2-(4-(6-isopropyl-7-oxo-4,7-dihydro-[1,2,4]triazolo[1,5-a]pyrimidin-5-yl)-1H-pyrazol-1-yl)-2-methylpropanoic Acid A 5 mL microwave vial was charged with 5-chloro-6-isopropyl-[1,2,4]triazolo[1,5-a]pyrimidin-7(4H)-one (21.26 mg, 0.1 mmol), tert-butyl 2-methyl-2-(4-(4,4,5,5-tetramethyl-1,3,2-dioxaborolan-2-yl)-1H-pyrazol-1-yl)propanoate (67.2 mg, 0.200 mmol), 1,1'-bis(diphenylphosphino)ferrocene-palladium(ii)dichloride dichloromethane complex (8.19 mg, 10.00 μmol) and dioxane (1.25 ml). An aqueous solution of potassium carbonate (0.150 mL, 0.300 mmol) was added, the vial capped, and the contents heated to 110° C. for 16 hours. The mixture was diluted with chloroform/isopropanol—3:1 (5 mL), washed with hydrochloric acid (1M, 5 mL), and the organic layer collected using a phase separator column (25 mL). The organics were concentrated, and the resulting residue taken up in trifluoroacetic acid (2 mL, 26.0 mmol) and stirred at room temperature for 10 minutes. The mixture was concentrated, taken up in DMSO, filtered and purified by mass triggered reverse phase HPLC (ACN/water with 0.1% TFA modifier, linear gradient) to afford 2-(4-(6-isopropyl-7-oxo-4,7-dihydro-[1,2,4]triazolo[1,5-a]pyrimidin-5-yl)-1H-pyrazol-1-yl)-2-methylpropanoic acid as a white solid. $^1$H NMR (600 MHz, DMSO-d$_6$): δ 13.10 (br s, 1H); 12.88 (br s, 1H); 8.23 (s, 1H); 8.15 (s, 1H); 7.72 (s, 1H); 3.04-2.98 (m, 1H); 1.76 (s, 6H); 1.28 (d, J=6.9 Hz, 6H).

Scheme 15

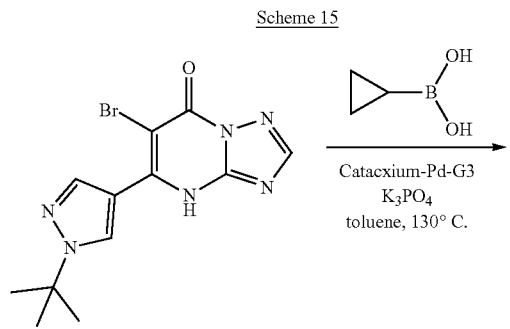

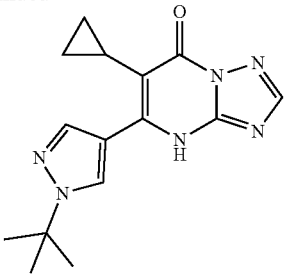

Synthesis of 5-(1-(tert-butyl)-1H-pyrazol-4-yl)-6-cyclopropyl-[1,2,4]triazolo[1,5-a]pyrimidin-7(4H)-one A 5 mL microwave vial was charged with 6-bromo-5-(1-(tert-butyl)-1H-pyrazol-4-yl)-[1,2,4]triazolo[1,5-a]pyrimidin-7(4H)-one (100 mg, 0.297 mmol), cyclopropylboronic acid (76 mg, 0.890 mmol), potassium phosphate tribasic (126 mg, 0.593 mmol), cataCXium-A-Pd-G3 (mesylate[(di (1-adamantyl)-n-butylphosphine)-2-(2'-amino-1,1'-biphenyl)]palladium(II), [(Di(1-adamantyl)-butylphosphine)-2-(2'-amino-1,1'-biphenyl)]palladium(II) methanesulfonate) (21.60 mg, 0.030 mmol) and toluene (4 mL). The vial was capped and de-gassed with argon for 5 minutes. The reaction mixture was then heated at 130° C. for 16 hours. The mixture was cooled, diluted with chloroform/isopropanol—3:1 (5 mL), washed with hydrochloric acid (1M, 5 mL), dried (MgSO$_4$), filtered and the solvent was evaporated under reduced pressure. The reaction mixture was concentrated, taken up in DMSO, filtered and purified by mass triggered reverse phase HPLC (MeCN/water with 0.1% TFA modifier, linear gradient) to afford 5-(1-(tert-butyl)-1H-pyrazol-4-yl)-6-cyclopropyl-[1,2,4]triazolo[1,5-a]pyrimidin-7(4H)-one as a white solid. $^1$H NMR (600 MHz, DMSO-d$_6$): δ 8.42 (s, 1H); 8.17 (s, 1H); 8.01 (s, 1H); 1.75-1.73 (m, 1H); 1.55 (s, 9H); 0.83 (d, J=7.8 Hz, 2H); 0.27 (d, J=5.5 Hz, 2H).

KDM5B TR-FRET Enzyme Activity Assay

KDM5B enzymatic activity was determined with the LANCE (Lanthanide Chelate Excite) TR-FRET (Time-resolved fluorescence resonance energy transfer) assay. In this assay, the potency (IC50) of each compound was determined from a ten point (1:3 serial dilution; final compound concentration range in assay from 100000 nM to 5.08 nM) titration curve using the following outlined procedure. To each well of a white Greiner 1536 Lumitrac 1536 well-plate, 50 nL of compound (100 fold dilution in final assay volume of 5 μL) was dispensed, followed by the addition of 4 μL of 1× assay buffer (50 mM Hepes 7.3, 0.5 mM TCEP, 0.005% Brij-35, 0.02% BSA, 50 μM Na-L-Ascorbate and 2 μM AmFe(II)Sulfate) containing 5 nM of Full-length KDM5B enzyme (recombinant protein from baculovirus-transfected Sf21 cells: full-length KDM5B; MW=176.825 kDa). Following a 30 minutes compound and enzyme incubation in a humidified chamber, each reaction was initiated by the addition of 1 μL 1× assay buffer containing 50 nM biotinylated H3K4Me3 peptide, and 500 nM α-ketoglutarate. The final reaction in each well of 5 μL consists of 5 nM KDM5B, 500 nM biotinylated-peptide, and 500 nM α-ketoglutarate. De-methylation reactions were allowed to proceed for 60 minutes. Reactions were immediately quenched by the addition of 5 uL of 2× Lance Detection Buffer (PerkinElmer) with 0.5 mM EDTA and 2 nM of Eu-anti- H3K4Me1-2 antibody, and 30 nM of Streptavidin-conjugated Dylight 650 detection reagents. After 60 minutes incubation with detection reagents, reaction plates were read on a PerkinElmer EnVision plate reader using standard TR-FRET protocol. Briefly, excitation of donor molecules (Eu-chelate-anti-H3K4Me1-2-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). IC50 values were determined by 4 parameter robust fit of TR-FRET ratio values vs. (Log 10) compound concentrations.

While the present invention has been described in conjunction with the specific examples set forth above, many alternatives, modifications and variations thereof will be apparent to those of ordinary skill in the art. All such alternatives, modifications and variations are intended to fall within the spirit and scope of the present invention.

What is claimed is:

1. A compound of formula I (Ia)  (Ib)   I or a pharmaceutically acceptable salt thereof, wherein
$R^1$ is
  $C_1$-$C_6$ alkyl, which is substituted with $CF_3$,
  —($C_2$-$C_3$ alkylene)-C(O)—O—$C_1$-$C_6$ alkyl,
  or
  a 6-membered unsaturated carbocycle;
$R^2$ is
  halogen,
  $CF_3$,
  —$C_2$-$C_4$ alkenylene-O—$C_1$-$C_3$ alkyl,
  C(O)—O—$C_1$-$C_6$ alkyl,
  C(=$CH_2$)$C_1$-$C_4$ alkyl,
  —($C_2$-$C_4$ alkenylene)—$C_6H_5$,
  —($C_1$-$C_4$ alkylene)—$C_6H_5$,
  a 3-, 4-, 5- or 6 membered saturated carbocycle,
  a 6-membered unsaturated carbocycle, unsubstituted or mono-substituted or independently di-substituted with $R^3$,
  a 6-membered saturated heterocycle, unsubstituted, having 1 heteroatom which is O,
  a 5-membered unsaturated heterocycle having 1 or 2 heteroatoms independently selected from N, O and S, unsubstituted or independently mono- or di-substituted with $R^5$, or
  a 6-membered unsaturated heterocycle, having 1 or 2 heteroatoms independently selected from N and O, unsubstituted or independently mono-, di-, tri- or tetra-substituted with $R^4$, or
  an 8-, 9-, or 10-membered unsaturated bicyclic heterocycle having 1, 2 or 3 heteroatoms independently selected from N or O, unsubstituted or substituted with $R^6$;

$R^3$ is
  —$C_1$-$C_3$ alkyl, unsubstituted or mono- or independently di-substituted with a 6-membered saturated heterocycle having 1 or 2 heteroatoms independently selected from N and O, —C(O)O$C_1$-$C_3$ alkyl, —OH, —$CF_3$, and CN,
  $C_1$-$C_3$ alkoxy,
  halogen,
  CN,
  OH,
  O—$C_6H_5$,
  O$C_1$-$C_3$ alkyl,
  C(O)O$C_1$-$C_3$ alkyl,
  $CF_3$,
  C(O)N($CH_3$)$_2$,
  $NH_2$,
  $NHSO_2C_1$-$C_3$ alkyl,
  NH($C_1$-$C_3$ alkyl),
  N($C_1$-$C_3$ alkyl)($C_1$-$C_3$ alkyl),
  $NHSO_2$ $cC_3H_5$,
  a 5- or 6-membered saturated heterocycle having 1 or 2 heteroatoms independently selected from N, O and S, wherein S is a dioxide, unsubstituted or substituted with $C_1$-$C_3$ alkyl, or
  a 5- or 6-membered unsaturated heterocycle, unsubstituted or substituted with $C_1$-$C_3$ alkyl, having 1, 2 or 3 N atoms;
$R^4$ is
  halogen,
  $C_1$-$C_3$ alkyl, unsubstituted or substituted with —OH,
  CN,
  $CF_3$,
  $cC_3H_5$,
  $CF_2CH_2OH$,
  a 6-membered saturated heterocycle having 1 or 2 heteroatoms independently selected from N and O, or
  a 5-membered unsaturated heterocycle having 2 N atoms;
$R^5$ is
  $CF_3$,
  $C_1$-$C_5$ alkyl, unsubstituted or substituted with a 6-membered saturated heterocycle having 1 or 2 heteroatoms independently selected from N and O, a 6-membered unsaturated carbocycle, a 6-membered unsaturated heterocycle having 1 N atom, —O$C_1$-$C_4$ alkyl, —OH, —C(O)OH, a 5-membered unsaturated heterocycle having 1 S atom, $cC_3H_5$, —$SO_2C_1$-$C_4$ alkyl, —NH$C_1$-$C_4$ alkyl, or a 3-5-membered saturated carbocycle unsubstituted or substituted with F,
  a 3-, 4-, 5- or 6-membered saturated carbocycle,
  a 6-membered unsaturated carbocycle unsubstituted or substituted with halogen,
  a 6-membered saturated heterocycle having 1 or 2 heteroatoms independently selected from N and O, or
  a 5-membered unsaturated unsubstituted heterocycle having 1 or 2 N heteroatoms; and
$R^6$ is $C_1$-$C_6$ alkyl, cyclopropyl or =O.

2. A compound of claim 1, or a pharmaceutically acceptable salt thereof, wherein
$R^1$ is
  —$CH_2C(O)OCH_3$, $CH_2CF_3$, , or .

3. A compound of claim 2, or a pharmaceutically acceptable salt thereof, wherein
R² is
Cl, C(=CH₂)CH₂CH₂CH₃,
CH=CHCH₂OCH₃,
CF₃, C(O)OCH₂CH₃, CH=CHC₆H₅,
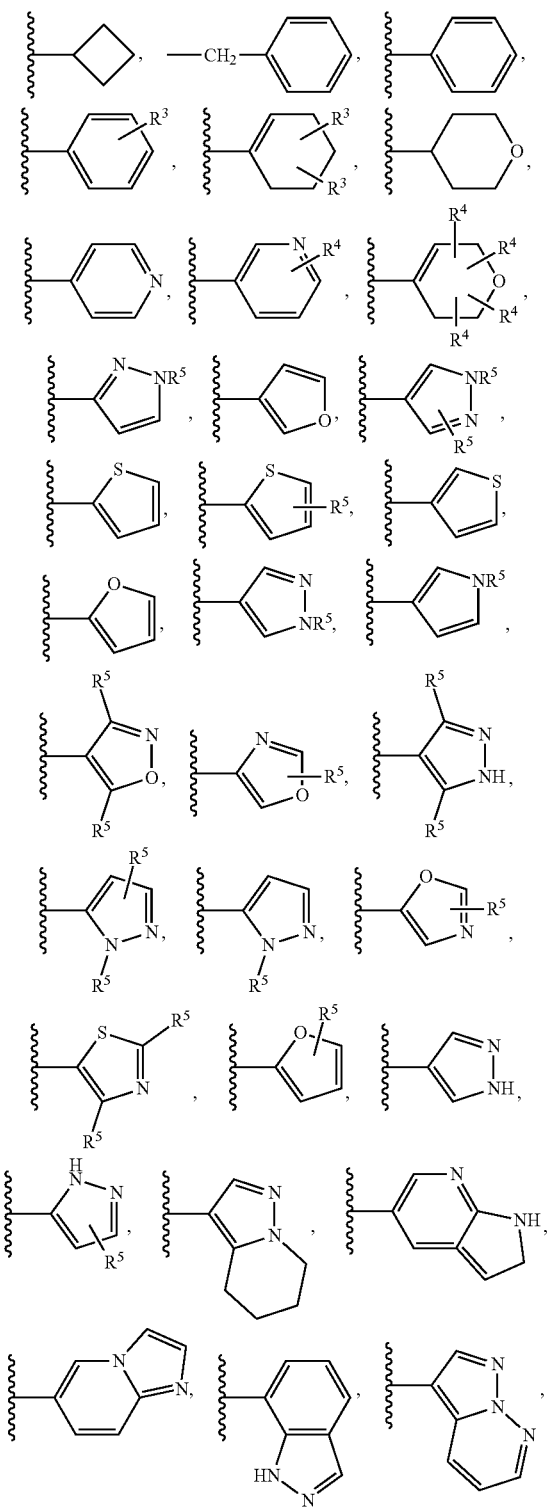
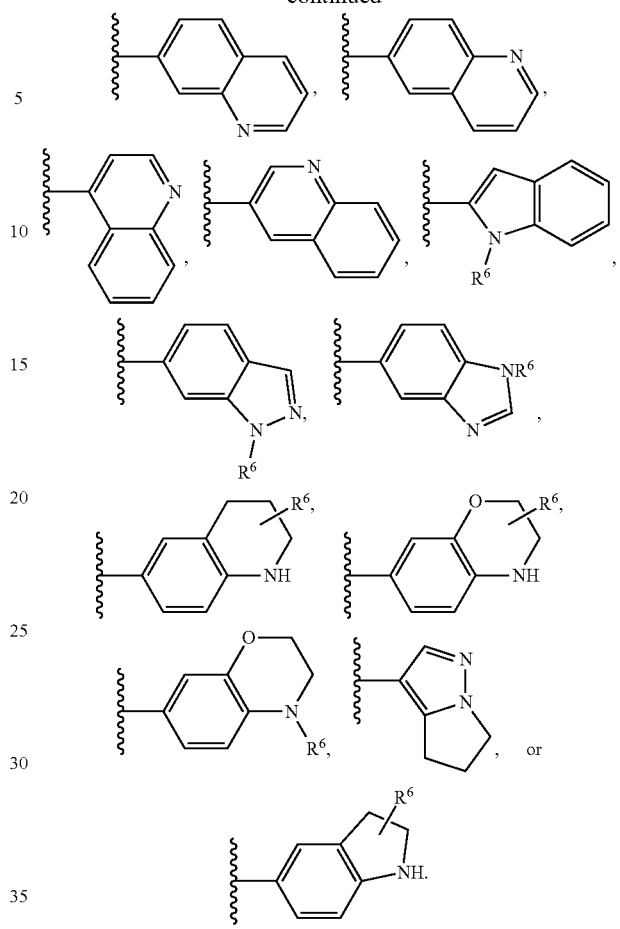
4. A compound of claim 1, or a pharmaceutically acceptable salt thereof, wherein
R² is Cl, C(=CH₂)CH₂CH₂CH₃,
CH=CHCH₂OCH₃,
CF₃, C(O)OCH₂CH₃, CH=CHC₆H₅,
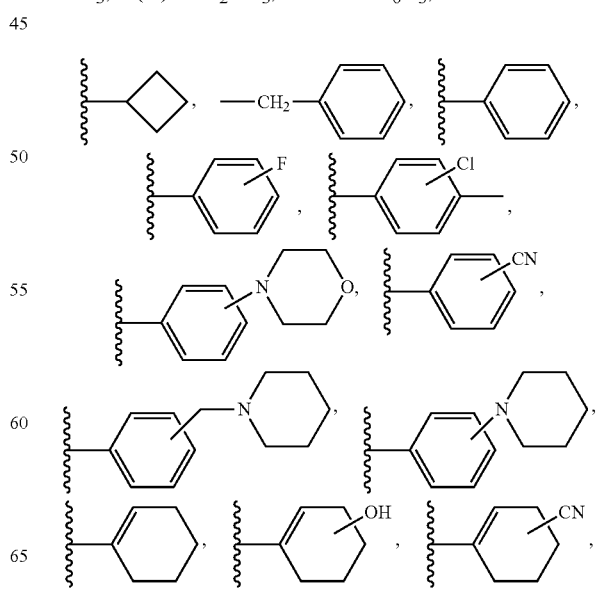

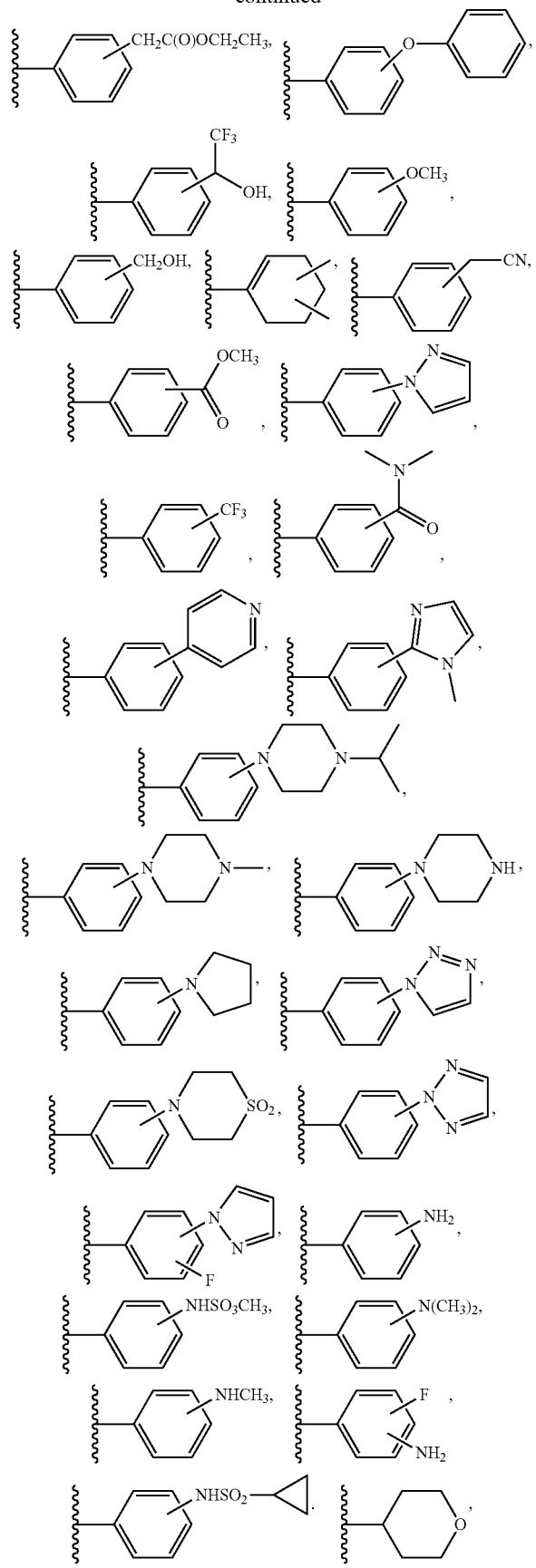
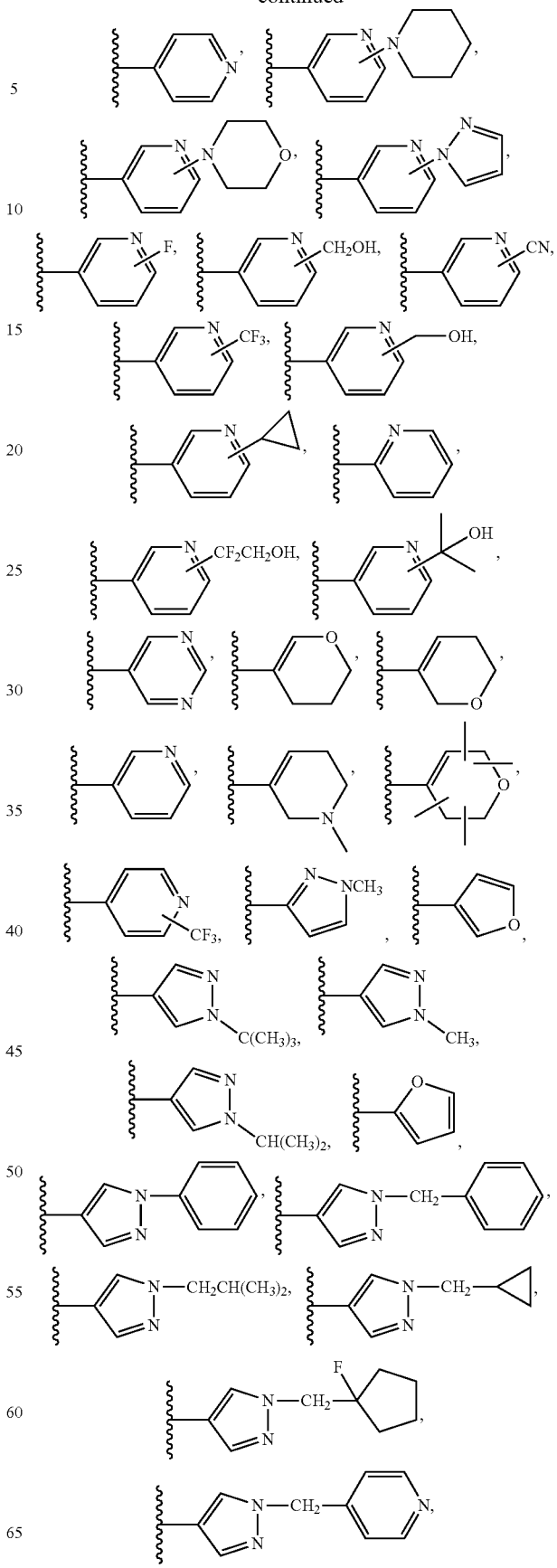

131
-continued
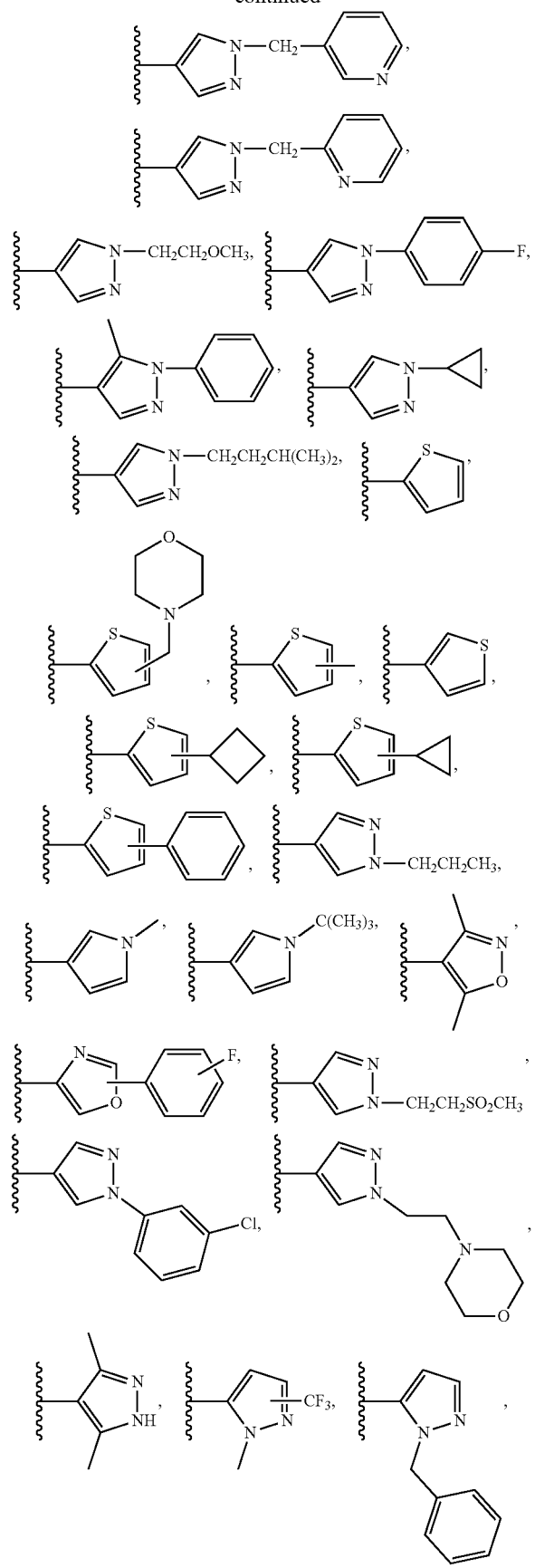
132
-continued
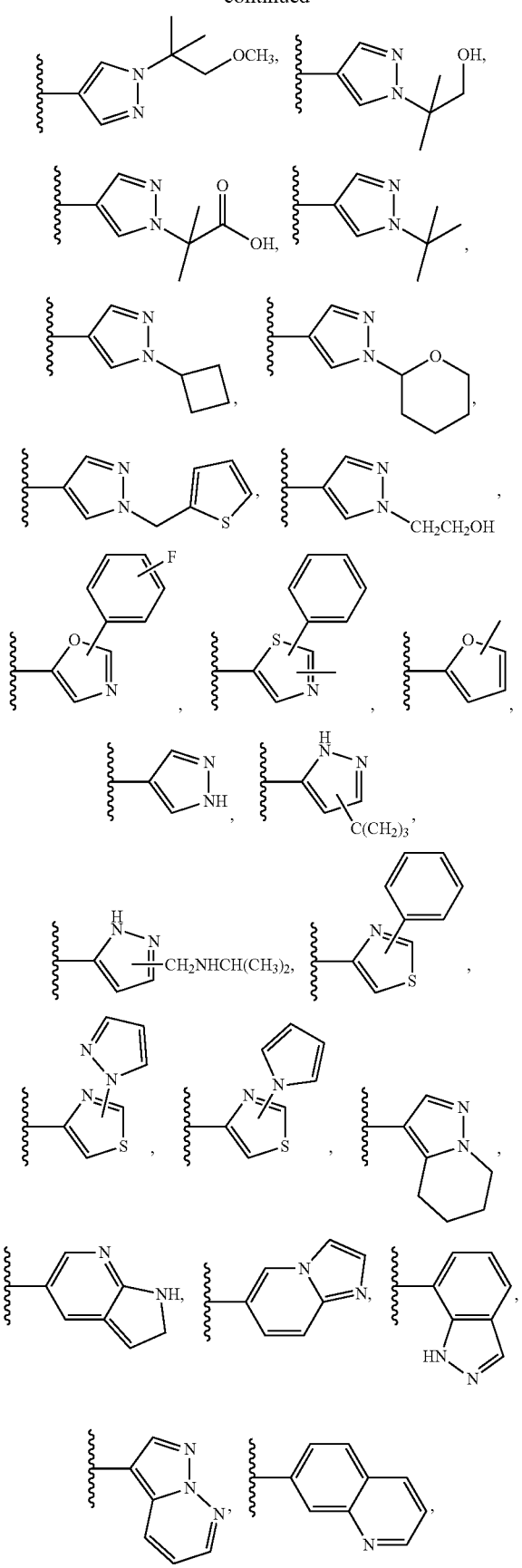

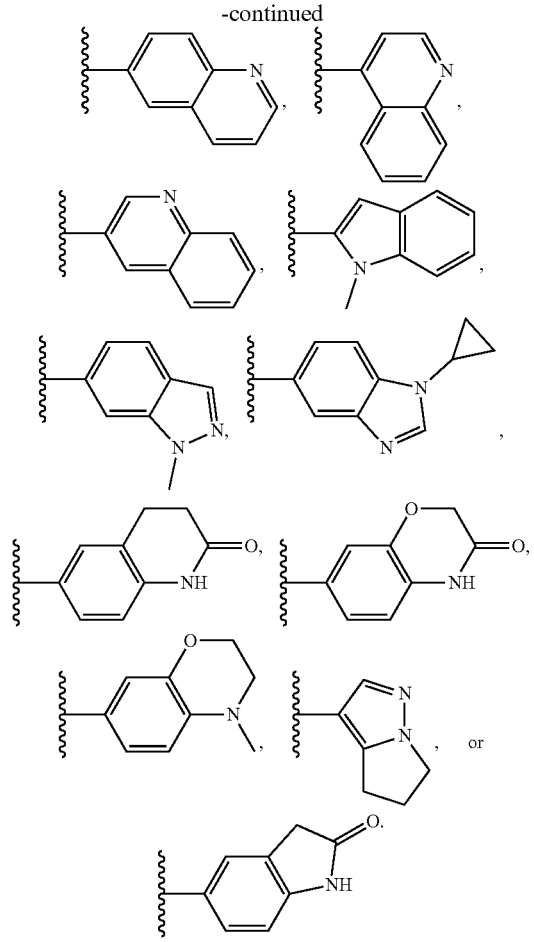
5. A compound of claim 4, or a pharmaceutically acceptable salt thereof, wherein
R¹ is
—CH₂C(O)OCH₃, CH₂CF₃,
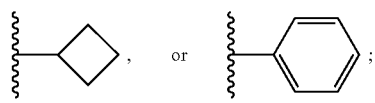 [SMILES: *C1CCC1 ; *c1ccccc1]
and
R² is
Cl, C(=CH₂)CH₂CH₂CH₃,
CH=CHCH₂OCH₃, CF₃, C(O)OCH₂CH₃,
CH=CHC₆H₅,
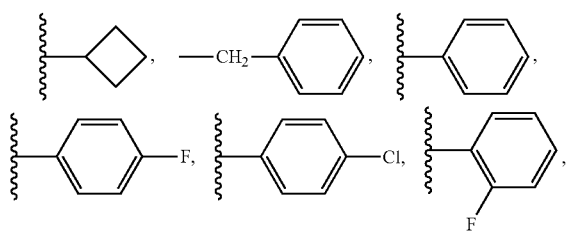
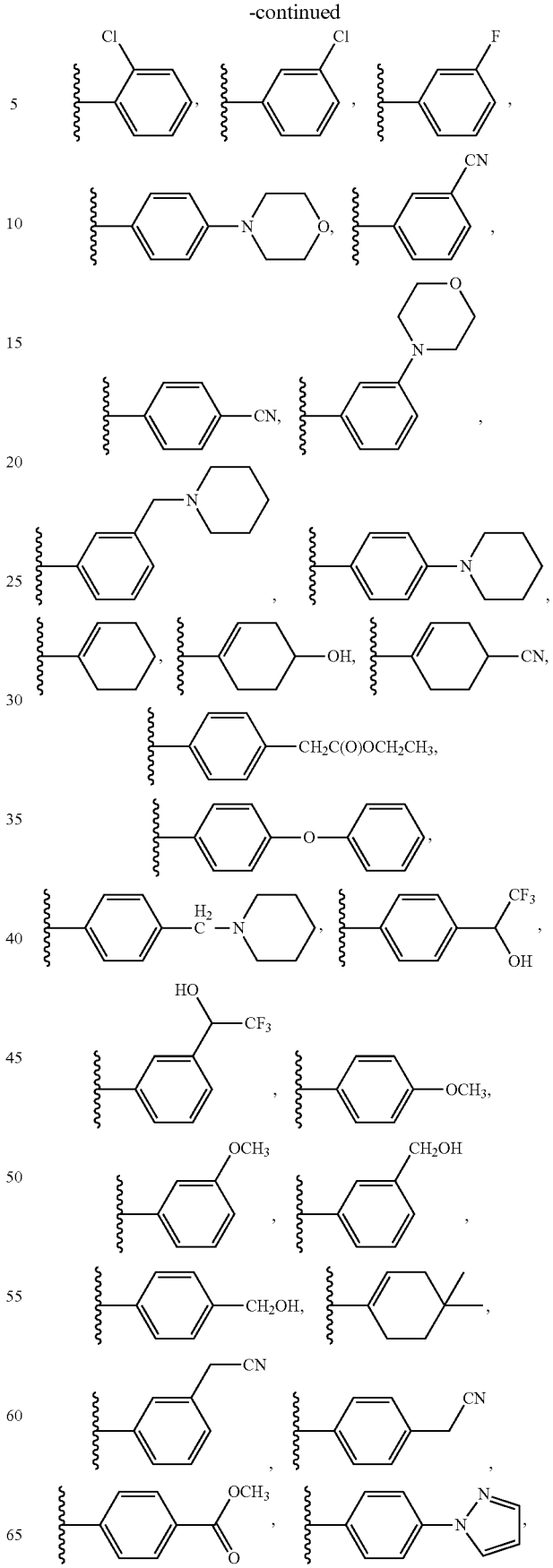

-continued
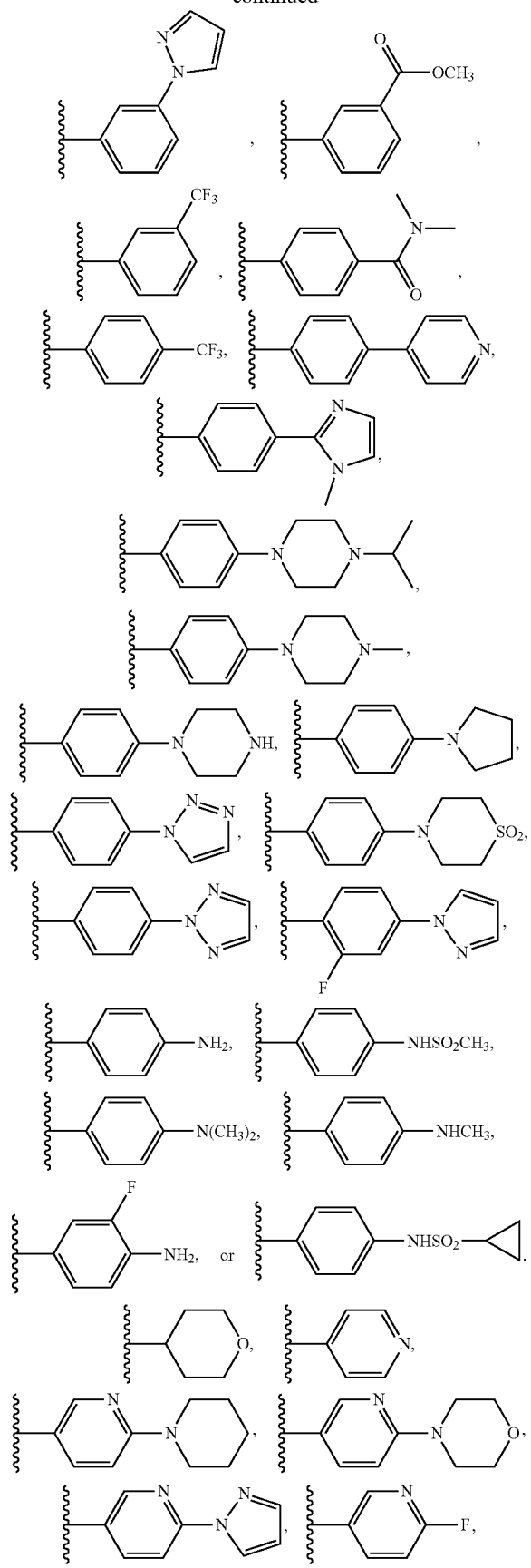
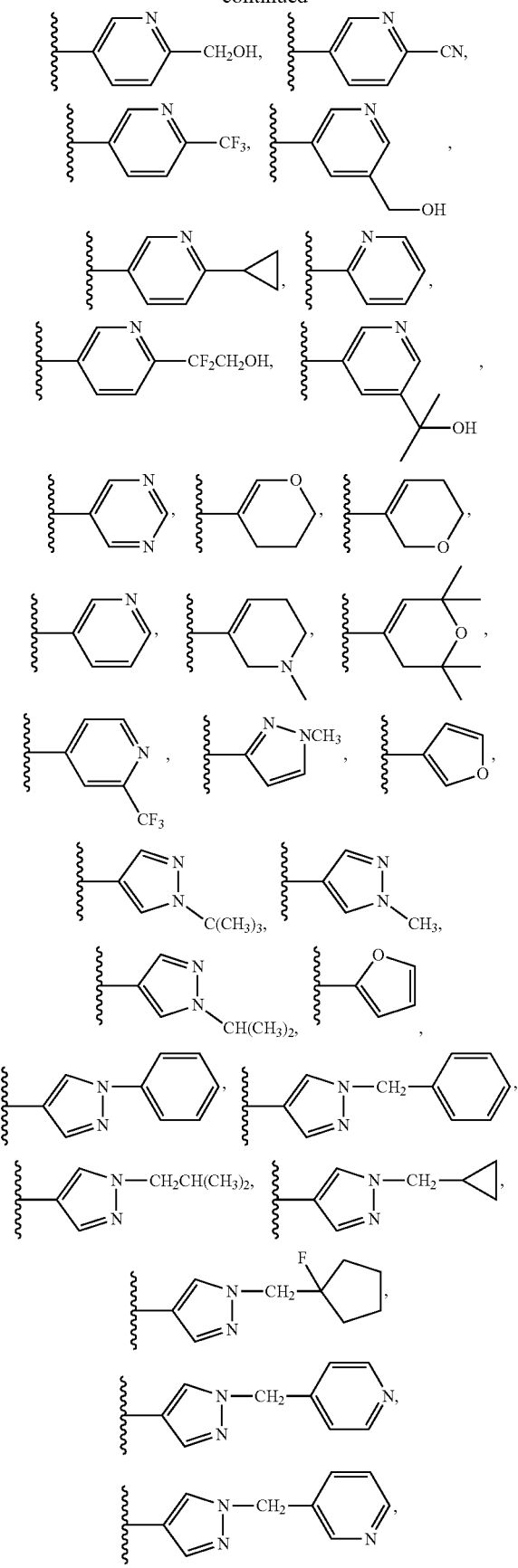

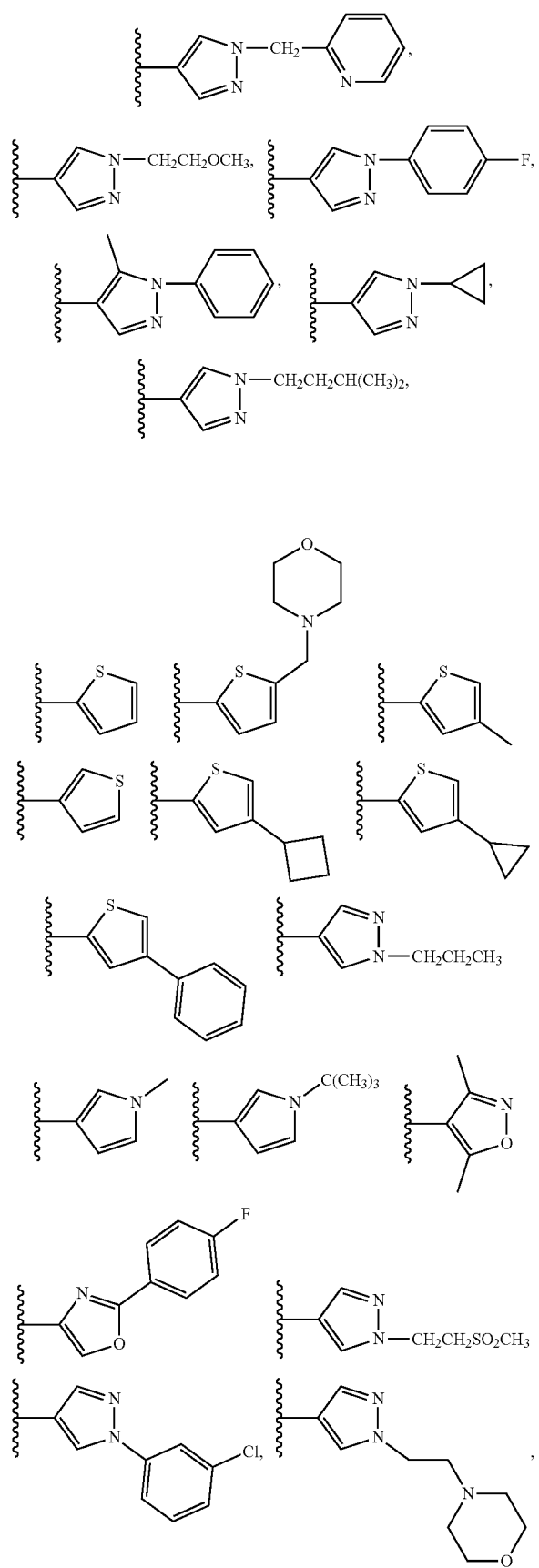
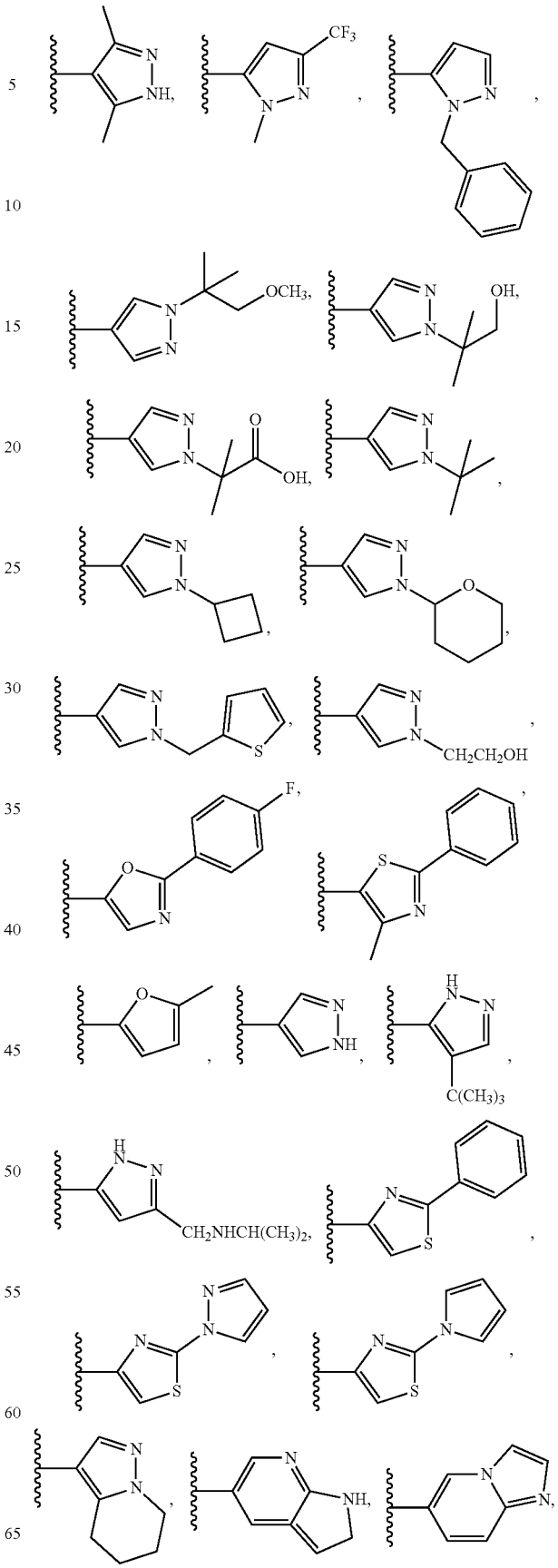

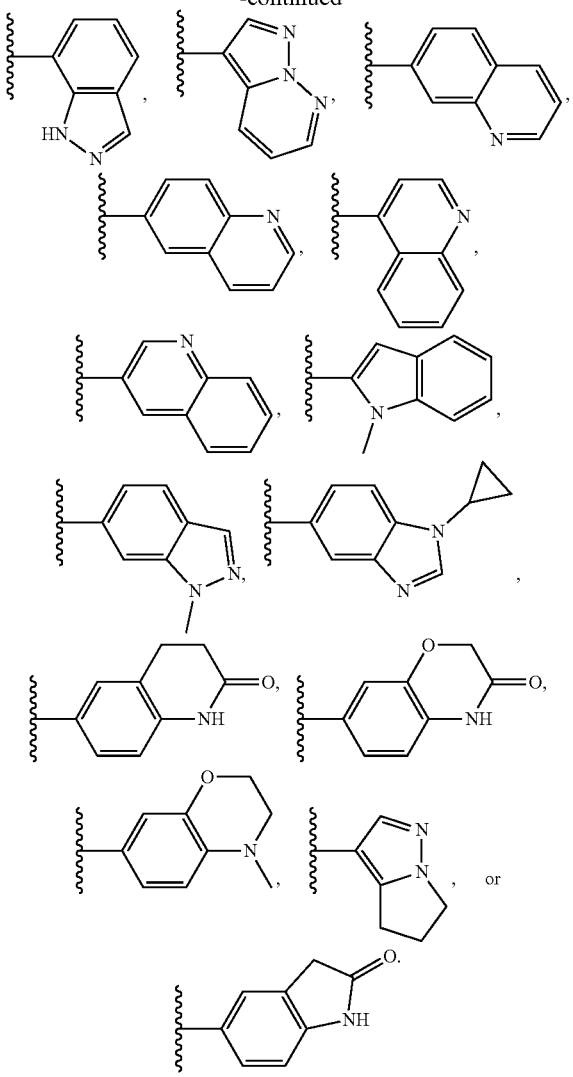

6. A compound of or a pharmaceutically acceptable salt thereof, which is 6-bromo-5-(1-(tert-butyl)-1H-pyrazol-4-yl)-[1,2,4]triazolo[1,5-a]pyrimidin-7(4H)-one,
5-(trifluoromethyl)[1,2,4]triazolo[1,5-a]pyrimidin-7(H)-one,
5-methyl-[1,2,4]triazolo[1,5-a]pyrimidin-7(4H)-one,
5-phenyl-[1,2,4]triazolo[1,5-a]pyrimidin-7(4H)-one,
5-propyl[1,2,4]triazolo[1,5-a]pyrimidin-7(4H)-one,
methyl (5-methyl-7-oxo-4,7-dihydro[1,2,4]triazolo[1,5-a]pyrimidin-6-yl)acetate,
5-(4-fluorophenyl)[1,2,4]triazolo[1,5-a]pyrimidin-7(4H)-one,
5-ethyl-[1,2,4]triazolo[1,5-a]pyrimidin-7(4H)-one,
ethyl 6-methyl-7-oxo-4,7-dihydro[1,2,4]triazolo[1,5-a]pyrimidine-5-carboxylate,
5-(1-methyl-1H-pyrazol-3-yl)[1,2,4]triazolo[1,5-a]pyrimidin-7(4H)-one,
5-methyl-6-(trifluoromethyl)[1,2,4]triazolo[1,5-a]pyrimidin-7(4H)-one,
6-cyclobutyl-5-methyl[1,2,4]triazolo[1,5-a]pyrimidin-7(4H)-one,
6-ethyl-5-(trifluoromethyl)[1,2,4]triazolo[1,5-a]pyrimidin-7(4H)-one,
6-fluoro-5-(trifluoromethyl)[1,2,4]triazolo[1,5-a]pyrimidin-7(4H)-one,
5-[1-(1-methylethyl)-1H-pyrazol-4-yl][1,2,4]triazolo[1,5-a]pyrimidin-7(4H)-one,
5-(tetrahydro-2H-pyran-4-yl)[1,2,4]triazolo[1,5-a]pyrimidin-7(4H)-one,
5-furan-3-yl[1,2,4]triazolo[1,5-a]pyrimidin-7(4H)-one,
5-pyridin-4-yl[1,2,4]triazolo[1,5-a]pyrimidin-7(4H)-one,
5-pyridin-2-yl[1,2,4]triazolo[1,5-a]pyrimidin-7(4H)-one,
5-furan-2-yl[1,2,4]triazolo[1,5-a]pyrimidin-7(4H)-one,
5-(4-chlorophenyl)[1,2,4]triazolo[1,5-a]pyrimidin-7(4H)one,
5-(4-chlorophenyl)[1,2,4]triazolo[1,5-a]pyrimidin-7(4H)-one,
5-(2-chlorophenyl)[1,2,4]triazolo[1,5-a]pyrimidin-7(4H)-one,
5-(2-fluorophenyl)[1,2,4]triazolo[1,5-a]pyrimidin-7(4H)-one,
5-(3-chlorophenyl)[1,2,4]triazolo[1,5-a]pyrimidin-7(4H)-one,
5-(3-fluorophenyl)[1,2,4]triazolo[1,5-a]pyrimidin-7(4H)-one,
5-(1-methyl-1H-pyrazol-4-yl)[1,2,4]triazolo[1,5-a]pyrimidin-7(4H)-one,
6-phenyl-5-propyl[1,2,4]triazolo[1,5-a]pyrimidin-7(4H)-one,
5-(1-methylethyl)[1,2,4]triazolo[1,5-a]pyrimidin-7(4H)-one,
6-(1-methylethyl)-5-phenyl[1,2,4]triazolo[1,5-a]pyrimidin-7(4H)-one,
6-cyclobutyl-5-(4-fluorophenyl)[1,2,4]triazolo[1,5-a]pyrimidin-7(4H)-one,
6-cyclobutyl-5-[1-(1-methylethyl)-1H-pyrazol-4-yl][1,2,4]triazolo[1,5-a]pyrimidin-7(4H)-one,
6-(1-methylethyl)-5-(1-methyl-1H-pyrazol-4-yl)[1,2,4]triazolo[1,5-a]pyrimidin-7(4H)-one,
5-(1-tert-butyl-1H-pyrazol-4-yl)-6-(2,2,2-trifluoroethyl)[1,2,4]triazolo[1,5-a]pyrimidin-7(4H)-one,
5-(1-isopentyl-1H-pyrazol-4-yl)-6-isopropyl-[1,2,4]triazolo[1,5-a]pyrimidin-7(4H)-one,
6-isopropyl-5-(thiophen-2-yl)-[1,2,4]triazolo[1,5-a]pyrimidin-7(4H)-one,
5-(1-tert-butyl-1H-pyrazol-4-yl)-6-(1-methylethyl)[1,2,4]triazolo[1,5-a]pyrimidin-7(4H)-one,
5-[1-(3-methylbutyl)-1H-pyrazol-4-yl]-6-(1-methylethyl)[1,2,4]triazolo[1,5-a]pyrimidin-7(4H)-one,
6-(1-methylethyl)-5-thiophen-2-yl[1,2,4]triazolo[1,5-a]pyrimidin-7(4H)-one,
6-tert-butyl-5-(1-tert-butyl-1H-pyrazol-4-yl)[1,2,4]triazolo[1,5-a]pyrimidin-7(4H)-one,
6-tert-butyl-5-(4-fluorophenyl)[1,2,4]triazolo[1,5-a]pyrimidin-7(4H)-one,
6-tert-butyl-5-(1-methyl-1H-pyrazol-4-yl)[1,2,4]triazolo[1,5-a]pyrimidin-7(4H)-one,
6-tert-butyl-5-(1-phenyl-1H-pyrazol-4-yl)[1,2,4]triazolo[1,5-a]pyrimidin-7(4H)-one,
6-(1-methylethyl)-5-(1-phenyl-1H-pyrazol-4-yl)[1,2,4]triazolo[1,5-a]pyrimidin-7(4H)-one,
5-(1-benzyl-1H-pyrazol-4-yl)-6-(1-methylethyl)[1,2,4]triazolo[1,5-a]pyrimidin-7(4H)-one,
6-(1-methylethyl)-5-(4-morpholin-4-ylphenyl)[1,2,4]triazolo[1,5-a]pyrimidin-7(4H)-one,
5-(4-fluorophenyl)-6-(1-methylethyl)[1,2,4]triazolo[1,5-a]pyrimidin-7(4H)-one,
6-(1-methylethyl)-5-[1-(2-methylpropyl)-1H-pyrazol-4-yl][1,2,4]triazolo[1,5-a]pyrimidin-7(4H)-one, 5-{1-[(1-fluorocyclopentyl)methyl]-1H-pyrazol-4-yl}-6-(1-methylethyl)[1,2,4]triazolo[1,5-a]pyrimidin-7(4H)-one,
5-[1-(cyclopropylmethyl)-1H-pyrazol-4-yl]-6-(1-methylethyl)[1,2,4]triazolo[1,5-a]pyrimidin-7(4H)-one,
6-(1-methylethyl)-5-[1-(pyridin-4-ylmethyl)-1H-pyrazol-4-yl][1,2,4]triazolo[1,5-a]pyrimidin-7(4H)-one,
5-[1-(2-methoxyethyl)-1H-pyrazol-4-yl]-6-(1-methylethyl)[1,2,4]triazolo[1,5-a]pyrimidin-7(4H)-one,
5-[1-(4-fluorophenyl)-1H-pyrazol-4-yl]-6-(1-methylethyl)[1,2,4]triazolo[1,5-a]pyrimidin-7(4H)-one,
5-(1-cyclopropyl-1H-pyrazol-4-yl)-6-(1-methylethyl)[1,2,4]triazolo[1,5-a]pyrimidin-7(4H)-one,
5-(1-ethyl-1H-pyrazol-4-yl)-6-(1-methylethyl)[1,2,4]triazolo[1,5-a]pyrimidin-7(4H)-one,
6-(1-methylethyl)-5-[1-(1-methylethyl)-1H-pyrazol-4-yl][1,2,4]triazolo[1,5-a]pyrimidin-7(4H)-one,
6-(1-methylethyl)-5-(1-propyl-1H-pyrazol-4-yl)[1,2,4]triazolo[1,5-a]pyrimidin-7(4H)-one,
6-(1-methylethyl)-5-(1-methylenebutyl)[1,2,4]triazolo[1,5-a]pyrimidin-7(4H)-one,
5-[(1E)-3-methoxyprop-1-en-1-yl]-6-(1-methylethyl)[1,2,4]triazolo[1,5-a]pyrimidin-7(4H)-one,
6-(1-methylethyl)-5-pyridin-4-yl[1,2,4]triazolo[1,5-a]pyrimidin-7(4H)-one,
6-(1-methylethyl)-5-pyridin-3-yl[1,2,4]triazolo[1,5-a]pyrimidin-7(4H)-one,
6-(1-methylethyl)-5-pyrimidin-5-yl[1,2,4]triazolo[1,5-a]pyrimidin-7(4H)-one,
6-(1-methylethyl)-5-(1-methyl-1H-pyrrol-3-yl)[1,2,4]triazolo[1,5-a]pyrimidin-7(4H)-one,
6-(1-methylethyl)-5-(5-methyl-1H-pyrazol-4-yl)[1,2,4]triazolo[1,5-a]pyrimidin-7(4H)-one,
5-cyclohex-1-en-1-yl-6-(1-methylethyl)[1,2,4]triazolo[1,5-a]pyrimidin-7(4H)-one,
5-(3,4-dihydro-2H-pyran-5-yl)-6-(1-methylethyl)[1,2,4]triazolo[1,5-a]pyrimidin-7(4H)-one,
5-(5,6-dihydro-2H-pyran-3-yl)-6-(1-methylethyl)[1,2,4]triazolo[1,5-a]pyrimidin-7(4H)-one,
5-(2-fluorophenyl)-6-(1-methylethyl)[1,2,4]triazolo[1,5-a]pyrimidin-7(4H)-one,
5-(3-fluorophenyl)-6-(1-methylethyl)[1,2,4]triazolo[1,5-a]pyrimidin-7(4H)-one,
5-(3,5-dimethylisoxazol-4-yl)-6-(1-methylethyl)[1,2,4]triazolo[1,5-a]pyrimidin-7(4H)-one,
6-(1-methylethyl)-5-(1-methyl-1,2,5,6-tetrahydropyridin-3-yl)[1,2,4]triazolo[1,5-a]pyrimidin-7(4H)-one,
5-(4-hydroxycyclohex-1-en-1-yl)-6-(1-methylethyl)[1,2,4]triazolo[1,5-a]pyrimidin-7(4H)-one,
3-[6-(1-methylethyl)-7-oxo-4,7-dihydro[1,2,4]triazolo[1,5-a]pyrimidin-5-yl]benzonitrile,
4-[6-(1-methylethyl)-7-oxo-4,7-dihydro[1,2,4]triazolo[1,5-a]pyrimidin-5-yl]benzonitrile,
6-(1-methylethyl)-5-[1-(pyridin-2-ylmethyl)-1H-pyrazol-4-yl][1,2,4]triazolo[1,5-a]pyrimidin-7(4H)-one,
6-(1-methylethyl)-5-[1-(pyridin-3-ylmethyl)-1H-pyrazol-4-yl][1,2,4]triazolo[1,5-a]pyrimidin-7(4H)-one,
6-(1-methylethyl)-5-(4-piperidin-1-ylphenyl)[1,2,4]triazolo[1,5-a]pyrimidin-7(4H)-one,
6-(1-methylethyl)-5-(3-piperidin-1-ylphenyl)[1,2,4]triazolo[1,5-a]pyrimidin-7(4H)-one,
5-[2-(4-fluorophenyl)-1,3-oxazol-4-yl]-6-(1-methylethyl)[1,2,4]triazolo[1,5-a]pyrimidin-7(4H)-one,
6-(1-methylethyl)-5-(3-morpholin-4-ylphenyl)[1,2,4]triazolo[1,5-a]pyrimidin-7(4H)-one,
ethyl {4-[6-(1-methylethyl)-7-oxo-4,7-dihydro[1,2,4]triazolo[1,5-a]pyrimidin-5-yl]phenyl}acetate,
6-(1-methylethyl)-5-(3-phenoxyphenyl)[1,2,4]triazolo[1,5-a]pyrimidin-7(4H)-one,
6-(1-methylethyl)-5-{1-[2-(methylsulfonyl)ethyl]-1H-pyrazol-4-yl}[1,2,4]triazolo[1,5-a]pyrimidin-7(4H)-one,
6-(1-methylethyl)-5-[4-(piperidin-1-ylmethyl)phenyl][1,2,4]triazolo[1,5-a]pyrimidin-7(4H)-one,
6-(1-methylethyl)-5-[3-(piperidin-1-ylmethyl)phenyl][1,2,4]triazolo[1,5-a]pyrimidin-7(4H)-one,
6-(1-methylethyl)-5-[4-(2,2,2-trifluoro-1-hydroxyethyl)phenyl][1,2,4]triazolo[1,5-a]pyrimidin-7(4H)-one,
5-[1-(3-chlorophenyl)-1H-pyrazol-4-yl]-6-(1-methylethyl)[1,2,4]triazolo[1,5-a]pyrimidin-7(4H)-one,
6-(1-methylethyl)-5-[1-(2-morpholin-4-ylethyl)-1H-pyrazol-4-yl][1,2,4]triazolo[1,5-a]pyrimidin-7(4H)-one,
6-(1-methylethyl)-5-(4,5,6,7-tetrahydropyrazolo[1,5-a]pyridin-3-yl)[1,2,4]triazolo[1,5-a]pyrimidin-7(4H)-one,
6-(1-methylethyl)-5-[3-(2,2,2-trifluoro-1-hydroxyethyl)phenyl][1,2,4]triazolo[1,5-a]pyrimidin-7(4H)-one,
6-(1-methylethyl)-5-[(E)-2-phenylethenyl][1,2,4]triazolo[1,5-a]pyrimidin-7(4H)-one,
4-[6-(1-methylethyl)-7-oxo-4,7-dihydro[1,2,4]triazolo[1,5-a]pyrimidin-5-yl]cyclohex-3-ene-1-carbonitrile,
5-(3-methoxyphenyl)-6-(1-methylethyl)[1,2,4]triazolo[1,5-a]pyrimidin-7(4H)-one,
5-(4-methoxyphenyl)-6-(1-methylethyl)[1,2,4]triazolo[1,5-a]pyrimidin-7(4H)-one,
5-[3-(hydroxymethyl)phenyl]-6-(1-methylethyl)[1,2,4]triazolo[1,5-a]pyrimidin-7(4H)-one,
5-[4-(hydroxymethyl)phenyl]-6-(1-methylethyl)[1,2,4]triazolo[1,5-a]pyrimidin-7(4H)-one,
6-(1-methylethyl)-5-(1,3,5-trimethyl-1H-pyrazol-4-yl)[1,2,4]triazolo[1,5-a]pyrimidin-7(4H)-one,
5-(4,4-dimethylcyclohex-1-en-1-yl)-6-(1-methylethyl)[1,2,4]triazolo[1,5-a]pyrimidin-7(4H)-one,
5-(4-chlorophenyl)-6-(1-methylethyl)[1,2,4]triazolo[1,5-a]pyrimidin-7(4H)-one,
5-(3-chlorophenyl)-6-(1-methylethyl)[1,2,4]triazolo[1,5-a]pyrimidin-7(4H)-one,
5-(2-chlorophenyl)-6-(1-methylethyl)[1,2,4]triazolo[1,5-a]pyrimidin-7(4H)-one,
{3-[6-(1-methylethyl)-7-oxo-4,7-dihydro[1,2,4]triazolo[1,5-a]pyrimidin-5-yl]phenyl}acetonitrile,
{4-[6-(1-methylethyl)-7-oxo-4,7-dihydro[1,2,4]triazolo[1,5-a]pyrimidin-5-yl]phenyl}acetonitrile,
6-(1-methylethyl)-5-(1H-pyrrolo[2,3-b]pyridin-5-yl)[1,2,4]triazolo[1,5-a]pyrimidin-7(4H)-one,
5-imidazo[1,2-a]pyridin-6-yl-6-(1-methylethyl)[1,2,4]triazolo[1,5-a]pyrimidin-7(4H)-one,
5-(1H-benzimidazol-6-yl)-6-(1-methylethyl)[1,2,4]triazolo[1,5-a]pyrimidin-7(4H)-one,
5-(1H-indazol-4-yl)-6-(1-methylethyl)[1,2,4]triazolo[1,5-a]pyrimidin-7(4H)-one,
6-(1-methylethyl)-5-pyrazolo[1,5-b]pyridazin-3-yl[1,2,4]triazolo[1,5-a]pyrimidin-7(4H)-one,
6-(1-methylethyl)-5-quinolin-7-yl[1,2,4]triazolo[1,5-a]pyrimidin-7(4H)-one,
6-(1-methylethyl)-5-quinolin-6-yl[1,2,4]triazolo[1,5-a]pyrimidin-7(4H)-one,
6-(1-methylethyl)-5-quinolin-4-yl[1,2,4]triazolo[1,5-a]pyrimidin-7(4H)-one,
6-(1-methylethyl)-5-quinolin-3-yl[1,2,4]triazolo[1,5-a]pyrimidin-7(4H)-one,
6-(1-methylethyl)-5-(1-methyl-1H-indol-2-yl)[1,2,4]triazolo[1,5-a]pyrimidin-7(4H)-one, 6-(1-methylethyl)-5-(1-methyl-1H-indazol-5-yl)[1,2,4]triazolo[1,5-a]pyrimidin-7(4H)-one,
methyl 4-[6-(1-methylethyl)-7-oxo-4,7-dihydro[1,2,4]triazolo[1,5-a]pyrimidin-5-yl]benzoate,
methyl 3-[6-(1-methylethyl)-7-oxo-4,7-dihydro[1,2,4]triazolo[1,5-a]pyrimidin-5-yl]benzoate,
6-(1-methylethyl)-5-(2,2,6,6-tetramethyl-3,6-dihydro-2H-pyran-4-yl)[1,2,4]triazolo[1,5-a]pyrimidin-7(4H)-one,
6-(1-methylethyl)-5-[4-(1H-pyrazol-1-yl)phenyl][1,2,4]triazolo[1,5-a]pyrimidin-7(4H)-one,
6-(1-methylethyl)-5-[3-(1H-pyrazol-1-yl)phenyl][1,2,4]triazolo[1,5-a]pyrimidin-7(4H)-one,
6-(1-methylethyl)-5-[4-(trifluoromethyl)phenyl][1,2,4]triazolo[1,5-a]pyrimidin-7(4H)-one,
6-(1-methylethyl)-5-[3-(trifluoromethyl)phenyl][1,2,4]triazolo[1,5-a]pyrimidin-7(4H)-one,
N,N-dimethyl-4-[6-(1-methylethyl)-7-oxo-4,7-dihydro[1,2,4]triazolo[1,5-a]pyrimidin-5-yl]benzamide,
6-(1-methylethyl)-5-[1-methyl-3-(trifluoromethyl)-1H-pyrazol-5-yl][1,2,4]triazolo[1,5-a]pyrimidin-7(4H)-one,
6-(1-methylethyl)-5-(4-pyridin-4-ylphenyl)[1,2,4]triazolo[1,5-a]pyrimidin-7(4H)-one,
5-(1-cyclopropyl-1H-benzimidazol-6-yl)-6-(1-methylethyl)[1,2,4]triazolo[1,5-a]pyrimidin-7(4H)-one,
6-(1-methylethyl)-5-[4-(1-methyl-1H-imidazol-2-yl)phenyl][1,2,4]triazolo[1,5-a]pyrimidin-7(4H)-one,
5-(1-benzyl-1H-pyrazol-5-yl)-6-(1-methylethyl)[1,2,4]triazolo[1,5-a]pyrimidin-7(4H)-one,
5-[1-(2-methoxy-1,1-dimethylethyl)-1H-pyrazol-4-yl]-6-(1-methylethyl)[1,2,4]triazolo[1,5-a]pyrimidin-7(4H)-one,
6-(1-methylethyl)-5-{4-[4-(1-methylethyl)piperazin-1-yl]phenyl}[1,2,4]triazolo[1,5-a]pyrimidin-7(4H)-one,
6-(1-methylethyl)-5-(4-pyrrolidin-1-ylphenyl)[1,2,4]triazolo[1,5-a]pyrimidin-7(4H)-one,
6-(1-methylethyl)-5-[4-(1H-1,2,3-triazol-1-yl)phenyl][1,2,4]triazolo[1,5-a]pyrimidin-7(4H)-one,
5-[4-(1,1-dioxidothiomorpholin-4-yl)phenyl]-6-(1-methylethyl)[1,2,4]triazolo[1,5-a]pyrimidin-7(4H)-one,
6-(1-methylethyl)-5-[4-(2H-1,2,3-triazol-2-yl)phenyl][1,2,4]triazolo[1,5-a]pyrimidin-7(4H)-one,
5-[2-fluoro-4-(1H-pyrazol-1-yl)phenyl]-6-(1-methylethyl)[1,2,4]triazolo[1,5-a]pyrimidin-7(4H)-one,
5-(4-aminophenyl)-6-(1-methylethyl)[1,2,4]triazolo[1,5-a]pyrimidin-7(4H)-one,
N-{4-[6-(1-methylethyl)-7-oxo-4,7-dihydro[1,2,4]triazolo[1,5-a]pyrimidin-5-yl]phenyl}methanesulfonamide,
6-[6-(1-methylethyl)-7-oxo-4,7-dihydro[1,2,4]triazolo[1,5-a]pyrimidin-5-yl]-3,4-dihydroquinolin-2(1H)-one,
7-[6-(1-methylethyl)-7-oxo-4,7-dihydro[1,2,4]triazolo[1,5-a]pyrimidin-5-yl]-2H-1,4-benzoxazin-3(4H)-one,
5-[4-(dimethylamino)phenyl]-6-(1-methylethyl)[1,2,4]triazolo[1,5-a]pyrimidin-7(4H)-one,
5-[4-(methylamino)phenyl]-6-(1-methylethyl)[1,2,4]triazolo[1,5-a]pyrimidin-7(4H)-one,
5-(4-methyl-3,4-dihydro-2H-1,4-benzoxazin-7-yl)-6-(1-methylethyl)[1,2,4]triazolo[1,5-a]pyrimidin-7(4H)-one,
6-(1-methylethyl)-5-[4-(4-methylpiperazin-1-yl)phenyl][1,2,4]triazolo[1,5-a]pyrimidin-7(4H)-one,
5-[1-(2-hydroxy-1,1-dimethylethyl)-1H-pyrazol-4-yl]-6-(1-methylethyl)[1,2,4]triazolo[1,5-a]pyrimidin-7(4H)-one,
6-(1-methylethyl)-5-[5-(morpholin-4-ylmethyl)thiophen-2-yl][1,2,4]triazolo[1,5-a]pyrimidin-7(4H)-one,
5-(1-cyclobutyl-1H-pyrazol-4-yl)-6-(1-methylethyl)[1,2,4]triazolo[1,5-a]pyrimidin-7(4H)-one,
6-(1-methylethyl)-5-[1-(thiophen-2-ylmethyl)-1H-pyrazol-4-yl][1,2,4]triazolo[1,5-a]pyrimidin-7(4H)-one,
5-[1-(2-hydroxyethyl)-1H-pyrazol-4-yl]-6-(1-methylethyl)[1,2,4]triazolo[1,5-a]pyrimidin-7(4H)-one,
5-(5,6-dihydro-4H-pyrrolo[1,2-b]pyrazol-3-yl)-6-(1-methylethyl)[1,2,4]triazolo[1,5-a]pyrimidin-7(4H)-one,
5-[2-(4-fluorophenyl)-1,3-oxazol-5-yl]-6-(1-methylethyl)[1,2,4]triazolo[1,5-a]pyrimidin-7(4H)-one,
6-(1-methylethyl)-5-(5-methyl-1-phenyl-1H-pyrazol-4-yl)[1,2,4]triazolo[1,5-a]pyrimidin-7(4H)-one,
6-(1-methylethyl)-5-(4-methylthiophen-2-yl)[1,2,4]triazolo[1,5-a]pyrimidin-7(4H)-one,
6-(1-methylethyl)-5-(4-methyl-2-phenyl-1,3-thiazol-5-yl)[1,2,4]triazolo[1,5-a]pyrimidin-7(4H)-one,
6-(1-methylethyl)-5-(5-methylfuran-2-yl)[1,2,4]triazolo[1,5-a]pyrimidin-7(4H)-one,
6-(1-methylethyl)-5-(4-piperazin-1-ylphenyl)[1,2,4]triazolo[1,5-a]pyrimidin-7(4H)-one,
5-(4-amino-3-fluorophenyl)-6-(1-methylethyl)[1,2,4]triazolo[1,5-a]pyrimidin-7(4H)-one,
6-(1-methylethyl)-5-[2-(trifluoromethyl)pyridin-4-yl][1,2,4]triazolo[1,5-a]pyrimidin-7(4H)-one,
5-[5-(1-hydroxy-1-methylethyl)pyridin-3-yl]-6-(1-methylethyl)[1,2,4]triazolo[1,5-a]pyrimidin-7(4H)-one,
6-(1-methylethyl)-5-(1H-pyrazol-4-yl)[1,2,4]triazolo[1,5-a]pyrimidin-7(4H)-one,
6-(1-methylethyl)-5-(2-oxo-2,3-dihydro-1H-indol-5-yl)[1,2,4]triazolo[1,5-a]pyrimidin-7(4H)-one,
N-{4-[6-(1-methylethyl)-7-oxo-4,7-dihydro[1,2,4]triazolo[1,5-a]pyrimidin-5-yl]phenyl}cyclopropanesulfonamide,
6-(1-methylethyl)-5-[1-(tetrahydro-2H-pyran-2-yl)-1H-pyrazol-4-yl][1,2,4]triazolo[1,5-a]pyrimidin-7(4H)-one,
6-(1-methylethyl)-5-(6-piperidin-1-ylpyridin-3-yl)[1,2,4]triazolo[1,5-a]pyrimidin-7(4H)-one,
6-(1-methylethyl)-5-(6-morpholin-4-ylpyridin-3-yl)[1,2,4]triazolo[1,5-a]pyrimidin-7(4H)-one,
6-(1-methylethyl)-5-[6-(1H-pyrazol-1-yl)pyridin-3-yl][1,2,4]triazolo[1,5-a]pyrimidin-7(4H)-one,
5-(6-fluoropyridin-3-yl)-6-(1-methylethyl)[1,2,4]triazolo[1,5-a]pyrimidin-7(4H)-one,
5-[6-(hydroxymethyl)pyridin-3-yl]-6-(1-methylethyl)[1,2,4]triazolo[1,5-a]pyrimidin-7(4H)-one,
5-[6-(1-methylethyl)-7-oxo-4,7-dihydro[1,2,4]triazolo[1,5-a]pyrimidin-5-yl]pyridine-2-carbonitrile,
6-(1-methylethyl)-5-[6-(trifluoromethyl)pyridin-3-yl][1,2,4]triazolo[1,5-a]pyrimidin-7(4H)-one,
5-(6-cyclopropylpyridin-3-yl)-6-(1-methylethyl)[1,2,4]triazolo[1,5-a]pyrimidin-7(4H)-one,
5-(1-tert-butyl-1H-pyrrol-3-yl)-6-(1-methylethyl)[1,2,4]triazolo[1,5-a]pyrimidin-7(4H)-one,
5-(3-tert-butyl-1H-pyrazol-5-yl)-6-(1-methylethyl)[1,2,4]triazolo[1,5-a]pyrimidin-7(4H)-one,
6-(1-methylethyl)-5-(2-phenyl-1,3-thiazol-4-yl)[1,2,4]triazolo[1,5-a]pyrimidin-7(4H)-one,
6-(1-methylethyl)-5-[2-(1H-pyrazol-1-yl)-1,3-thiazol-4-yl][1,2,4]triazolo[1,5-a]pyrimidin-7(4H)-one,
6-(1-methylethyl)-5-thiophen-3-yl[1,2,4]triazolo[1,5-a]pyrimidin-7(4H)-one, 6-(1-methylethyl)-5-(1,3-oxazol-5-yl)[1,2,4]triazolo[1,5-a]pyrimidin-7(4H)-one,
6-(1-methylethyl)-5-[2-(1H-pyrrol-1-yl)-1,3-thiazol-4-yl][1,2,4]triazolo[1,5-a]pyrimidin-7(4H)-one,
6-(1-methylethyl)-5-[4-(1-methylethyl)thiophen-2-yl][1,2,4]triazolo[1,5-a]pyrimidin-7(4H)-one,
5-(4-cyclobutylthiophen-2-yl)-6-(1-methylethyl)[1,2,4]triazolo[1,5-a]pyrimidin-7(4H)-one,
5-(4-cyclopropylthiophen-2-yl)-6-(1-methylethyl)[1,2,4]triazolo[1,5-a]pyrimidin-7(4H)-one,
6-(1-methylethyl)-5-(4-phenylthiophen-2-yl)[1,2,4]triazolo[1,5-a]pyrimidin-7(4H)-one,
5-(6-(1,1-difluoro-2-hydroxyethyl)pyridin-3-yl)-6-isopropyl[1,2,4]triazolo[1,5a]pyrimidin-7(4H)-one,
5-[6-(1,1-difluoro-2-hydroxyethyl)pyridin-3-yl]-6-(1-methylethyl)[1,2,4]triazolo[1,5-a]pyrimidin-7(4H)-one,
5-[5-(hydroxymethyl)pyridin-3-yl]-6-(1-methylethyl)[1,2,4]triazolo[1,5-a]pyrimidin-7(4H)-one,
6-isopropyl-5-(3-((isopropylamino)methyl)-1H-pyrazol-5-yl)-[1,2,4]triazolo[1,5-a]pyrimidin-7(4H)-one,
2-(4-(6-isopropyl-7-oxo-4,7-dihydro-[1,2,4]triazolo[1,5-a]pyrimidin-5-yl)-1H-pyrazol-1-yl)-2-methylpropanoic acid, or
5-(1-(tert-butyl)-1H-pyrazol-4-yl)-6-cyclopropyl-[1,2,4]triazolo[1,5-a]pyrimidin-7(4H)-one.

* * * * *